United States Patent [19]
Ankersen

[11] Patent Number: 6,083,908
[45] Date of Patent: Jul. 4, 2000

[54] COMPOUNDS WITH GROWTH HORMONE RELEASING PROPERTIES

[75] Inventor: Michael Ankersen, Frederiksberg, Denmark

[73] Assignee: Novo Nordisk A/S, Bagsvaerd, Denmark

[21] Appl. No.: 09/228,300

[22] Filed: Jan. 12, 1999

Related U.S. Application Data

[60] Provisional application No. 60/072,053, Jan. 21, 1998, and provisional application No. 60/090,588, Jun. 25, 1998.

[30] Foreign Application Priority Data

Jan. 16, 1998 [DK] Denmark .............................. 98 00056
Jun. 15, 1998 [DK] Denmark .............................. 98 00799

[51] Int. Cl.[7] ........................... A61K 38/00; A01N 37/18
[52] U.S. Cl. ................................ 514/2; 514/19; 514/614; 514/664; 564/464
[58] Field of Search ................... 514/2, 19, 614, 514/664; 564/464

[56] References Cited

FOREIGN PATENT DOCUMENTS

| 2070618 | 9/1981 | United Kingdom . |
| 97/23508 | 7/1997 | WIPO . |
| 98/58950 | 12/1998 | WIPO . |

*Primary Examiner*—Bennett Celsa
*Attorney, Agent, or Firm*—Steve T. Zelson; Carol E. Vozek

[57] ABSTRACT

Compounds of Formula I

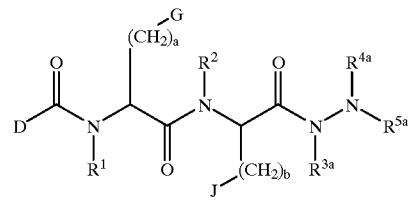

and their use for treating medical disorders resulting from a deficiency in growth hormone are disclosed, wherein $R^1$, $R^2$, $R^{3a}$, $R^{4a}$, $R^{5a}$, G, J and D are as defined in the specification.

17 Claims, No Drawings

COMPOUNDS WITH GROWTH HORMONE RELEASING PROPERTIES

CROSS-REFERENCE TO RELATED APPLICATIONS

This application claims priority under 35 U.S.C. 119 of U.S. provisional application Nos. 60/072,053 and 60/090,588 filed Jan. 21, 1998 and Jun. 25, 1998, respectively, and of Danish application nos. 0056/98 and PA 1998 00799 filed Jan. 16, 1998 and Jun. 15, 1998, respectively, the contents of which are fully incorporated herein by reference.

FIELD OF INVENTION

The present invention relates to novel compounds, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilisation and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthethic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason parenteral administration is preferred.

The use of certain compounds for increasing the levels of growth hormone in mammals has previously been proposed, e.g. in EP 18 072, EP 83 864, WO 89/07110, WO 89/01711, WO 89/10933, WO 88/9780, WO 83/02272, WO 91/18016, WO 92/101711, WO 93/04081, WO 9517422, WO 9517423, WO 9514666, WO9419367, WO9534311, WO9602530, WO9615148, WO9613265, WO9622997, WO9635713, WO9638471, WO09632943, WO9700894, WO9706803, WO9709060, WO9707117, WO9711697, WO9722620, WO9723508, WO9724369, and WO9734604.

The composition of growth hormone releasing compounds is important for their growth hormone releasing potency as well as their bioavailability. It is therefore an object of the present invention to provide novel hydrazide compounds with growth hormone releasing properties. Moreover, it is an object to provide novel growth hormone releasing compounds (growth hormone secretagogues) which are specific and/or selective and have no or substantially no side-effects, such as e.g. release of LH, FSH, TSH, ACTH, vasopressin, oxytocin, cortisol and/or prolactin. It is also an object to provide compounds which have good oral bioavailability.

SUMMARY OF THE INVENTION

In accordance with the present invention there is provided novel compounds which act directly on the pituitary cells under normal experimental conditions in vitro to release growth hormone therefrom.

These growth hormone releasing compounds can be utilized in vitro as unique research tools for understanding, inter alia, how growth hormone secretion is regulated at the pituitary level.

Moreover, the growth hormone releasing compounds of the present invention can also be administered in vivo to increase endogenous growth hormone release.

DESCRIPTION OF THE INVENTION

Accordingly, the present invention relates to a compound of the general formula I

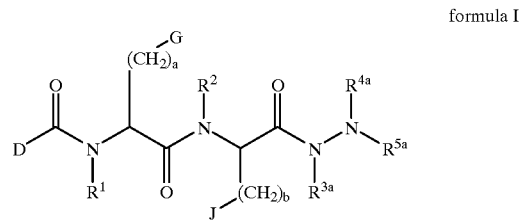

formula I wherein $R^1$ and $R^2$ are independently hydrogen, or $C_{1-6}$-alkyl optionally substituted with one or more aryl or hetaryl;

$R^{3a}$ is hydrogen, $C_{1-6}$alkyl optionally substituted with one or more aryl or hetaryl, or aryl or hetaryl optionally substituted with one or more $C_{1-6}$-alkyl;

$R^{4a}$ is $C_{1-6}$alkyl optionally substituted with one or more aryl or hetaryl, or $C_{1-7}$-acyl;

$R^{5a}$ is hydrogen, $C_{1-6}$-alkyl optionally substituted with one or more aryl or hetaryl, or aryl or hetaryl optionally substituted with one or more $C_{1-6}$-alkyl; or $R^{3a}$ and $R^{4a}$ together with the nitrogen atoms to which they are attached may form a heterocyclic system optionally substituted with one or more $C_{1-6}$-halkyl, halogen, amino, hydroxyl, aryl or hetaryl; or $R^{3a}$ and $R^{5a}$ together with the nitrogen atoms to which they are attached may form a heterocyclic system optionally substituted with one or more $C_{1-6}$-alkyl, halogen, amino, hydroxyl, aryl or hetaryl; or $R^{4a}$ and $R^{5a}$ together with the nitrogen atom to which they are attached may form a heterocyclic system optionally substituted with one or more $C_{1-6}$-calkyl, halogen, amino, hydroxyl, aryl or hetaryl;

a and b are independently 0, 1 or 2;

G is hydrogen, ——O——$(CH_2)_k$——$R^{27}$,

-continued

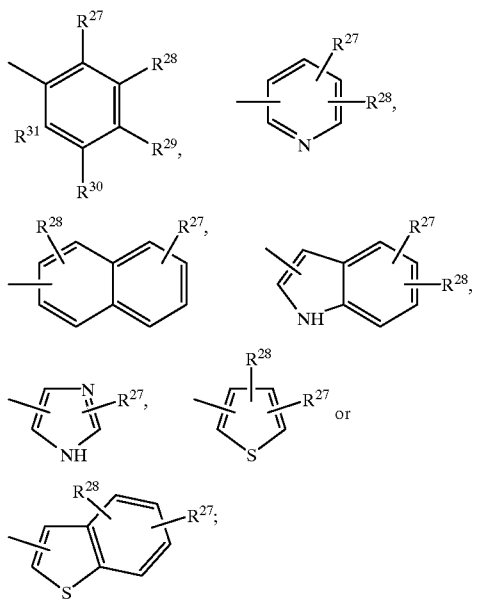

J is hydrogen, —O—(CH$_2$)$_l$—R$^{32}$,

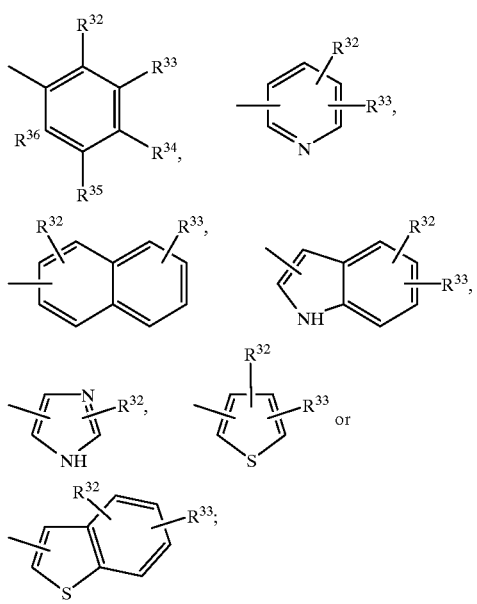

wherein R$^{27}$, R$^{28}$, R$^{29}$, R$^{30}$, R$^{31}$, R$^{32}$, R$^{33}$, R$^{34}$, R$^{35}$ and R$^{36}$ independently are hydrogen, halogen, aryl, hetaryl, C$_{1-6}$-alkyl or C$_{1-6}$-alkoxy;

k and l are independently 0, 1, or 2;

D is

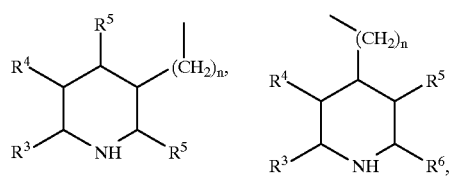

-continued

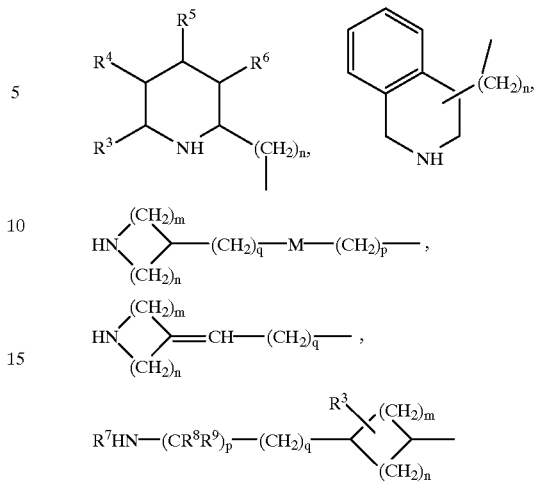

wherein R$^3$, R$^4$, R$^5$, R$^6$, R$^7$, R$^8$ and R$^9$ are independently hydrogen or C$_{1-6}$-alkyl optionally substituted with one or more halogen, amino, hydroxyl, aryl or hetaryl;

n, m and q are independently 0, 1, 2, or 3;

p is 0 or 1;

M is —CR$^{11}$=CR$^{11a}$—, arylene, hetarylene, —O—, —S— or a valence bond;

R$^{11}$ and R$^{11a}$ are independently hydrogen, or C$_{1-6}$-alkyl optionally substituted with one or more aryl or hetaryl; or D is R$^7$—NH—(CR$^8$R$^9$)$_p$—(CH$_2$)$_m$—M—(CHR$^{10}$)$_o$—(CH$_2$)$_n$— wherein R$^7$, R$^8$, R$^9$ and R$^{10}$ are independently hydrogen or C$_{1-6}$alkyl optionally substituted with one or more halogen, amino, hydroxyl, aryl or hetaryl; or R$^7$ and R$^8$ or R$^7$ and R$^9$ or R$^8$ and R$^9$ may optionally form —(CH$_2$)$_i$—U—(CH$_2$)$_j$—, wherein i and j are independently are 1 or 2 and U is —O—, —S— or a valence bond;

n and m are independently 0, 1, 2, or 3;

o and p are independently 0 or 1;

M is —CR$^{11}$=CR$^{11a}$—, arylene, hetarylene, —O—, —S— or a valence bond;

R$^{11}$ and R$^{11a}$ are independently hydrogen, or C$_{1-6}$-alkyl optionally substituted with one or more aryl or hetaryl;

or a pharmaceutically acceptable salt thereof.

Moreover, the compounds of formula I may comprise any optical isomers thereof, in the form of separated, pure or partially purified optical isomers or racemic mixtures thereof.

In the compound of general formula I there are two chiral carbon atoms which may be in the R- and/or S-configuration. In one embodiment both chiral carbon atoms are in the R-configuration.

Furthermore, the compounds of formula I may have one or more carbon-carbon double bonds with the possibility of geometric isomeri, and it is intended that possible stereoisomers (E or Z isomers) are included in the scope of the invention, unless a special geometric isomer is specified.

In one embodiment of the compound of formula I R$^1$ is hydrogen. In another embodiment of the compound of formula I R$^1$ is C$_{1-6}$-alkyl, such as C$_{1-4}$-alkyl, in particular methyl.

In a further embodiment of the compound of formula I $R^2$ is hydrogen. In another embodiment of the compound of formula I $R^2$ is $C_{1-6}$-alkyl, such as $C_{1-4}$-alkyl, in particular methyl.

In a still further embodiment of the compound of formula I $R^{3a}$ is hydrogen. In another embodiment of the compound of formula I $R^{3a}$ is $C_{1-6}$-alkyl, such as $C_{1-4}$-alkyl, in particular methyl.

In a further embodiment of the compound of formula I $R^{4a}$ is $C_{1-6}$-alkyl, such as $C_{1-4}$-alkyl, in particular methyl. In another embodiment of the compound of formula I $R^{4a}$ is $C_{1-7}$-acyl, such as $C_{2-4}$-acyl, in particular acetyl.

In a still further embodiment of the compound of formula I $R^{5a}$ is hydrogen. In another embodiment of the compound of formula I $R^{5a}$ is $C_{1-6}$-alkyl, such as $C_{1-4}$-alkyl, in particular methyl.

In a further embodiment of the compound of formula I $R^{3a}$ and $R^{4a}$ may together with the nitrogen atoms to which they are attached form a heterocyclic system, which is optionally substituted with one or more $C_{1-6}$-alkyl, halogen, amino, hydroxyl, aryl or hetaryl. Such heterocyclic system may be aromatic or non-aromatic and may be selected from e.g. pyrazole, pyridazine, triazine, indazole, phthalazine, cinnoline, pyrazolidine, oxopyrazolidine or pyrazoline. In a particular embodiment the heterocyclic system is oxopyrazolidine.

In a still further embodiment of the compound of formula I $R^{3a}$ and $R^{5a}$ together with the nitrogen atoms to which they are attached form a heterocyclic system, which is optionally substituted with one or more $C_{1-6}$-alkyl, halogen, amino, hydroxyl, aryl or hetaryl. Such heterocyclic system may be aromatic or non-aromatic and may be selected from e.g. pyrazole, pyridazine, triazine, indazole, phthalazine, cinnoline, pyrazolidine or pyrazoline.

In a further embodiment of the compound of formula I $R^{4a}$ and $R^{5a}$ together with the nitrogen atom to which they are attached form a heterocyclic system, which is optionally substituted with one or more $C_{1-6}$-alkyl, halogen, amino, hydroxyl, aryl or hetaryl. Such heterocyclic system may be aromatic or non-aromatic and may be selected from e.g. aziridine, dithiazine, pyrrol, imidazol, pyrazole, isoindole, indole, indazole, purine, pyrrolidine, pyrroline, imidazolidine, imidazoline, pyrazolidine, pyrazoline, piperidine, piperazine, indoline, isoindoline, or morpholine, in particular pyrrolidine or piperidine.

When $R^{3a}$ and $R^{4a}$ form a heterocyclic system $R^{4a}$ and $R^{5a}$ may simultaneously also form a heterocyclic system or $R^{5a}$ may be hydrogen, $C_{1-6}$-alkyl optionally substituted with one or more aryl or hetaryl, or aryl or hetaryl optionally substituted with one or more $C_{1-6}$-alkyl.

When $R^{3a}$ and $R^{5a}$ form a heterocyclic system $R^{4a}$ and $R^{5a}$ may simultaneously also form a heterocyclic system or $R^{4a}$ may be $C_{1-6}$-alkyl optionally substituted with one or more aryl or hetaryl, or $C_{1-7-acyl}$.

In a still further embodiment of the compound of formula I a is 1.

In a further embodiment of the compound of formula I b is 1. In another embodiment b is 2.

In a still further embodiment of the compound of formula IG is

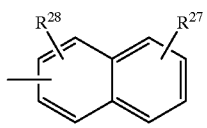

wherein $R^{27}$ and $R^{28}$ independently are hydrogen, halogen, aryl, hetaryl, $C_{1-6}$-alkyl or $C_{1-6}$-alkoxy. In a further embodiment $R^{27}$ and $R^{28}$ are both hydrogen. In a still further embodiment G is 1-naphthyl or 2-naphthyl. In the compound of the above formula IG is preferably 2-naphthyl.

In a still further embodiment of the compound of formula IG is

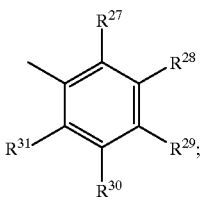

wherein $R^{27}$, $R^{28}$, $R^{29}$, $R^{30}$ and $R^{31}$ independently are hydrogen, halogen, aryl, hetaryl, $C_{1-6}$-alkyl or $C_{1-6}$-alkoxy. In a further embodiment $R^{27}$, $R^{28}$, $R^{30}$ and $R^{31}$ are hydrogen and $R^{29}$ is aryl. In a still further embodiment $R^{29}$ is phenyl. In the compound of the above formula IG is preferably biphenyl-4-yl.

In a further embodiment of the compound of formula IG is —O—$(CH_2)_k$—$R^{27}$, wherein $R^{27}$ is hydrogen, halogen, aryl, hetaryl, $C_{1-6}$-alkyl or $C_{1-6}$-alkoxy; k is 0, 1 or 2. In a still further embodiment $R^{27}$ is aryl. In a further embodiment k is 1. In the compound of the above formula IG is preferably benxyloxy.

In a still further embodiment of the formula of compound IG is

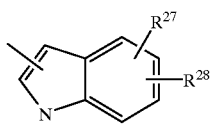

wherein $R^{27}$ and $R^{28}$ independently are hydrogen, halogen, aryl, hetaryl, $C_{1-6}$-alkyl or $C_{1-6}$-alkoxy. In a further embodiment $R^{27}$ and $R^{28}$ are both hydrogen. In a still further embodiment G is 1H-indol-3-yl.

In a further embodiment of the compound of formula IJ is

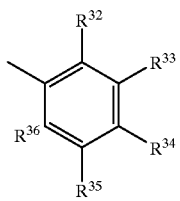

wherein $R^{32}$, $R^{33}$, $R^{34}$, $R^{35}$ and $R^{36}$ independently are hydrogen, halogen, aryl, hetaryl, $C_{1-6}$-alkyl or $C_{1-6}$-alkoxy. In one embodiment $R^{32}$, $R^{33}$, $R^{34}$, $R^{35}$ and $R^{36}$ are all hydrogen. J is preferably phenyl.

In a still further embodiment of the compound of formula IJ is

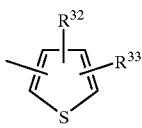

wherein $R^{32}$ and $R^{33}$ independently are hydrogen, halogen, aryl, hetaryl, $C_{1-6}$-alkyl or $C_{1-6}$-alkoxy. In a further embodiment $R^{32}$ and $R^{33}$ are both hydrogen. J is preferably 2-thienyl.

In a still further embodiment of the compound of formula ID is

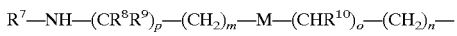

wherein $R^7$, $R^8$, $R^9$ and $R^{10}$ are independently hydrogen or $C_{1-6}$-alkyl optionally substituted with one or more halogen, amino, hydroxyl, aryl or hetaryl;

n and m are independently 0, 1, 2, or 3;

o and p are independently 0 or 1;

M is —$CR^{11}$=$CR^{11a}$—, arylene, —O—, or —S—;

$R^{11}$ and $R^{11a}$ are independently hydrogen, or $C_{1-6}$-alkyl optionally substituted with one or more aryl or hetaryl. In one embodiment $R^7$ is hydrogen. In a second embodiment R7 is $C_{1-6}$-alkyl, in particular methyl. In a third embodiment $R^8$ is hydrogen. In a further embodiment $R^8$ is $C_{1-6}$alkyl, in particular methyl. In a still further embodiment $R^9$ is hydrogen. In a still further embodiment $R^9$ is $C_{1-6}$ alkyl, in particular methyl.

In a further embodiment $R^8$ and $R^9$ form —(CH$_2$)$_i$—U—(CH$_2$)$_j$—, wherein i and j independently are 1 or 2 and U is —O—, —S— or a valence bond. In a still further embodiment U is a valence bond. In a still further embodiment the sum i+j is 3.

In a further embodiment n is 0. In a still further embodiment m is 0. In a further embodiment m is 1. In a further embodiment o is 0. In a still further embodiment p is 0. In a further embodiment p is 1. In a still further embodiment M is —$CR^{11}$=$CR^{11a}$—, aryl, —O—, or —S—. In a further embodiment M is —CH=CH—. In a still further embodiment M is phenylene.

In a still further embodiment of the compound of formula ID is

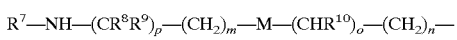

wherein $R^7$, $R^8$, $R^9$ and $R^{10}$ independently are hydrogen or $C_{1-6}$alkyl optionally substituted with one or more halogen, amino, hydroxyl, aryl or hetaryl;

n and m are independently 0, 1, 2, or 3;

o and p are independently 0 or 1;

M is a valence bond;

$R^{11}$ and $R^{11a}$ are independently hydrogen, or $C_{1-6}$-alkyl optionally substituted with one or more aryl or hetaryl. In one embodiment $R^7$ is hydrogen. In a second embodiment R7 is methyl. In a third embodiment $R^8$ is hydrogen. In a further embodiment $R^8$ is $C_{1-6}$alkyl, in particular methyl. In a still further embodiment $R^9$ is hydrogen. In a still further embodiment $R^9$ is $C_{1-6}$alkyl, in particular methyl. In a further embodiment n is 0. In a still further embodiment m is 0. In a further embodiment m is 1. In a further embodiment o is 0. In a still further embodiment p is 0. In a further embodiment p is 1.

In the compound of the above formula ID is preferably 3-aminomethylphenyl, 4-amino-4-methylpent-(1E)-enyl, N-methyl-3-aminomethylphenyl, 3-(1-aminocyclobutyl)-1-propenyl or 1-amino-1-methylethyl.

Preferred compounds of formula I of the invention are:

(2E)-5-Amino-5-methylhex-2-enoic acid N-((1R)-1-{N-[(1R)-2-(N'-acetylhydrazino)-1-benzyl-2-oxoethyl]-N-methylcarbamoyl}-2-(2-naphthyl)ethyl)-N-methylamide

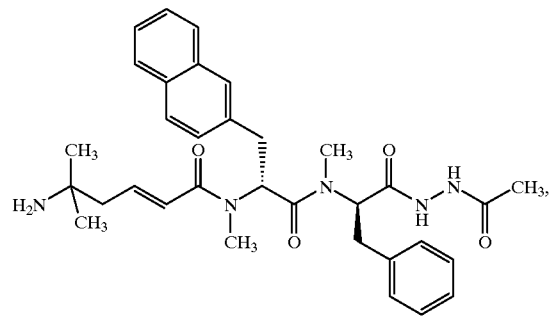

(2E)-5-Amino-5-methylhex-2-enoic acid N-((1R)-1-{N-[(1R)-2-(N'-acetyl-N-methylhydrazino)-1-benzyl-2-oxoethyl]-N-methylcarbamoyl)}-2-(2-naphthyl)ethyl)-N-methylamide

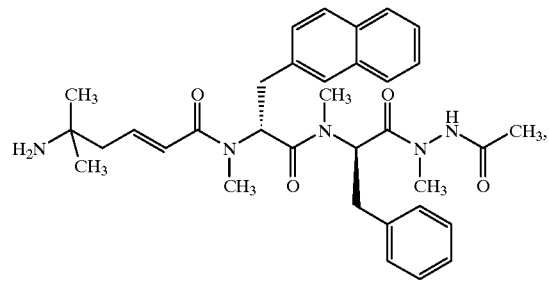

(2E)-5-Amino-5-methylhex-2-enoic acid N-((1R)-1-{N-[(1R)-2-(N'-acetyl-N'-methylhydrazino)-1-benzyl-2-oxoethyl]-N-methylcarbamoyl}-2-(2-naphthyl)ethyl)-N-methylamide

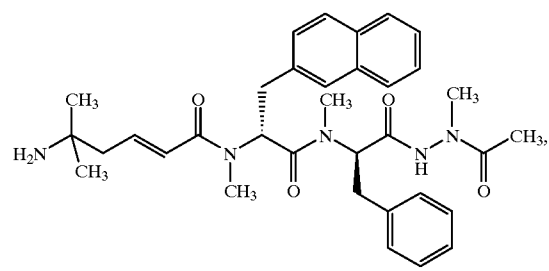

(2E)-5-Amino-5-methylhex-2-enoic acid N-methyl-N-((1R)-1-{N-methyl-N-[(1R)-2-phenyl-1-(N,N',N'-trimethylhydrazinocarbonyl)ethyl]carbamoyl}-2-(2-naphthyl)-ethyl)amide

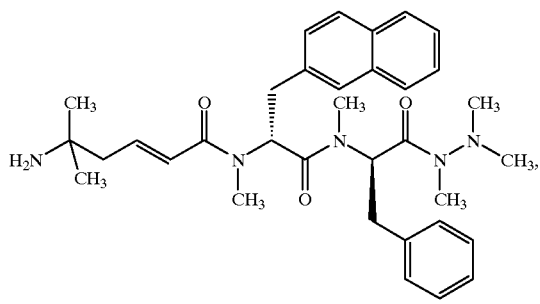

3-Aminomethyl-N-methyl-N-((1R)-1-{N-methyl-N-[(1R)-2-phenyl-1-(N,N',N'-trimethylhydrazinocarbonyl)ethyl]carbamoyl}-2-(2-naphthyl)ethyl)benzamide

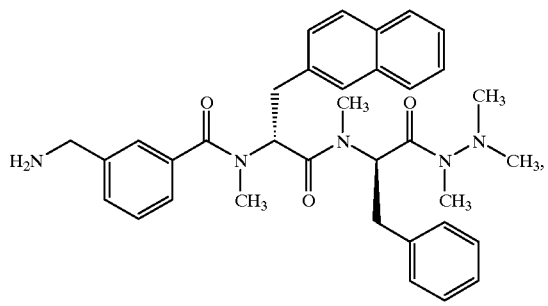

(2E)-5-Amino-5-methylhex-2-enoic acid N-((1R)-1-(N-[(1R)-1-(N',N'-dimethylhydrazinocarbonyl)-2-phenylethyl]-N-methylcarbamoyl)-2-(2-naphthyl)ethyl)-N-methylamide

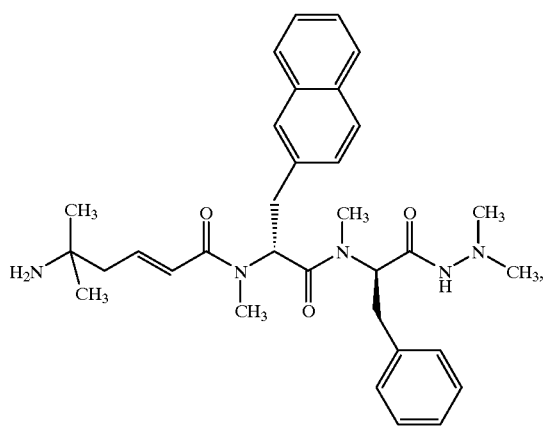

(2E)-5-Amino-5-methylhex-2-enoic acid N-((1R)-1-(N-[(1R)-1-(N',N'-dimethylhydrazinocarbonyl)-2-(2-thienyl)ethyl]-N-methylcarbamoyl)-2-(2-naphthyl)ethyl)-N-methylamide

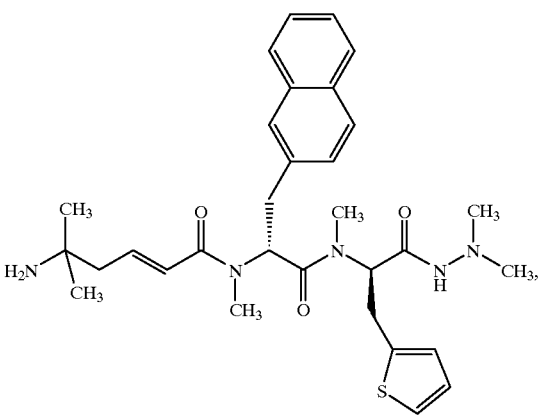

N-((1R)-1-(N-[(1R)-1-(N',N'-Dimethylhydrazinocarbonyl)-2-phenylethyl]-N-methylcarbamoyl)-2-(2-naphthyl)ethyl)-N-methyl-3-(N-

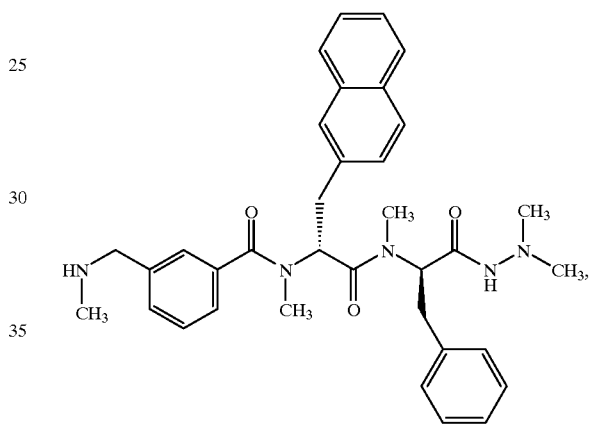

methylaminomethyl)benzamide (2E)-5-Amino-5-methylhex-2-enoic acid N-((1R)-2-(biphenyl4-yl)-1-(N-methyl-N-[(1R)-2-phenyl-1-(N,N',N'-trimethylhydrazinocarbonyl)ethyl]carbamoyl)ethyl)-N-methylamide

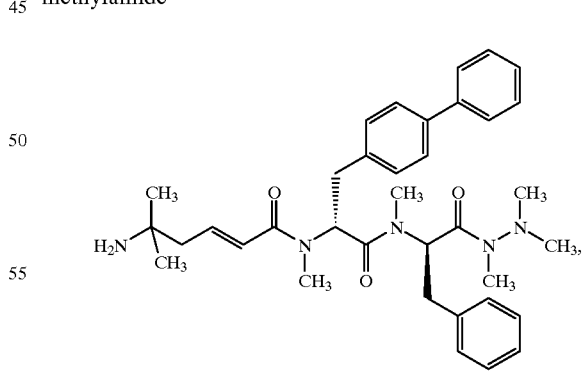

(2E)4-(1-Aminocyclobutyl)but-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide

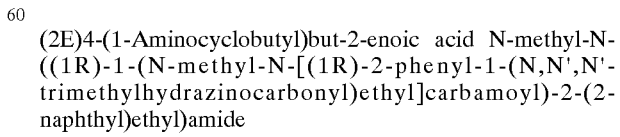

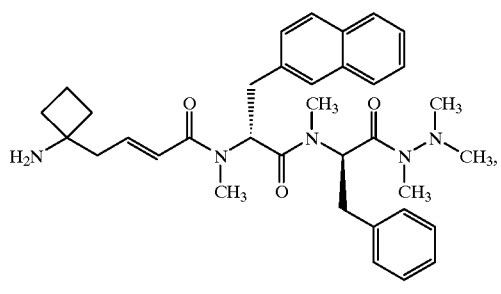

(2E)-5-Amino-5-methylhex-2-enoic acid N-((1R)-2-(biphenyl-4-yl)-1-(N-methyl-N-[(1R)-2-phenyl-1-((piperidin-1-yl)carbamoyl)ethyl]carbamoyl)ethyl)-N-methylamide

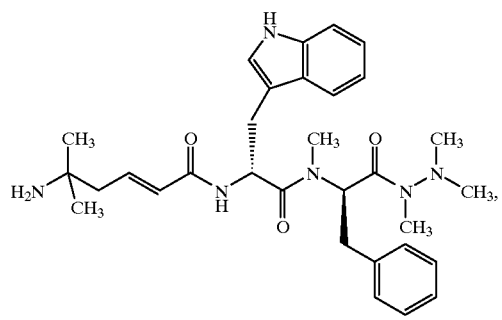

2-Amino-N-((1R)-2-(1H-indol-3-yl)-1-(N-methyl-N-[(1R)-2-phenyl-1-(N,N',N'-trimethylhydrazinocarbonyl)ethyl]carbamoyl)ethyl)-2-methylpropionamide

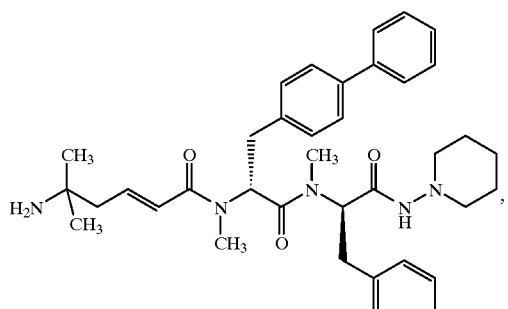

(2E)-5-Amino-5-methylhex-2-enoic acid N-methyl-N-((1R)-1-(N-methyl-N-[((1R)-2-(2-thienyl)-1-(N,N',N'-methylhydrazinocarbonyl)ethyl]carbamoyl)-2-(2-naphthyl)ethyl)amide

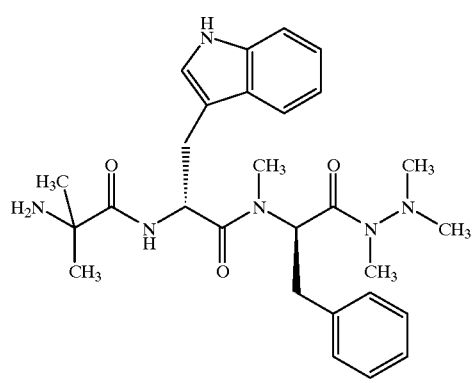

(2E)-5-Amino-5-methylhex-2-enoic acid N-methyl-N-((1R)-1-(N-methyl-N-[(1R)-1-(N-methyl-N-(piperidin-1-yl)carbamoyl)-2-phenylethyl]carbamoyl)-2-(2-naphthyl)ethyl)amide

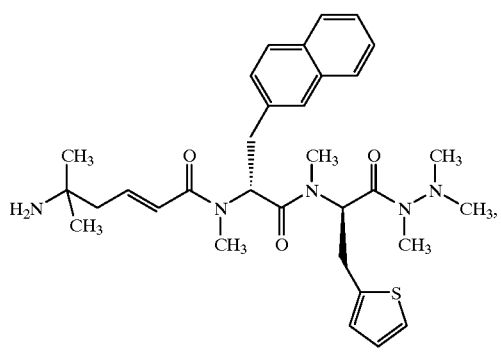

(2E)-5-Amino-5-methylhex-2-enoic acid N-((1R)-2-(1H-indol-3-yl)-1-(N-methyl-N-[(1R)-2-phenyl-1-(N,N',N'-trimethylhydrazinocarbonyl)ethyl]carbamoyl)ethyl)amide

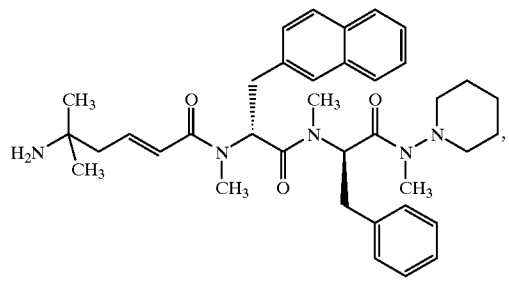

(2E)-5-Amino-5-methylhex-2-enoic acid N-methyl-N-((1R)-1-(N-methyl-N-[(1R)-1-(N-methyl-N-(piperidin-1-yl)carbamoyl)-2-(2-thienyl)ethyl]carbamoyl)-2-(2-naphthyl)ethyl)amide

13

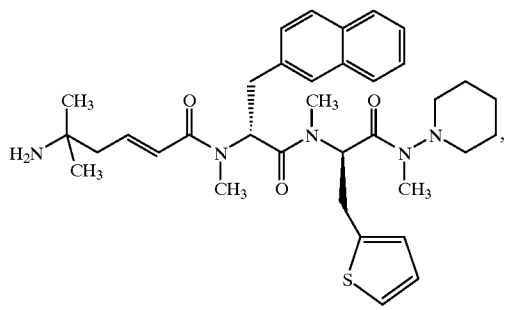

(2E)-5-Amino-5-methylhex-2-enoic acid N-((1R)-1-(N-[(1R)-1-benzyl-2-oxo-2-(3-oxopyrazolidin-1-yl)ethyl]-N-methylcarbamoyl)-2-(2-naphthyl)ethyl-N-methylamide

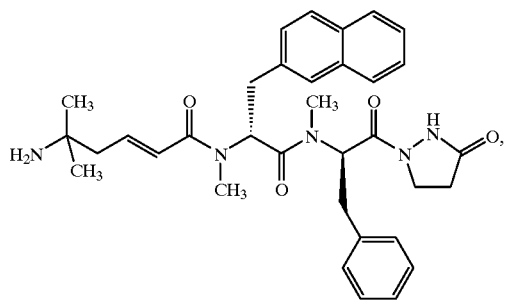

(2E)-5-Amino-5-methylhex-2-enoic acid N-methyl-N-((1R)-1-{N-methyl-N-[(1R)-2-phenyl-1-((piperidin-1-yl)carbamoyl)ethyl]carbamoyl}-2-(2-naphthyl)ethyl)amide

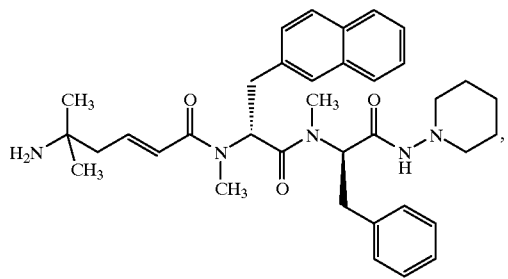

(2E)-5-Amino-5-methylhex-2-enoic acid N-methyl-N-((1R)-1{N-methyl-N-[(1R)-2-phenyl-1-((pyrrolidin-1-yl)carbamoyl)ethyl]carbamoyl}-2-(2-naphthyl)ethyl)amide

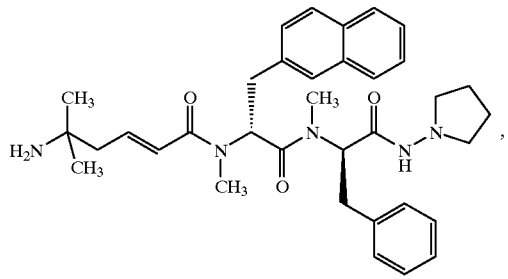

(2E)-5-Amino-5-methylhex-2-enoic acid N-((1R)-2-(biphenyl4-yl)-1-{N-methyl-N-[(1R)-2-phenyl-1-

14

((pyrrolidin-1-yl)carbamoyl)ethyl]carbamoyl}ethyl)-N-methylamide

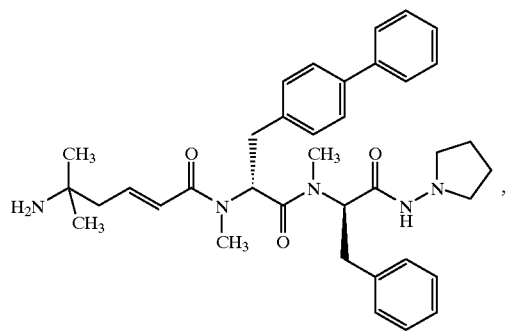

2-Amino-N-(2-benzyloxy-1-{N-methyl-N-[(1R)-2-phenyl-1-(N,N',N'-trimethylhydrazinocarbonyl)ethyl]carbamoyl}ethyl)-2-methylpropionamide

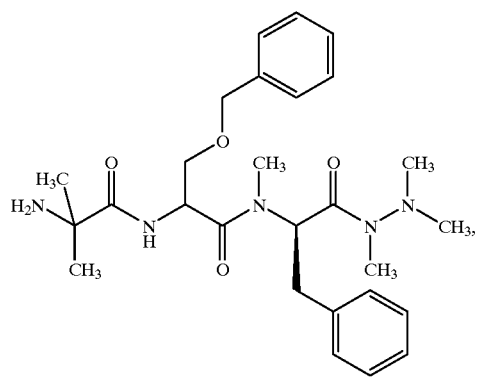

2-Amino-N-(2-benzyloxy-1-{N-[(1R)-1-(N',N'-dimethylhydrazinocarbonyl)-3-phenylpropyl]-N-methylcarbamoyl}ethyl)-2-methylpropionamide

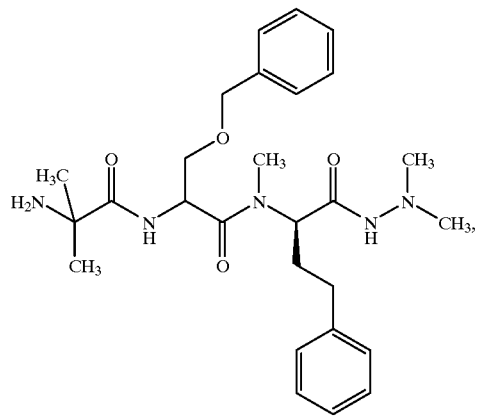

2-Amino-N-{2-benzyloxy-1-[N-((1R)-1-(N',N'-dimethylhydrazinocarbonyl)-3-phenylpropyl)carbamoyl]ethyl}-2-methylpropionamide

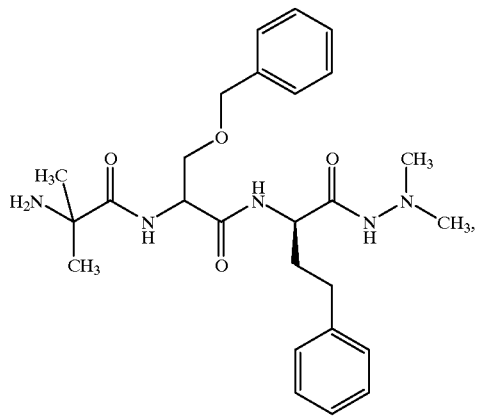

2-Amino-N-[(1R)-1-[(1R)-1-(N',N'-dimethylhydrazinocarbonyl)-3-phenylpropylcarbamoyl]-2-(1H-indol-3-yl)ethyl]-2-methylpropionamide

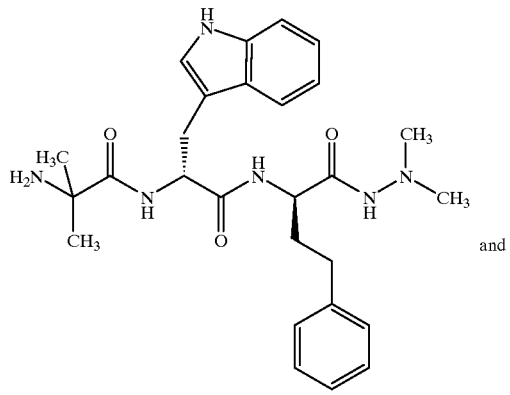

and

2-Amino-N-[(1R)-1-{N-[(1R)-1-(N',N'-dimethylhydrazinocarbonyl)-3-phenylpropyl]-N-methylcarbamoyl}-2-(1H-indol-3-yl)ethyl]-2-methylpropionamide

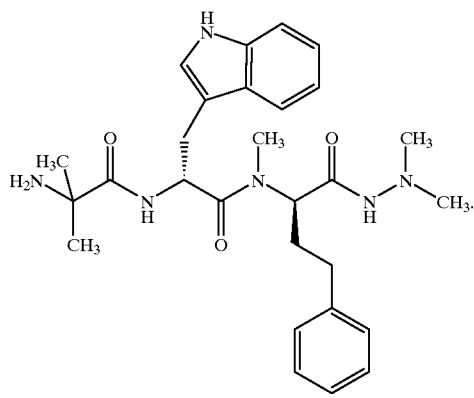

The most preferred compound of the above preferred compounds is (2E)-5-Amino-5-methylhex-2-enoic acid N-methyl-N-((1R)-1-{N-methyl-N-[(1R)-2-phenyl-1-(N,N',N'-trimethylhydrazinocarbonyl)ethyl]carbamoyl}-2-(2-naphthyl)-ethyl)amide.

General Method

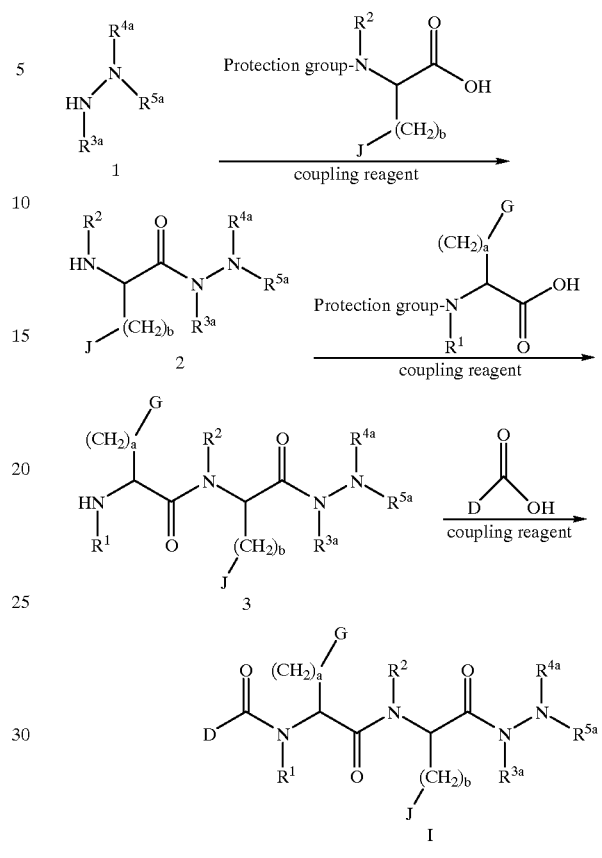

Compounds of the general structure I may be prepared from mono-, di- or tri-substituted hydrazines or hydrazones and appropriate protected amino acids with suitable coupling reagents such as 1-ethyl-3-(3-dimethylaminopropyl) carbodiimide hydrochloride and 1-hydroxybenzotriazole or other coupling reagents known in the art of peptide coupling in an appriate solvent such as dimethylformamid or dichloromethane. The appropriate amino acids may be protected and deprotected by methods known in the art and described by e.g. T. W. Green (Protective Groups in Organic Synthesis, 2. Ed., John Wiley and Sons, New York 1991).

It is believed that compounds of formula I exhibit an improved resistance to proteolytic degradation by enzymes because they are non-natural, in particular because the natural amide bonds are replaced by non-natural amide bond mimetics. The increased resistance to proteolytic degradation combined with the reduced size of the compounds of the invention in comparison with known hormone releasing peptides is expected to improve their bioavailability compared to that of the peptides suggested in the prior literature.

In the above structural formulas and throughout the present specification, the following terms have the indicated meanings:

The $C_{1-6}$-alkyl, $C_{1-6}$-alkylene, $C_{1-4}$-alkyl or $C_{1-4}$-alkylene groups specified above are intended to Iinclude those alkyl or alkylene groups of the designated length in either a linear or branched or cyclic configuration. Examples of linear alkyl are methyl, ethyl, propyl, butyl, pentyl, and hexyl and their corresponding divalent moieties, such as ethylene. Examples of branched alkyl are isopropyl, sec-butyl, tert-butyl, isopentyl, and isohexyl and their corresponding divalent moieties, such as isopropylene. Examples of cyclic alkyl are $C_{3-6}$-cycloalkyl such as cyclopropyl, cyclobutyl, cyclopentyl and cyclohexyl and their corresponding divalent moieties, such as cyclopropylene.

The $C_{1-6}$-alkoxy groups specified above are intended to include those alkoxy groups of the designated length in either a linear or branched or cyclic configuration. Examples of linear alkoxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are cyclopropyloxy, cyclobutyloxy, cyclopentyloxy and cyclohexyloxy.

The $C_{1-7}$-acyl groups specified above are intended to include those acyl groups of the designated length in either a linear or branched or cyclic configuration. Examples of linear acyl are formyl, acetyl, propionyl, butyryl, valeryl, etc. Examples of branched are isobutyryl, isovaleryl, pivaloyl, etc. Examples of cyclic are cyclopentylcarbonyl, cyclohexylcarbonyl, etc.

In the present context, the term "aryl" is intended to include monovalent carbocyclic aromatic ring moieties, being either monocyclic, bicyclic or polycyclic, e.g. selected from the group consisting of phenyl and naphthyl, optionally substituted with one or more $C_{1-6}$-alkyl, $C_{1-6}$-alkoxy, halogen, amino or aryl.

In the present context, the term "aryiene" is intended to include dilvalent carbocyclic aromatic ring moieties, being either monocyclic, bicyclic or polycyclic, e.g. selected from the group consisting of phenylene and naphthylene, optionally substituted with one or more $C_{1-6}$-alkyl, $C_{1-6}$-alkoxy, halogen, amino or aryl.

In the present context, the term "hetaryl" is intended to include monovalent heterocyclic aromatic ring moieties, being either monocyclic, bicyclic or polycyclic, e.g. selected from the group consisting of pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, or isothiazolyl, optionally substituted by one or more $C_{1-6}$-alkyl, $C_{1-6}$-alkoxy, halogen, amino or aryl.

In the present context, the term "hetarylene" is intended to include divalent heterocyclic aromatic ring moieties, being either monocyclic, bicyclic or polycyclic, e.g. selected from the group consisting of pyridinediyl, 1-H-tetrazolediyl, thiazoldiyl, imidazolediyl, indolediyl, pyrimidinediyl, thiadiazolediyl, pyrazolediyl, oxazolediyl, isoxazolediyl, oxadiazolediyl, thiophenediyl, quinolinediyl, pyrazinediyl, or isothiazolediyl, optionally substituted by one or more $C_{1-6}$-alkyl, $C_{1-6}$-alkoxy, halogen, amino or aryl.

In the present context, the term "heterocyclic system" is intended to include aromatic as well as non-aromatic ring moieties, which may be monocyclic, bicyclic or polycyclic, and contain in their ring structure at least one, such as one, two or three, nitrogen atom(s), and optionally one or more, such as one or two, other hetero atoms, e.g. sulpher or oxygen atoms. The heterocyclic system is preferably selected from pyrazole, pyridazine, triazine, indazole, phthalazine, cinnoline, pyrazolidine, pyrazoline, aziridine, dithiazine, pyrrol, imidazol, pyrazole, isoindole, indole, indazole, purine, pyrrolidine, pyrroline, imidazolidine, imidazoline, pyrazolidine, oxopyrazolidine, pyrazoline, piperidine, piperazine, indoline, isoindoline, or morpholine.

The term "halogen" is intended to include chlorine (Cl), fluorine (F), bromine (Br) and iodine (I).

The compounds of the present invention may have one or more asymmetric centres (chiral carbon atoms) and it is intended that stereoisomers, as separated, pure or partially purified stereoisomers or racemic mixtures thereof are included in the scope of the invention.

The compounds of the present invention may optionally be on a pharmaceutically acceptable salt form such as the pharmaceutically acceptable acid addition salts of compounds of formula I which include those prepared by reacting the compound of formula I with an inorganic or organic acid such as hydrochloric, hydrobromic, sulfuric, acetic, phosphoric, lactic, maleic, mandelic phthalic, citric, glutaric, gluconic, methanesulfonic, salicylic, succinic, tartaric, toluenesulfonic, trifluoracetic, sulfamic or fumaric acid and/or water.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences*, 1985 or in Remington: The Science and Practice of Pharmacy, 19th Edition (1995). The compositions may appear in conventional forms, for example capsules, tablets, aerosols, solutions, suspensions or topical applications.

The pharmaceutical carrier or diluent employed may be a conventional solid or liquid carrier.

Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:
Core:
Active compound (as free compound or salt thereof) 100 mg
Colloidal silicon dioxide (Aerosil) 1.5 mg
Cellulose, microcryst. (Avicel) 70 mg
Modified cellulose gum (Ac-Di-Sol) 7.5 mg
Magnesium stearate
Coating:
HPMC approx. 9 mg
*Mywaceft 9-40 T approx. 0.9 mg
*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage.

The dosage of the compounds according to this invention is suitably 0.1–500 mg/day, e.g. from about 5 to about 50 mg, such as about 10 mg per dose, when administered to patients, e.g. humans, as a drug.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pham aceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. The uses of growth hormone may be summarized as follows: stimulation of growth hormone release in the elderly, prevention of catabolic side effects of glucocorticoids, prevention and treatment of osteoporosis, treatment of chronic fatigue syndrom (CFS), treatment of acute fatigue syndrom and muscle loss following election surgery, stimulation of the immune system, acceleration of wound healing, accelerating bone fracture repair, accelerating complicated fractures, e.g. disctraction osteogenesis, treatment of wasting secondary to fractures, treatment of growth retardation, treating growth retardation resulting from renal failure or insufficiency, treatment of cardiomyopathy, treatment of chronic liver disease, treatment of thrombocytopenia, treatment of Crohn's disease, treatment of short bowel syndrome, treatment of chronic obstructive pulmonary disease (COPD), treatment of complications associated with transplantation, treatment of physiological short stature including growth hormone deficient children and short stature associated with chronic illness, treatment of obesity and growth retardation associated with obesity, treatment of anorexia, treating growth retardation associated with the Prader-Willi syndrome and Turner's syndrome; increasing the growth rate of a patient having partial growth hormone insensitivity syndrome; accelerating the recovery and reducing hospitalization of bum patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, treatment of cardiac failure or related vascular dysfunction, treatment of impaired cardiac function, treatment or prevention of myocardial infarction, lowering blood pressure, protection against ventricular dysfunction or prevention of reperfusion events; treatment of adults in chronic dialysis; attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, treatment of sarcopenia, treatment of wasting in connection with AIDS; improvement in muscle strength, mobility, maintenance of skin thickness, metabolic homeostasis, renal homeostasis in the frail elderly, stimulation of osteoblasts, bone remodelling and cartilage growth, regulation of food intake; stimulation of the immune system in companion animals and treatment of disorder of aging in companion animals, growth promoter in livestock and stimulation of wool growth in sheep, and treatment of metabolic syndrom (syndrome X). Moreover the compounds of formula I may be used in the treatment of insulin resistance, including NIDDM, in mammals, e.g. humans. It is furthermore believed that the present compounds of formula I may improve sleep quality and correct the relative hyposomatotropism of senescence due to high increase in REM sleep and a decrease in REM latency.

For the above indications the dosage will vary depending on the compound of formula I employed, on the mode of administration and on the therapy desired. However, generally dosage levels between 0.0001 and 100 mg/kg body weight daily, preferably from about 0.001 to about 50 mg/kg body weight daily, are administered to patients and animals to obtain effective release of endogenous growth hormone. Morever the compounds of formula I have no or substantially no side-effects, when administered in the above dosage levels, such side-effects being e.g. release of LH, FSH, TSH, ACTH, vasopressin, oxytocin, cortisol and/or prolactin. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula I, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals to increase their rate and extent of growth, and to increase milk and wool production or for the treatment of ailments.

A further use of growth hormone secretagogue compounds of formula I is in combination with other secretagogues such as GHRP (2 or 6), GHRH and its analogues, growth hormone and its analogues or somatomedins including IGF-1 and IGF-2.

Pharmacological Methods

Compounds of formula I may be evaluated in vitro for their efficacy and potency to release growth hormone in rat pituitary primary cultures, and such evaluation may be performed as described below.

The isolation of rat pituitary cells is a modification of O. Sartor et al., *Endocrinology* 116, 1985, pp. 952–957. Male albino Sprague-Dawley rats (250+/−25 grams) were purchased from Møllegaard, Lille Skensved, Denmark. The rats were housed in group cages (four animals/cage) and placed in rooms with 12 hour light cycle. The room temperature varied from 19–24° C. and the humidity from 30–60%.

The rats were decapitated and the pituitaries dissected. The neurointermediate lobes were removed and the remaining tissue was immediately placed in icecold isolation buffer (Gey's medium (Gibco 041-04030) supplemented with 0.25% D-glucose, 2% non-essential amino acids (Gibco 043-01140) and 1% bovine serum albumine (BSA) (Sigma A4503)). The tissue was cut into small pieces and transferred to isolation buffer supplemented with 3.8 mg/ml of trypsin (Worthington #3707 TRL-3) and 330 mg/ml of DNase (Sigma D-4527). This mixture was incubated at 70 rotations/min for 35 min at 37° C. in a 95/5% atmosphere of $O_2/CO_2$. The tissue was then washed three times in the above buffer. Using a standard pasteur pipette, the tissue was then aspirated into single cells. After dispersion, cells were filtered through a nylon filter (160 mm) to remove undigested tissue. The cell suspension was washed 3 times with isolation buffer supplemented with trypsin inhibitor (0.75 mg/ml, Worthington #2829) and finally resuspended in culture medium; DMEM (Gibco 041-01965) supplemented with 25 mM HEPES (Sigma H-3375), 4 mM glutamine (Gibco 043-05030H), 0.075% sodium bicarbonate (Sigma S-8875), 0.1% non-essential amino acid, 2.5% fetal calf serum (FCS, Gibco 011-06290), 3% horse serum (Gibco 034-06050), 10% fresh rat serum, 1 nM $T_3$ (Sigma T-2752) and 40 mg/l dexamethasone (Sigma D4902) pH 7.3, to a density of $2 \times 10^5$ cells/ml. The cells were seeded into microtiter plates (Nunc, Denmark), 200 ml/well, and cultured for 3 days at 37° C. and 8% $CO_2$.

Compound Testing

After culturing, the cells were washed twice with stimulation buffer (Hanks Balanced Salt Solution (Gibco 041-04020) supplemented with 1% BSA (Sigma A4503), 0.25% D-glucose (Sigma G-5250) and 25 mM HEPES (Sigma H-3375) pH 7.3) and preincubated for 1 hour at 37° C. The buffer was exchanged with 90 ml stimulation buffer (37° C.). Ten ml test compound solution was added and the plates were incubated for 15 min at 37° C. and 5% $CO_2$. The medium was decanted and analyzed for GH content in an rGH SPA test system.

All compounds were tested in doses ranging from 10 pM to 100 mM. A dose-response relation was constructed using the Hill equation (Fig P, Biosoft). The efficacy (maximal GH released, $E_{max}$) was expressed in % of the $E_{max}$ of GHRP-6. The potency ($EC_{50}$) was determined as the concentration inducing half maximal stimulation of the GH release.

Compounds of formula I may be evaluated for their metabolic stability using the procedure described below:

Compounds is dissolved at a concentration of 1 mg/ml in water. 25 ml of this solution is added to 175 ml of the respective enzyme-solution (resulting in an enzyme:substrate ratio (w/w) of approximately 1:5). The solution is left at 37° C. overnight. 10 ml of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4-10, Angiotensin 1-14 and Glucagon) have been included in the stability tests in order to verify the ability of the various solutions to degrade peptides.

Standard peptides (angiotensin 1-14, ACTH 4-10 and glucagon) were purchased from Sigma, Mo., USA)

Enzymes (trypsin, chymotrypsin, elastase aminopeptidase M and carboxypeptidase Y and B) were all purchased from Boehringer Mannheim GmbH (Mannheim, Germany).

Pancreatic enzyme mix: trypsin, chymotrypsin and elastase in 100 mM ammoniumbicarbonate pH 8.0 (all concentrations 0.025 mg/ml).

Carboxypeptidase mix: carboxypeptidase Y and B in 50 mM ammoniumacetate pH 4.5 (all concentrations 0.025 mg/ml).

Aminopeptidase M solution: aminopeptidase M (0.025 mg/ml) in 100 mM ammoniumbicarbonate pH 8.0

Mass spectrometric analysis was performed using two different mass spectrometers. A Sciex API III triple quadrupole LC-MS instrument (Sciex instruments, Thornhill, Ontario) equipped with an electrospray ion-source and a Bio-Ion 20 time-of-flight Plasma Desorption instrument (Bio-Ion Nordic AB, Uppsala, Sweden).

Quantification of the compounds (before and after degradation) was done on the API III instrument using single ion monitoring of the molecular ion in question with flow injection of the analyte. The liquid flow (MeOH:water 1:1) of 100 ml/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion).

Identification of degradation products furthermore involved the use of plasma desorption mass spectrometry (PDMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril: TFA separation gradient. The HPLC system used was HP1090M (Hewlett-Packard Company, Palo Alto, Calif.).

| Peptide derivative | MW/SIM ion (amu) | Carboxy peptidase mix | Pan. enzyme mix |
|---|---|---|---|
| Standards | | | |
| ACTH 4–10 | 1124.5/562.8 | + | − |
| Glucagon | 3483/871.8 | − | − |
| Insulin (B23–29) | 859.1/430.6 | | |

-continued

| Peptide derivative | MW/SIM ion (amu) | Carboxy peptidase mix | Pan. enzyme mix |
| --- | --- | --- | --- |
| Angiotensin 1–14 | 1760.1/881.0 | – | – |
| GHRP-2 | 817.4/409.6 | – | – |
| GHRP-6 | 872.6/437.4 | – | – |

+: Stable (less than 20% decrease in SIM signal after 24 h in degradation solution)
–: Unstable (more than 20% decrease in SIM signal after 24 h in degradation solution)

Any novel feature or combination of features described herein is considered essential to this invention.

Experimental

The process for preparing compounds of formula I and preparations containing them is further illustrated in the following examples, which however, are not to be construed as limiting.

The structures of the compounds are confirmed by either High Performance Liquid Chromatography (HPLC), nuclear magnetic resonance (NMR, Bruker 400 MHz) or Liquid Chromatography-Mass Spectrometry (LC-MS). NMR shifts (δ) are given in parts per million (ppm) and only selected peaks are given. mp is melting point and is given in °C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se. The methanollammonia solution used is a 10% ammonia solution in methanol.

HPLC (Method A1): The RP-HPLC analysis was performed using UV detection at 214 nm and a Hibar LiChrosorb RP-18 (5 uM) 250-4 (Merck) column, which was eluted at 1 ml/minute. Two solvent systems were used: Solvent system I: 0.1% Trifluoroacetic acid in acetonitrile. Solvent system II: 0.1% Trifluoroacetic acid in water. The column was equilibrated with a mixture composed of 20% of solvent system I and 95% of solvent system II. After injection of the sample a gradient of 20% to 80% of solvent system I in solvent system II was run over 30 minutes. The gradient was then extended to 100% of solvent system I over 5 minutes followed by isocratic elution with 100% of this system for 5 minutes. The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% acetonitrile in a buffer consisting of 0.1 M ammonium sulfate, which was adjusted to pH 2.5 with 4M sulfuric acid. After injection the sample was eluted by a gradient of 5% to 60% acetonitrile in the same buffer during 50 min.

HPLC (Method B1): The RP-HPLC analysis was performed using UV detection at 214 nm and a Hibar LiChrosorb RP-18 (5 uM) 250-4 (Merck) column, which was eluted at 1 ml/minute. Two solvent systems were used: Solvent system I: 0.1% Trifluoroacetic acid in acetonitrile. Solvent system II: 0.1% Trifluoroacetic acid in water. The column was equilibrated with a mixture composed of 20% of solvent system I and 95% of solvent system II. After injection of the sample a gradient of 20% to 80% of solvent system I in solvent system II was run over 30 minutes. The gradient was then extended to 100% of solvent system I over 5 minutes followed by isocratic elution with 100% of this system for 5 minutes. The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% (acetonitrile+0.1% TFA) in an aqueous solution of TFA in water (0.1%). After injection the sample was eluted by a gradient of 5% to 60% (acetonitrile+0.1% TFA) in the same aqueous buffer during 50 min.

HPLC (Method H8): The HPLC analyses was performed using a Waters® millenium system using a Water® 3 mm×150 mm 3.5 m C-18 Symmetry column. The column was heated to 42° C. and eluted with a linear gradient of 5–90% acetonitrile, 85–0% water and 10% trifluoroacetic acid (0.5%) in water in 15 minutes at a flowrate of 1 min/min.

The LC-MS analyses were performed on a PE Sciex API 100 LC/MS System using a Waters® 3 mm×150 mm 3.5 m C-18 Symmetry column and positive ionspray with a flow rate of 20 ml/min. The column was eluted with a linear gradient of 5–90% acetonitrile, 85–0% water and 10% trifluoroacetic acid (0.1%)/water in 15 min at a flow rate of 1 ml/min.

EXAMPLE 1

(2E)-5-Amino-5-methylhex-2-enoic acid N-((1R)-1-N-[(1R)-2-(N'-acetylhydrazino)-1-benzyl-2-oxoethyl]-N-methylcarbamoyl)-2-(2-naphthyl)ethyl)-N-methylamide

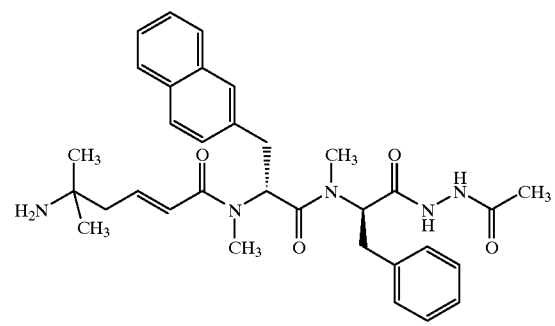

N'-Acetylhydrazinecarboxylic acid tert-butyl ester

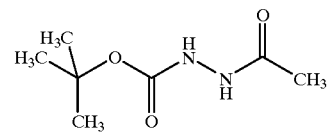

To a solution of tert-butyl carbazate (1.0 g, 7.6 mmol) and pyridine (3.1 ml) in methylene chloride (5 ml) was slowly added acetic acid anhydride (1.5 ml) and the mixture was stirred overnight. The mixture was added to methylene chloride (50 ml) and washed with water (2×10 ml) and brine (10 ml) and dried (MgSO$_4$), filtered and concentrated in vacuo to give 0.95 g of N'-acetylhydrazinecarboxylic acid tert-butyl ester as a yellow oil.

LC-MS: $R_t$=5.39, m/z=349.6 (m+1); $^1$H NMR (CDCl$_3$) Selected peaks: δ 1.5 (s, 9H, (CH$_3$)$_3$C—O); 2.05 (s, 3H, CH$_3$CO).

N-[(1R)-2-(N'-Acetylhydrazino)-1-benzyl-2-oxoethyl]-N-methylcarbamic acid tert-butyl ester

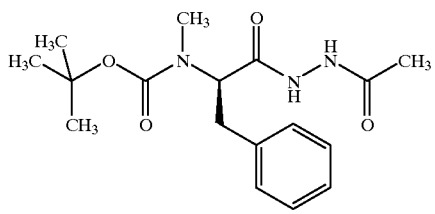

N'-Acetylhydrazinecarboxylic acid tert-butyl ester(0.95 g, 5.45 mmol) was dissolved in methylene chloride (10 ml) and trifluoroacetic acid (10 ml) was added and the mixture was stirred at room temperature for 1 h. The mixture was concentrated in vavuo and stripped three times with methylene chloride to give 1.0 g of acetic acid hydrazide. Then (2R)-2-(tert-butoxycarbonylmethylamino)-3-phenyl propionic acid (0.76 g, 2.73 mmol) was dissolved in a mixture of dimethyl formamide (3 ml) and methylene chloride (6 ml) and a mixture of 1-hydroxy-7-azabenzotriazole (0.45 g, 3.28 mmol) and 1-ethyl-3-(3-dimethylaminopropyl)carbodiimide hydrochloride (0.62 g, 3.28 mmol) was added and stirred for 20 min. Then a mixture of acetic acid hydrazide (1.0 g, 5.45 mmol) and diisopropylethylamine (1.87 ml) was added and the mixture was stirred overnight. Ethyl acetate (50 ml) was added and the mixture was washed with water (50 ml). The aqueous layer was extracted with ethyl acetate (3×50 ml) and the combined organic layers were washed with water (2×50 ml) and brine (50 ml) and dried (MgSO$_4$), filtered, concentrated to an oil, and chromatographed on silica (40 g) with heptane:ethyl acetate (1:1) to give 0.81 g of N-[(1R)-2-(N'-acetylhydrazino)-1-benzyl-2-oxoethyl]-N-methylcarbamic acid tert-butyl ester as a yellow oil.

LC-MS R$_t$=9.34, m/z=336.4 (m+1); HPLC: R$_t$=10.17 min (H8); $^1$H NMR (CDCl$_3$) Selected peaks: δ 1.32+1.40 (2s, 3H, (CH$_3$)$_3$C—O, rotamere); 2.05 (s, 3H, COCH$_3$); 2.78 (s, 3H, N—CH$_3$).

N-(1R)-1-(N-[(1R)-2-(N'-Acetylhydrazino)-1-benzyl-2-oxoethyl]-N-methylcarbamoyl)-2-(2-naphthyl)ethyl)-N-methylcarbamic acid tert-butyl ester

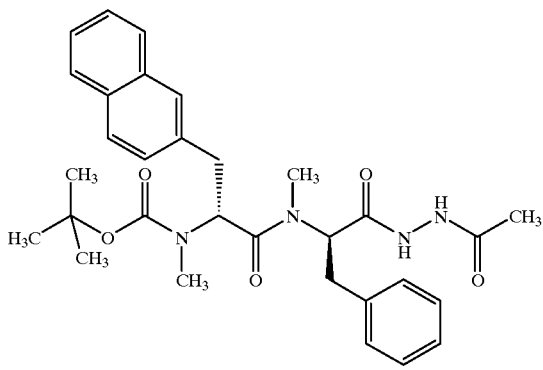

N-[(1R)-2-(N'-Acetylhydrazino)-1-benzyl-2-oxoethyl]-N-methylcarbamic acid tert-butyl ester (0.81 g, 2.42 mmol) was dissolved in methylene chloride (5 ml) and trifluoroacetic acid (5 ml) was added and the mixture was stirred for 30 min at room temperature. The mixture was concentrated in vacuo and stripped three times with methylene chloride and the remaining oil was chromatographed on silica (40 g) with methylene chloride:(methanol/ammonia) (9:1) to give 0.41 g of acetic acid N'-((2R)-2-(methylamino)-3-phenylpropionyl)hydrazide as an amorphous powder.

Then (2R)-2-(N-tert-butoxycarbonyl-N-methylamino)-3-(2-naphthyl)propionic acid (0.63 g, 1.92 mmol) was dissolved in methylene chloride (10 ml) and a mixture of 1-hydroxy-7-azabenzotriazole (0.26 g, 1.92 mmol) and 1-ethyl-3-(3-dimethylaminopropyl)carbodiimide hydrochloride (0.37 g, 1.92 mmol) was added and stirred for 30 min. A mixture of acetic acid N'-((2R)-2-(methylamino)-3-phenylpropionyl)hydrazide (0.41 g, 1.74 mmol) and DIEA (0.39 ml) was added and the mixture was stirred overnight.

Methylene chloride (50 ml) was added and the mixture was washed with water (50 ml). The organic layer was washed with aqueous sodium bicarbonate (10 ml) and brine (50 ml) and dried (MgSO$_4$), filtered, concentrated to an oil, and chromatographed on silica (40 g) with heptane:ethyl acetate (1:4) to give 0.59 g of N-((1R)-1-(N-[(1R)-2-(N'-acetylhydrazino)-1-benzyl-2-oxoethyl]-N-methylcarbamoyl)-2-(2-naphthyl)ethyl)-N-methylcarbamic acid tert-butyl ester as an oil.

LC-MS R$_t$=13.68 min, m/z=547.2 (m+1); HPLC: R$_t$=13.53 min (H8).

(2E)-5-Amino-5-methylhex-2-enoic acid N-((1R)-1-(N-[(1R)-2-(N'-acetylhydrazino)-1-benzyl-2-oxoethyl]-N-methylcarbamoyl)-2-(2-naphthyl)ethyl)-N-methylamide

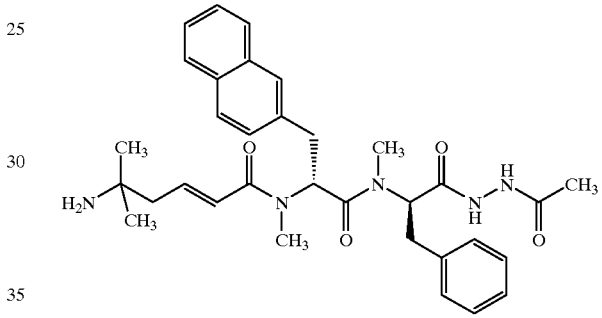

To a solution of N-((1R)-1-(N-[(1R)-2-(N'-acetylhydrazino)-1-benzyl-2-oxoethyl]-N-methylcarbamoyl)-2-(2-naphthyl)ethyl)-N-methylcarbamic acid tert-butyl ester (0.59 g, 1.08 mmol) in methylene chloride (5 ml) was added trifluoroacetic acid (5 ml) at 0° C. and stirred for 90 min. The mixture was concentrated in vacuo and stripped three times with methylene chloride. The obtained oil was dissolved in methanovammonia (2 ml) and added methylene chloride (20 ml) and silica gel (5 g) and concentrated in vacuo. The obtained powder was extracted by filtration with methylene chloride (100 ml) and methylene chloride:(methanol/ammonia) (9:1) and the combined extracts were concentrated in vacuo to 0.41 g of crude product as a foam.

Then (2E)-5-(tedt-butyloxycarbonylamino)-5-methylhex-2-enoic acid (0.21 g, 0.89 mmol) was dissolved in methylene chloride (10 ml) and a mixture of 1-hydroxy-7-azabenzotriazole (0.13 g, 0.98 mmol) and 1-ethyl-3-(3-dimethylaminopropyl)-carbodiimide hydrochloride (0.17 g, 0.89 mmol) was added and stirred for 30 min. Then a mixture of the above crude product (0.40 g, 0.89 mmol) and diisopropylethylamine (0.20 ml) was added and the mixture was stirred overnight.

Methylene chloride (50 ml) was added and the mixture was washed with water (10 ml). The organic layer was washed with aqueous sodium bicarbonate (10 ml) and brine (50 ml), dried (MgSO$_4$), filtered, concentrated to 0.42 g of a tan foam. The foam was dissolved in methylene chloride (5 ml), cooled to 0° C. and trifluoroacetic acid (5 ml) was added and the mixture was stirred for 45 min. The reaction mixture was quenched with methylene chloride 50 ml) and water (10 ml) and titrated to pH~7 with solid sodium bicarbonate. The organic layer was separated and washed with water (10 ml), dried (MgSO₄), filtered and concentrated in vacuo.

The obtained product was dissolved in acetonitrile/water 1:20 (10 ml) and applied to a C-18 Sep-Pak Classic© cartridge (2.0 g, purchased from Waters™), which had been prewashed with acetonitrile (100 ml) and water (100 ml). Then a gradient of an eluent consisting of water/acetonitrile/ trifluoroacetic acid (10, 15, 20 and 25% acetonitrile in water/0.1% trifluoroacetic acid) was run through the Sep-Pak© (2 g). The relevant fractions were combined and lyophilised to 0.19 g of the trifluoroacetic acid salt of (2E)-5-amino-5-methylhex-2-enoic acid N-((1R)-1-(N-[(1R)-2-(N'-acetylhydrazino)-1-benzyl-2-oxoethyl]-N-methylcarbamoyl)-2-(2-naphthyl)ethyl)-N-methylamide as a white amorphous powder.

LC-MS: R$_t$=9.21 min, m/z=572.4 (m+1); HPLC: R$_t$=26.45 min (A1), R$_t$=28.40 (B1).

EXAMPLE 2

(2E)-5-Amino-5-methylhex-2-enoic acid N-((1R)-1-(N-[(1R)-2-(N'-acetyl-N-methylhydrazino)-1-benzyl-2-oxoethyl]-N-methylcarbamoyl)-2-(2-naphthyl)ethyl)-N-methylamide

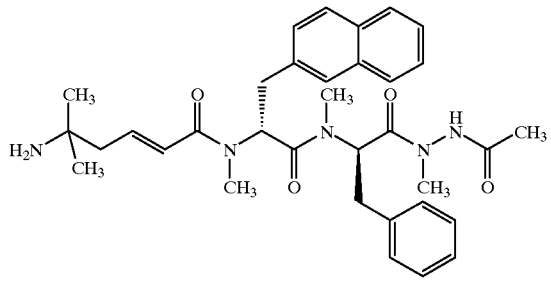

N'-Acetyl-N-methylhydrazinecarboxylic acid tert-butyl ester

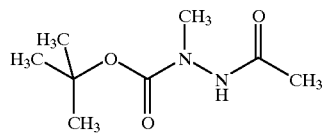

To a solution of N-methylhydrazinecarboxylic acid tert-butyl ester (0.62 g, 4.20 mmol) in methylene chloride (10 ml) was added acetic acid anhydride (0.79 ml, 8.40) and pyridine (1.36 ml, 16.80 mmol) and the mixture was stirred overnight. Then methylene chloride (50 ml) was added and the mixture was washed with water (3×10 ml), dried (MgSO₄), filtered and concentrated in vacuo to give 0.32 g (41%) of N'-acetyl-N-methylhydrazinecarboxylic acid tert-butyl ester as an oil.

¹H NMR (CDCl₃) Selected peaks: δ 1.45+1.48 (2 s, 9H, (CH₃)₃C—O, rotamere); 1.98 (s, 3H, COCH₃); 3.14+3.17 (2 s, 3H, N—CH₃, rotamere).

Acetic acid N'-methylhydrazide

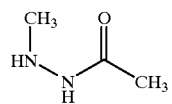

To a solution of N'-acetyl-N-methylhydrazinecarboxylic acid tert-butyl ester (0.3 g, 1.59 mmol) in methylene chloride (2 ml) was added trifluoroacetic acid (2 ml) and the mixture was stirred for 60 min. The mixture was concentrated in vacuo and stripped three times with methylene chloride to give 0.32 g (100%) of acetic acid N'-methylhydrazide trifluoroacetic acid as a thin oil.

¹H NMR (CDCl₃): δ 2.13 (s, 3H, COCH₃); 2.98 (s, 3H, N—CH₃).

N-[(1R)-2-(N'-Acetyl-N-methylhydrazino)-1-benzyl-2-oxoethyl]-N-methylcarbamic acid tert-butyl ester

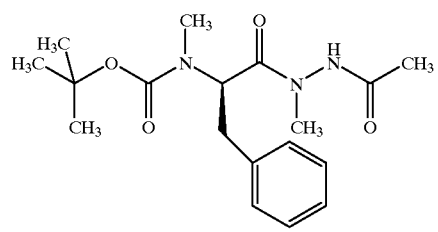

To a solution of (2R)-2-(N-tert-butoxycarbonyl-N-methylamino)-3-phenylpropionic acid (0.27 g, 0.96 mmol) in methylene chloride (10 ml) was added 1-hydroxy-7-azabenzotriazole (0.13 g, 0.96 mmol) and 1-ethyl-3-(3-dimethylaminopropyl)-carbodiimide hydrochloride (0.18 g, 0.96 mmol) and the mixture was cooled to 0° C. Then acetic acid N'-methylhydrazide (0.19 g, 0.96 mmol) and diisopropylethylamine (0.41 ml, 2.40 mmol) were added and the mixture was stirred at room temperature overnight. Then methylene chloride (50 ml) was added and the mixture was washed with water (10 ml), saturated sodium bicarbonate (10 ml), brine (10 ml), dried (MgSO₄), filtered and concentrated in vacuo to give 0.35 g (125%) of crude N-[(1R)-2-(N'-acetyl-N-methylhydrazino)-1-benzyl-2-oxoethyl]-N-methylcarbamic acid tert-butyl ester as a colourless oil.

LC-MS: R$_t$=10.29 min, m/z=350.4 (m+1); HPLC: R$_t$=10.77 min (H8).

Acetic acid N'-methyl-N'-((2R)-2-(methylamino)-3-phenylpropionyl)hydrazide

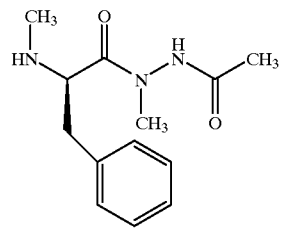

To a solution of N-[(1R)-2-(N'-acetyl-N-methylhydrazino)-1-benzyl-2-oxoethyl]-N-methylcarbamic acid tert-butyl ester (0.35 g, 1.00 mmol) in methylene chloride (2 ml) was added trifluoroacetic acid (2 ml) and the mixture was stirred for 30 min. The mixture was concentrated in vacuo and stripped three times with methylene chloride and chromatographed on silca gel (40 g) with methylene chloride:(methanol/ammonia) (9:1) to give 110 mg (44%) of acetic acid N'-methyl-N'-((2R)-2-(methylamino)-3-phenylpropionyl)hydrazide as an oil.

¹H NMR (CDCl₃): δ 1.85 (s, 3H, COCH₃); 2.25 (s,3H, N—CH₃); 3.05 (s, 3H, N—CH₃).

(2R)-N-[(1R)-2-N'-Acetyl-N-methylhydrazino)-1-benzyl-2-oxoethyl]-N-methyl-2-methylamino)-3-(2-naphthyl)propionamide

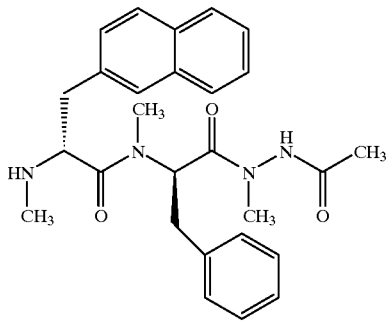

To a solution of 2(R)-(N-tert-butoxycarbonyl-N-methylamino)-3-(2-naphthyl)propionic acid (0.18 g, 0.53 mmol) in methylene chloride (5 ml) was added 1-hydroxy-7-azabenzotriazole (0.072 g, 0.53 mmol) and 1-ethyl-3-(3-dimethylaminopropyl)carbodiimide hydrochloride (0.10 g, 0.53 mmol) and the mixture was cooled to 0° C. Then acetic acid N'-methyl-N'-((2R)-2-(methylamino)-3-phenylpropionyl)hydrazide (0.11 g, 0.44 mmol) and diisopropylethylamine (0.098 ml, 0.57 mmol) were added and the mixture was stirred at room temperature overnight. Then methylene chloride (50 ml) was added and the mixture was washed with water (10 ml), saturated sodium bicarbonate (10 ml), brine (10 ml), dried (MgSO₄), filtered, concentrated in vacuo and chromatographed on silica gel (40 g) with ethyl acetate to give 0.14 g (57%) of N-((1R)-1-(N-[(1R)-2-(N'-acetyl-N-methylhydrazino)-1-benzyl-2-oxoethyl]-N-methylcarbamoyl)-2-(2-naphthyl)ethyl)-N-methylcarbamic acid tert-butyl ester as a colourless oil.

To a solution of N-((1R)-1-(N-[(1R)-2-(N'-acetyl-N-methylhydrazino)-1-benzyl-2-oxoethyl]-N-methylcarbamoyl)-2-(2-naphthyl)ethyl)-N-methylcarbamic acid tert-butyl ester (0.14 g, 0.25 mmol) in methylene chloride (2 ml) at 0° C. was added trifluoroacetic acid (2 ml) and the mixture was stirred for 90 min. Then methylene chloride (50 ml) and saturated sodium bicarbonate (5 ml) was added and the mixture was titrated with solid sodium bicarbonate until pH=7. The water layer was separated and extracted with methylene chloride (20 ml) and the combined organic layers were washed with brine (10 ml), dried (MgSO₄), filtered and concentrated in vacuo to give 0.10 g (87%) of (2R)-N-[(1R)-2-(N'-acetyl-N-methylhydrazino)-1-benzyl-2-oxoethyl]-N-methyl-2-(methylamino)-3-(2-naphthyl)propionamide as an oil.

¹H NMR (CDCl₃) Selected peaks: δ 1.68 (s, 3H, N—CH₃); 1.98 (s, 3H, COCH₃).

(2E)-5-Amino-5-methylhex-2-enoic acid N-((1R)-1-(N-[(1R)-2-(N'-acetyl-N-methylhydrazino)-1-benzyl-2-oxoethyl]-N-methylcarbamoyl)-2-(2-naphthyl)ethyl)-N-methylamide

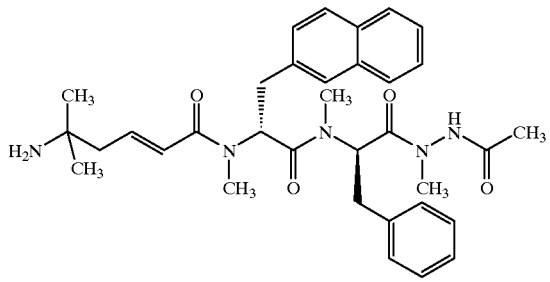

To a solution of (2E)-5-(tert-butyloxycarbonylamino)-5-methylhex-2-enoic acid (0.066 g, 0.27 mmol) in methylene chloride (5 ml) was added 1-hydroxy-7-azabenzotriazole (0.037 g, 0.27 mmol) and 1-ethyl-3-(3-dimethylaminopropyl)carbodiimide hydrochloride (0.052 g, 0.27 mmol) and the mixture was cooled to 0° C. Then (2R)-N-[(1R)-2-(N'-acetyl-N-methylhydrazino)-1-benzyl-2-oxoethyl]-N-methyl-2-(methylamino)-3-(2-naphthyl)propionamide (0.10 g, 0.22 mmol) and diisopropylethylamine (0.049 ml, 0.29 mmol) were added and the mixture was stirred at room temperature overnight. Then methylene chloride (50 ml) was added and the mixture was washed with water (10 ml), saturated sodium bicarbonate (10 ml), brine (10 ml), dried (MgSO₄), filtered and concentrated in vacuo. The product was chromatographed on silica gel (40 g) with heptane:ethyl acetate (1:1) to give 0.10 g (66%) of ((3E)-4-[N-((1R)-1-(N-[(1R)-2-(N'-acetyl-N-methylhydrazino)-1-benzyl-2-oxoethyl]-N-methylcarbamoyl)-2-(2-naphthyl)ethyl)-N-methylcarbamoyl]-1,1-dimethylbut-3-enyl)carbamic acid tert-butyl ester as a colourless oil.

A solution of ((3E)-4-[N-((1R)-1-(N-[(1R)-2-(N'-acetyl-N-methylhydrazino)-1-benzyl-2-oxoethyl]-N-methyicarbamoyl)-2-(2-naphthyl)ethyl)-N-methylcarbamoyl]-1,1-dimethylbut-3-enyl)carbamic acid tert-butyl ester (0.1 g, 0.146 mmol) in methylene chloride (2 ml) was cooled to 0° C. and trifluoroacetic acid (2 ml) was added and the misture was stirred for 30 min. Then methylene chloride (50 ml) and saturated sodium bicarbonate (5 ml) was added and the mixture was titrated with solid sodium bicarbonate until pH=7. The water layer was separated and extracted with methylene chloride (20 ml) and the combined organic layers were washed with brine (10 ml), dried (MgSO₄), filtered and concentrated in vacuo. The obtained product was dissolved in acetonitrile/water 1:20 (10 ml) and applied to a C-18 Sep-Pak Classic© cartridge (2.0 g, purchased from Waters™), which had been prewashed with acetonitrle (100 ml) and water (100 ml). Then a gradient of an eluent consisting of water/acetonitrile/trifluoroacetic acid (10, 50, and 70% acetonitrile in water/0.1% trifluoroacetic acid) was run through the Sep-Pak© (2 g). The relevant fractions were combined and lyophilised to 0.054 g (53%) of the trifluoroacetic acid salt of (2E)-5-amino-5-methylhex-2enoic acid N-((1R)-1-(N-[(1R)-2-(N'-acetyl-N-methylhydrazino)-1-benzyl-2-oxoethyl]-N-methylcarbamoyl)-2-(2-naphthyl)ethyl)-N-methylamide as a white amorphous powder.

LC-MS: R$_t$=8.74 min, m/z=586.4 (m+1); HPLC: R$_t$=29.53 (A1); R$_t$=31.35 (B1); ¹H NMR (DMSO) Selected peaks: δ 1.05 (s, 6H, C—(CH₃)₂); 1.77 (s, 3H, COCH₃); 6.2 (d, 1H, C=CH—CO); 6.3 (m, 1H, CH₂—CH=C).

EXAMPLE 3

(2E)-5-Amino-5-methylhex-2-enoic acid N-((1R)-1-(N-[(1R)-2-(N'-acetyl-N'-methylhydrazino)-1-benzyl-2-oxoethyl]-N-methylcarbamoyl)-2-(2-naphthyl)ethyl)-N-methylamide

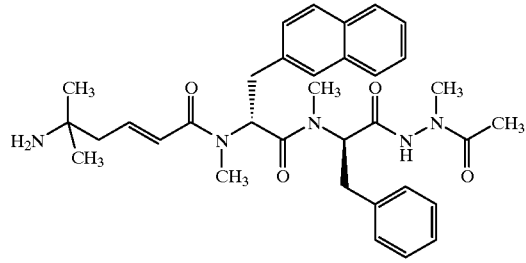

N'-Benzylidenehydrazinecarboxylic acid tert-butylester

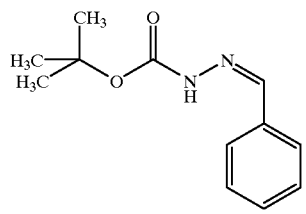

To a solution of tert-butyl carbazate (10.0 g, 75.64 mmol) in 99% ethanol (100 ml) was added benzaldehyde (7.64 ml, 75.64 mmol) and the mixture was stirred for 60 min. The mixture was cooled to 0° C., filtered and the precipitate was washed with cold ethanol and dried to give 13.47 g (81%) of N'-benzylidenehydrazinecarboxylic acid tert-butylester as white crystals.

Mp. 184–186° C.; $^1$H NMR (CDCl$_3$): δ 1.52 (s, 9H, (CH$_3$)C); 7.34–7.92 (m, 7H, arom).

N'-Benzylidene-N-methylhydrazinecarboxylic acid tert-butyl ester

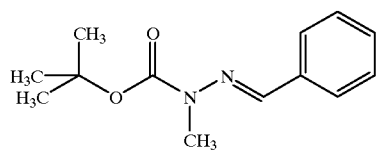

To a solution of N'-benzylidenehydrazinecarboxylic acid tert-butylester (2.0 g, 9.07 mmol) in anhydrous tetrahydrofuran (20 ml) was added methyl iodide (4.54 ml, 72.6 mmol) and the solution was cooled to 0° C. Sodium hydride (60% dispersion in mineral oil, 1.09 g, 27.2 mmol) was slowly added and the mixture was stirred at room temperature for 3 days. The tetrahydrofuran (50 ml) was added and the mixture was filtered. The filtrate was concentrated in vacuo and chromatographed on silica (100 g) with heptan:ethyl acetate (1:1) to give 1.97 g (93%) of N'-benzylidene-N-methylhydrazinecarboxylic acid tert-butyl ester as a yellow oil.

$^1$H NMR (CDCl$_3$) Selected peaks: δ 1.58 (s, 9H, (CH$_3$)$_3$C); 3.34 (s, 3H, N—CH$_3$).

N-Methyl-hydrazinecarboxylic acid tert-butyl ester

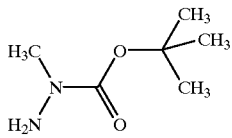

To a solution of of N'-benzylidene-N-methylhydrazinecarboxylic acid tert-butyl ester (1.97 g, 8.41 mmol) in anhydrous tetrahydrofuran (50 ml) was added palladium on carbon (10%, 0.2 g) and the mixture was exposed to hydrogen. After a consumption of 260 ml of hydrogen the mixture was filtered though celite and concentrated to 1.25 g (100%) of N-methyl-hydrazinecarboxylic acid tert-butyl ester.

$^1$H NMR (CDCl$_3$) Selected peaks: δ 1.5 (s, 9H, (CH$_3$)$_3$C—O) 3.05 (s, 3H, N—CH$_3$).

N-Methyl-N'-((2R)-2-(methylamino)-3-phenylpropionyl)hydrazinecarboxylic acid tert-butyl ester

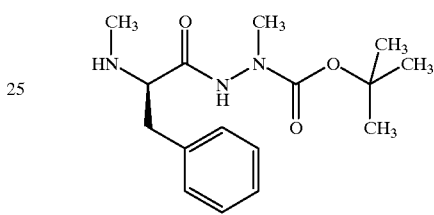

To a solution of (2R)-2-(N-(((9H-fluoren-9-yl)methoxy)carbonyl)-N-methylamino)-3-phenylpropionic acid (0.6 g, 1.5 mmol) in methylene chloride (10 ml) was added 1-hydroxy-7-azabenzotriazole (0.22 g, 1.65 mmol) and 1-ethyl-3-(3-dimethylaminopropyl)carbodiimide hydrochloride (0.29 g, 1.50 mmol) and the mixture was cooled to 0° C. Then N-methyl-hydrazinecarboxylic acid tert-butyl ester (0.22 g, 1.50 mmol) and diisopropylethylamine (0.33 ml, 1.95 mmol) were added and the mixture was stirred at room temperature overnight. Then methylene chloride (20 ml) was added and the mixture was washed with water (20 ml), saturated sodium bicarbonate (20 ml), brine (20 ml), dried (MgSO$_4$), filtered and concentrated in vacuo. The product was chromatographed on silica (40 g) with heptane:ethyl acetate (1:1) to give 0.65 g (82%) of N'-((2R)-2-[N-(((9H-fluoren-9-yl)methoxy)carbonyl)-N-methylamino]-3-phenylpropionyl)-N-methylhydrazinecarboxylic acid tert-butyl ester ester as a white foam.

To a solution of N'-((2R)-2-[N-(((9H-fluoren-9-yl)methoxy)carbonyl)-N-methylamino]-3-phenylpropionyl)-N-methylhydrazinecarboxylic acid tert-butyl ester (0.65 g, 1.23 mmol) in methylene chloride (4 ml) was added tris(2-aminoethyl)amine (4 ml) and the mixture was stirred at room temperature for 60 min. Then methylene chloride (50 ml) was added and the mixture was washed with brine (2×20 ml), phosphate buffer (pH=6, 2×20 ml), water (20 ml), brine (10 ml), dried (MgSO$_4$), filtered and concentrated in vacuo to give 0.34 g (90%) of N-methyl-N'-((2R)-2-(methylamino)-3-phenylpropionyl)hydrazinecarboxylic acid tert-butyl ester as a yellow oil.

$^1$H NMR (CDCl$_3$) Selected peaks: δ 1.35+1.4 (s, 9H, (CH$_3$)$_3$C—O, rotamere) 2.2 (s, 3H, N—CH$_3$) 2.5 (s, 3H, N—CH$_3$).

N'-[(2R)-2-(N-(2R)-2-[N-(((9H-Fluoren-9-yl)methoxy)carbonyl)-N-methylamino]-3-(2-naphthyl)propionyl)-N- methylamino)-3-phenylpropionyl]-N-methylhydrazinecarboxylic acid tert-butyl ester

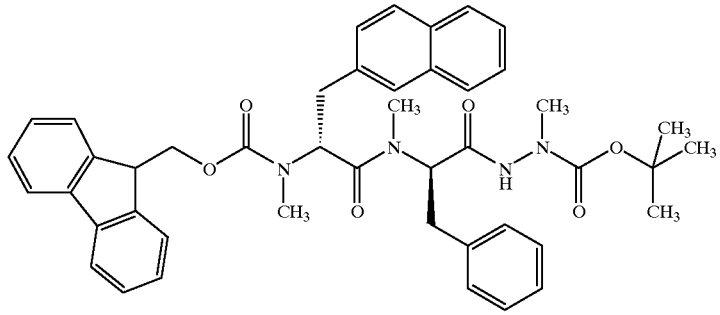

To a solution of (2R)-2-[N-(9H-fluoren-9-ylmethoxycarbonyl)-N-methylamino]-3-naphthalen-2-ylpropionic acid (0.6 g, 1.33 mmol) in methylene chloride (10 ml) was added 1-hydroxy-7-azabenzotriazole (0.18 g, 1.33 mmol) and 1-ethyl-3-(3-dimethylaminopropyl) carbodiimide hydrochloride (0.25 g, 1.33 mmol) and the mixture was cooled to 0° C. Then N-methyl-N'-((2R)-2-(methylamino)-3-phenylpropionyl)hydrazinecarboxylic acid tert-butyl ester (0.34 g, 1.11 mmol) and diisopropylethylamine (0.25 ml, 1.44 mmol) were added and the mixture was stirred at room temperature overnight. Then methylene chloride (50 ml) was added and the mixture was washed with water (10 ml), saturated sodium bicarbonate (10 ml), brine (10 ml), dried (MgSO$_4$), filtered and concentrated in vacuo. The product was chromatographed on silica (40 g) with heptane:ethyl acetate (2:1) to give 0.53 g (64%) of N'-[(2R)-2-(N-((2R)-2-[N-(((9H-fluoren-9-yl)methoxy)carbonyl)-N-methylamino]-3-(2-naphthyl)propionyl)-N-methylamino)-3-phenylpropionyl]-N-methylhydrazinecarboxylic acid tert-butyl ester as a colourless oil.

$^1$H NMR (DMSO) Selected peaks: δ 1.25+1.55 (2 s, 9H, (CH$_3$)$_3$C—O, rotamere) 2.3+2.35 (2 s, 3H, N—CH$_3$, rotamere) 2.65+2.68 (2 s, 3H, N—CH$_3$, rotamere) 2.95+3.0 (2 s, 3H, N—CH$_3$, rotamere).

N-Methyl-N-((1R)-1-(N-methyl-N-[(1R)-1-(N'-methylhydrazinocarbonyl)-2-phenylethyl]carbamoyl)-2-(2-naphthyl)ethyl)carbamic acid ((9H-fluoren-9-yl)methyl) ester

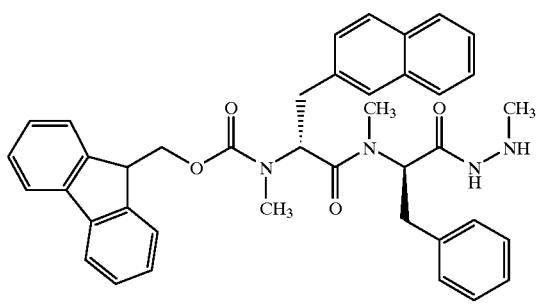

To a solution of N'-[(2R)-2-(N-((2R)-2-[N-(((9H-fluoren-9-yl)methoxy)carbonyl)-N-methylamino]-3-(2-naphthyl)propionyl)-N-methylamino)-3-phenylpropionyl]-N-methylhydrazinecarboxylic acid tert-butyl ester (0.27 g, 0.36 mmol) in methylene chloride (2 ml) at 0° C. was added trifluoroacetic acid (2 ml) and the mixture was stirred for 90 min. Then methylene chloride (50 ml) and saturated sodium bicarbonate (5 ml) was added and the mixture was titrated with solid sodium bicarbonate until pH=7. The water layer was separated and extracted with methylene chloride (20 ml) and the combined organic layers were washed with brine (10 ml), dried (MgSO$_4$), filtered and concentrated in vacuo to give 0.18 g (78%) of N-methyl-N-((1R)-1-(N-methyl-N-[(1R)-1-(N'-methylhydrazinocarbonyl)-2-phenylethyl]carbamoyl)-2-(2-naphthyl)ethyl)carbamic acid ((9H-fluoren-9-yl)methyl) ester as white amorphous powder.

LC-MS: R$_t$=14.03 min, m/z=641.4 (m+1); HPLC: R$_t$=13.80 min (H8).

N((1R)-1-(N-[(1R)-2-(N'-Acetyl-N'-methylhydrazino)-1-benzyl-2-oxoethyl]-N-methylcarbamoyl)-2-(2-naphthyl)ethyl)-N-methylcarbamic acid ((9H-fluoren-9-yl)methyl) ester

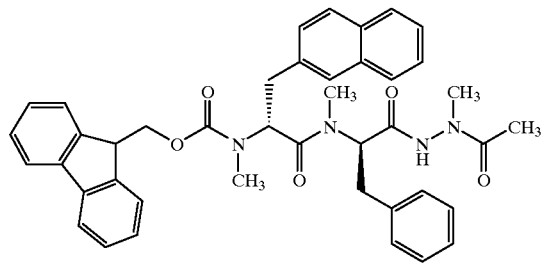

To a solution of N-methyl-N-((1R)-1-(N-methyl-N-[(1R)-1-(N'-methylhydrazinocarbonyl)-2-phenylethyl]carbamoyl)-2-(2-naphthyl)ethyl)carbamic acid ((9H-fluoren-9-yl)methyl) ester (0.18 g, 0.28 mmol) in methylene chloride (2 ml) was added acetic acid anhydride (0.053 ml) and pyridine (0.027 ml) and the mixture was stirred overnight. The mixture was concentrated in vacuo and stripped three times with methylene chloride to give 0.21 g (110%) of N-((1R)-1-(N-[(1R)-2-(N'-acetyl-N'-methylhydrazino)-1-benzyl-2-oxoethyl]-N-methylcarbamoyl)-2-(2-naphthyl)ethyl)-N-methylcarbamic acid ((9H-fluoren-9-yl)methyl) ester as a colourless oil.

LC-MS: R$_t$=16.48 min, m/z=683.0 (m+1); HPLC: R$_t$=15.81 min (H8).

(2R)-N-[(1R)-2-(N'-Acetyl-N'-methylhydrazino)-1-benzyl-2-oxoethyl]-N-methyl-2-(methylamino)-3-(2-naphthyl)propionamide

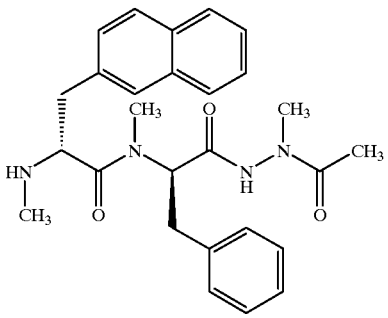

To a solution of N-((1R)-1-(N-[(1R)-2-(N'-acetyl-N'-methylhydrazino)-1-benzyl-2-oxoethyl]-N-methylcarbamoyl)-2-(2-naphthyl)ethyl)-N-methylcarbamic acid ((9H-fluoren-9-yl)methyl) ester (0.21 g, 0.31 mmol) in methylene chloride (4 ml) was added tris(2-aminoethyl) amine (4 ml) and the mixture was stirred for 60 min. Then methylene chloride (50 ml) was added and the mixture was washed with brine (2×20 ml), phosphate buffer (pH=6, 2×20 ml), water (20 ml), brine (10 ml), dried (MgSO$_4$), filtered and concentrated in vacuo to give 0.13 g (92%) of (2R)-N-[(1R)-2-(N'-acetyl-N'-methylhydrazino)-1-benzyl-2-oxoethyl]-N-methyl-2-(methylamino)-3-(2-naphthyl) propionamide as a colourless oil.

LC-MS: R$_t$=8.57 min, m/z=461.2 (m+1)

(2E)-5-Amino-5-methylhex-2-enoic acid N-((1R)-1-N-[(1R)-2-(N'-acetyl-N'-methylhydrazino)-1-benzyl-2-oxoethyl]-N-methylcarbamoyl)-2-(2-naphthyl)ethyl)-N-methylamide

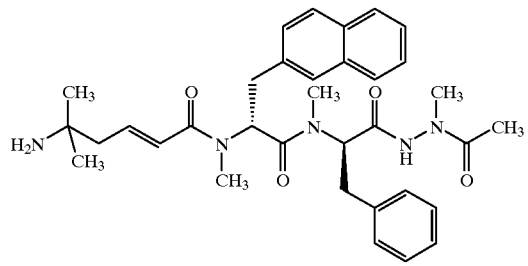

To a solution of (2E)-5-(tert-butyloxycarbonylamino)-5-methylhex-2-enoic acid (0.1 g, 0.42 mmol) in methylene chloride (5 ml) was added 1-hydroxy-7-azabenzotriazole (0.06 g, 0.42 mmol) and 1-ethyl-3-(3-dimethylaminopropyl) carbodiimide hydrochloride (0.08 g, 0.42 mmol) and the mixture was cooled to 0° C. Then (2R)-N-[(1R)-2-(N'-acetyl-N'-methylhydrazino)-1-benzyl-2-oxoethyl]-N-methyl-2-(methylamino)-3-(2-naphthyl)propionamide (0.13 g, 0.28 mmol) and diisopropylethylamine (0.062 ml, 0.36 mmol) were added and the mixture was stirred at room temperature overnight. Then methylene chloride (50 ml) was added and the mixture was washed with water (10 ml), saturated sodium bicarbonate (10 ml), brine (10 ml), dried (MgSO$_4$), filtered and concentrated in vacuo. The product was chromatographed on silica (40 g) with heptane:ethyl acetate (1:1) to give 0.12 g (63%) of ((3E)-4-[N-((1R)-1-(N-[(1R)-2-(N'-acetyl-N'-methylhydrazino)-1-benzyl-2-oxoethyl]-N-methylcarbamoyl]-1,1-dimethylbut-3-enyl)carbamic acid tert-butyl ester as a colourless oil.

A solution of ((3E)-4-[N-((1R)-1-(N-[(1R)-2-(N'-acetyl-N'-methylhydrazino)-1-benzyl-2-oxoethyl]-N-methylcarbamoyl)-2-(2-naphthyl)ethyl)-N-methylcarbamoyl]-1,1-dimethylbut-3-enyl)carbamic acid tert-butyl ester (0.1 g, 0.146 mmol) in methylene chloride (2 ml) was cooled to 0° C. and trifluoroacetic acid (2 ml) was added and the mixture was stirred for 30 min. Then methylene chloride (50 ml) and saturated sodium bicarbonate (5 ml) was added and the mixture was titrated with solid sodium bicarbonate until pH=7. The water layer was separated and extracted with methylene chloride (20 ml) and the combined organic layers were washed with brine (10 ml), dried (MgSO$_4$), filtered and concentrated in vacuo. The obtained product was dissolved in acetonitrile/water 1:20 (10 ml) and applied to a C-18 Sep-Pak Classic© cartridge (2.0 g, purchased from Waters™), which had been pre-washed with acetonitrile (100 ml) and water (100 ml). Then a gradient of an eluent consisting of water/acetonitrile/trifluoroacetic acid (10, 50, and 70% acetonitrile in water/trifluoroacetic acid (0.1%)) was run through the Sep-Pak©. The relevant fractions were combined and lyophilised to 0.086 g (84%) of the trifluoroacetic acid salt of (2E)-5-amino-5-methylhex-2-enoic acid N-((1R)-1-(N-[(1R)-2-(N'-acetyl-N'-methylhydrazino)-1-benzyl-2-oxoethyl]-N-methylcarbamoyl)-2-(2-naphthyl)ethyl)-N-methylamide as a white amorphous powder.

LC-MS: R$_t$=9.255 min, m/z=586.4 (m+1); HPLC: R$_t$=31.47 min (A1), R$_t$=33.30 (B1); $^1$H NMR (DMSO) Selected peaks: δ 5.3 (dd, 1H, C=CH—CO) 5.7 (t, 1H, CH—CH$_2$C$_6$H$_5$) 6.15 (d, 1H, CH$_2$—CH=C) 6.4 (m, 1H, CH[\M]CH$_2$C$_{10}$H$_7$).

EXAMPLE 4

(2E)-5-Amino-5-methylhex-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide

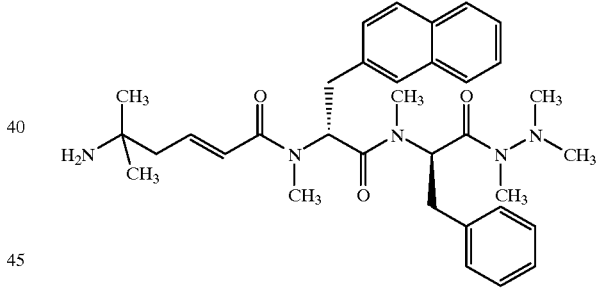

N,N',N'-Trimethylhydrazinecarboxylic acid tert-butyl ester

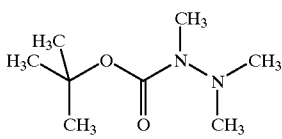

To a solution of tert-butyl carbazate (1.0 g, 7.56 mmol) in anhydrous tetrahydrofuran (40 ml) at 0° C. was added sodium hydride (60% dispersion in oil, 2.73 g, 68 mmol) and methyl iodide (11.3 ml, 181 mmol) and the mixture was stirred for 3 days. Then tetrahydrofuran (100 ml) was added and the suspension was filtrated and the filtrate was concentrated in vacuo. The obtained product was dissolved in ethyl acetate and chromatographed on silica gel (40 g) with heptane:ethyl acetate (1:1) and concentrated to give 0.53 g (40%) of N,N',N'-trimethylhydrazinecarboxylic acid tert-butyl ester as a thin oil.

¹H NMR (CDCl₃): δ 1.48 (s, 9H, (CH₃)₃C—O) 2.6 (s, 6H, 2 N—CH₃) 2.9 (s, 3H, N—CH₃).

N-Methyl-N-[(1R)-2-phenyl-1-(N,N',N'-trimethylhydrazinocarbonyl)ethyl]carbamic acid tert-butyl ester

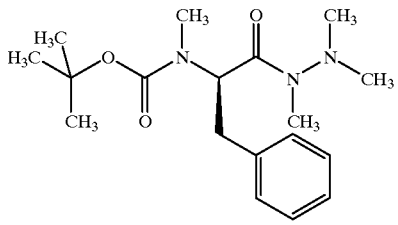

To a solution of N,N',N'-trimethylhydrazinecarboxylic acid tert-butyl ester (0.52 g, 2.99 mmol) in methylene chloride (4 ml) was added trifluoroacetic acid (4 ml) and the mixture was stirred for 60 min. The mixture was concentrated in vacuo and stripped three times with methylene chloride to give 0.61 g of N,N,N'-trimethylhydrazine trifluoroacetate as a thin oil.

Then (2R)-2-(tert-butoxycarbonylmethylamino)-3-phenyl propionic acid (1.0 g, 3.58 mmol) was dissolved in methylene chloride (5 ml) and 1-ethyl-3-(3-dimethylaminopropyl)carbodiimide hydrochloride (0.34 g, 1.79 mmol) was added and stirred for 30 min. Then a mixture of N,N,N'-trimethylhydrazine trifluoro acetate (0.37 g, 1.96 mmol) and diisopropylethylamine (0.92 ml, 5.34 mmol) was added and the mixture was stirred for 2 days.

Methylene chloride (50 ml) was added and the mixture was washed with water (50 ml). The organic layer was washed with saturated aqueous sodium bicarbonate (2×10 ml) and water (50 ml), dried (MgSO₄), filtered, concentrated in vacuo, and chromatographed on silica (100 g) with heptane:ethyl acetate (1:1) to give 0.30 g N-methyl-N-[(1R)-2-phenyl-1-(N,N',N'-trimethylhydrazinocarbonyl)ethyl]carbamic acid tert-butyl ester as an amorphous powder.

HPLC: R$_t$=13.03 min (H8); ¹H NMR (CDCl₃) Selected peaks: δ 1.23+1.35 (2 s, 9H, (CH₃)₃C—O, rotamere) 2.25+2.42+2.45 (3 s, 6H, N—N(CH₃)₂, rotamere).

N-Methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)carbamic acid tert-butyl ester

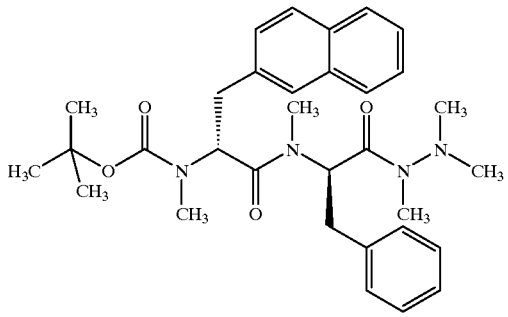

To a solution of N-methyl-N-[(1R)-2-phenyl-1-(N,N',N'-trimethylhydrazinocarbonyl)ethyl]carbamic acid tert-butyl ester (0.3 g, 0.89 mmol) in methylene chloride (1 ml) was added trifluoroacetic acid (1 ml) and the mixture was stirred for 30 min. The mixture was concentrated in vacuo, stripped three times with methylene chloride and suspended in methylene chloride:(methanol/ammonia) (1:1) (2 ml) and trifluoroammonium acetate precipitated. Then diethyl ether (10 ml) was added and the mixture was filtered and the filtrate was concentrated in vacuo to give 0.31 g of (2R)-2-methylamino-3-phenylpropionic acid trimethylhydrazide as an oil.

Then (2R)-2-(N-tert-butoxycarbonyl-N-methylamino)-3-(2-naphthyl)propionic acid (0.35 g, 1.07 mmol) was dissolved in methylene chloride (20 ml) and a mixture of 1-hydroxy-7-azabenzotriazole (0.15 g, 1.07 mmol) and 1-ethyl-3-(3-dimethylaminopropyl)carbodiimide hydrochloride (0.21 g, 1.07 mmol) was added and stirred for 30 min. Then a mixture of (2R)-2-methylamino-3-phenylpropionic acid trimethylhydrazide (0.21 g, 0.89 mmol) and diisopropylethylamine (0.20 ml) was added and the mixture was stirred overnight. Methylene chloride (30 ml) was added and the mixture was washed with water (10 ml). The organic layer was washed with aqueous sodium bicarbonate (10 ml) and brine (50 ml), dried (MgSO₄), filtered, concentrated to an oil, and chromatographed on silica (40 g) with heptane:ethyl acetate (3:7) to give 0.43 g of N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)carbamic acid tert-butyl ester as an oil.

¹H NMR (CDCl₃) Selected peaks: δ 0.92+1.22 (2 s, 9H, (CH₃)₃C—O, rotamere) 5.0+5.3 (2 t, 1H, CH—CH₂C₆H₅, rotamere) 6.3+6.45 (2 t, 1H, CH—CH₂C₁₀H₇, rotamere).

(2E)-5-Amino-5-methylhex-2-enoic acid N-methyl-N-(1R)-1-(N-methyl-N-[(1R)-2-phenyl-1-(N,N',N'-trimethylhydrazinocarbonyl)ethyl]carbamoyl)-2-(2-naphthyl)ethyl)amide

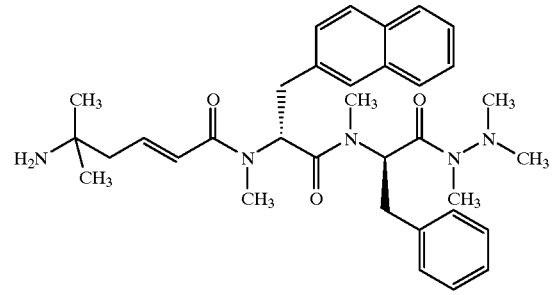

To a solution of of N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)carbamic acid tert-butyl ester (0.43 g, 0.79 mmol) in methylene chloride (2 ml) was added trifluoroacetic acid (2 ml) at 0° C. and stirred for 30 min. The mixture was concentrated in vacuo and stripped three times with methylene chloride. The obtained oil was dissolved in methanol/ammonia (2 ml) and added methylene chloride (20 ml) and silica gel (5 g) and concentrated in vacuo. The obtained powder was extracted by filtration with methylene chloride (50 ml) and methylene chloride:(methanol/ammonia) (9:1) and the combined extracts were concentrated in vacuo to 0.36 g of crude product as a foam.

Then (2E)-5-(tert-butyloxycarbonylamino)-5-methylhex-2-enoic acid (0.12 g, 0.48 mmol) was dissolved in methylene chloride (5 ml) and a mixture of 1-hydroxy-7-azabenzotriazole (0.065 g, 0.48 mmol) and 1-ethyl-3-(3-dimethylaminopropyl)-carbodiimide hydrochloride (0.092 g, 0.48 mmol) was added and stirred for 30 min. Then a mixture of the obtained crude product (0.18 g, 0.40 mmol) and diisopropylethylamine (0.09 ml, 0.53 mmol) was added and the mixture was stirred overnight.

Methylene chloride (50 ml) was added and the mixture was washed with water (10 ml). The organic layer was washed with aqueous sodium bicarbonate (10 ml) and brine (50 ml), dried (MgSO$_4$), filtered, concentrated to 0.14 g of a colourless oil. The oil was dissolved in methylene chloride (2 ml), cooled to 0° C. and trifluoroacetic acid (2 ml) was added and the mixture was stirred for 30 min. The reaction mixture was quenched with methylene chloride (50 ml) and water (10 ml) and titrated to pH~7 with solid sodium bicarbonate. The organic layer was separated and washed with water (10 ml), dried (MgSO$_4$), filtered and concentrated in vacuo.

The obtained product was dissolved in acetonitrile/water 1:20 (10 ml) and applied to a C-18 Sep-Pak Classic© cartridge (2.0 g, purchased from Waters™), which had been prewashed with acetonitrile (100 ml) and water (100 ml). Then a gradient of an eluent consisting of water/acetonitrile/ trifluoroacetic acid (10, 15, 20 and 25% acetonitrile in water/trifluoroacetic acid) was run through the Sep-Pak©. The relevant fractions were combined and lyophilised to 0.072 g of the trifluoroacetic acid salt of (2E)-5-amino-5-methylhex-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide as a white amorphous powder.

LC-MS: R$_t$=9.96 min, m/z=572.4 (m+1); $^1$HPLC: R$_t$=35.23 min (A1), R$_t$=37.45 (B1); $^1$H NMR (DMSO) Selected peaks: δ 5.1 (t, 1H, CH—CH$_2$C$_6$H$_5$) 6.1 (t, 1H, CH$_2$—CH=C) 6.2 (d, 1H, C=CH—CO) 6.4 (t, 1H, CH—CH$_2$C$_{10}$H$_7$).

EXAMPLE 5

3-Aminomethyl-N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)benzamide

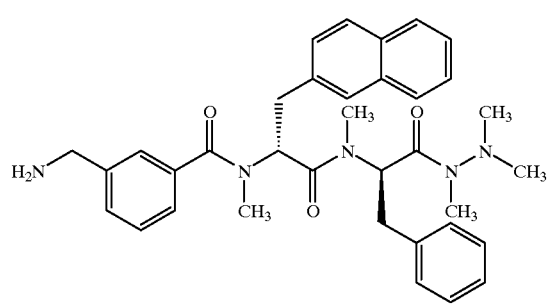

To a solution of 3-[(9H-fluoren-9-ylmethoxycarbonylamino)methyl]benzoic acid (0.18 g, 0.48 mmol) in methylene chloride (10 ml) was added 1-hydroxy-7-azabenzotriazole (0.065 g, 0.48 mmol) and 1-ethyl-3-(3-dimethylaminopropyl)carbodiimide hydrochloride (0.092 g, 0.48 mmol) and the mixture was cooled to 0° C. Then (2R)-N-methyl-2-(methylamino)-3-(2-naphthyl)-N-[(1R)-2-phenyl-1-(N,N',N'-trimethylhydrazinocarbonyl)ethyl] propionamide (0.18 g, 0.40 mmol) and duisopropylethylamine (0.089 ml, 0.52 mmol) were added and the mixture was stirred at room temperature overnight. Then methylene chloride (50 ml) was added and the mixture was washed with water (10 ml), saturated sodium bicarbonate (10 ml), brine (10 ml), dried (MgSO$_4$), filtered and concentrated in vacuo. The product was chromatographed on silica gel (40 g) with heptane:ethyl acetate (1:1) to give 0.12 g (37%) of (3-[N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)carbamoyl]benzyl)carbamic acid ((9H-fluoren-9-yl)methyl) ester as a colourless oil.

To a solution of (3-[N-methyl-N-((1R)-1-(N-methyl-N-[((1R)-2-phenyl-1-(N,N',N'-trimethylhydrazinocarbonyl) ethyl]carbomoyl)-2-(2-naphthyl)carbamoyl]benzyl) carbamic acid ((9H-fluoren-9-yl)methyl) ester (0.12 g, 0.15 mmol) in methylene chloride (4 ml) was added tris(2-aminoethyl)amine (4 ml) and the mixture was stirred for 90 min. Then methylene chloride (50 ml) was added and the mixture was washed with brine (2×20 ml), phosphate buffer (pH=6, 2×20 ml), water (20 ml), brine (10 ml), dried (MgSO$_4$), filtered and concentrated in vacuo.

The obtained product was dissolved in acetonitrile/water 1:20 (10 ml) and applied to a C-18 Sep-Pak Classic© cartridge (0.25 g, purchased from Waters™), which had been prewashed with acetonitrile (10 ml) and water (10 ml). Then a gradient of an eluent consisting of water/acetonitrle/ trifluoroacetic acid (10, 30, and 70% acetonitrile in water/ trifluoroacetic acid) was run through the Sep-Pak© (2 g). The relevant fractions were combined and lyophilised to 0.08 g (77%) of the trifluoroacetic acid salt of 3-aminomethyl-N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)benzamide as a white amorphous powder.

LC-MS: R$_t$=9.87 min, m/z=580.2 (m+1); HPLC: R$_t$=35.28 min (A1), R$_t$=37.43 (B1); $^1$H NMR (DMSO) Selected peaks: δ 5.7 (t, 1H, CH—CH$_2$C$_6$H$_5$) 6.2 (t, 1H, CH—CH$_2$C$_{10}$H$_7$) 6.8–7.9 (m, 16H, arom).

EXAMPLE 6

(2E)-5-Amino-5-methylhex-2-enoic acid N-((1R)-1-(N-[(1R)-1-(N',N'-dimethylhydrazinocarbonyl)-2-phenylethyl]-N-methylcarbamoyl)-2-(2-naphthyl)ethyl)-N-methylamide

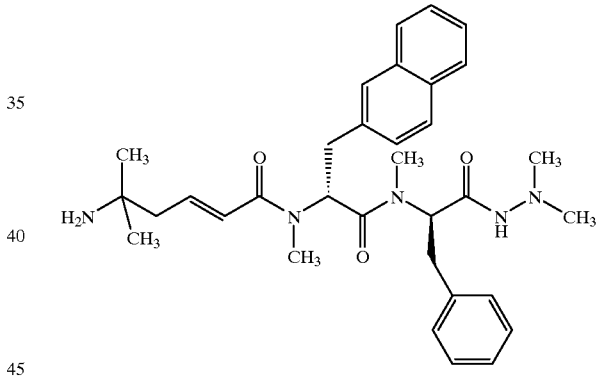

N-1-(N',N'-Dimethylhydrazinocarbonyl)-2-phenylethyl)-N-methylcarbamic acid tert-butyl ester

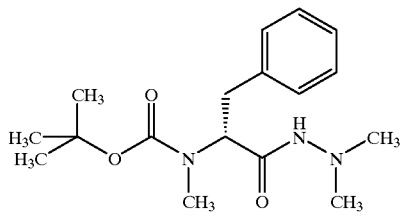

A solution of (2R)-2-(tert-butoxycarbonylmethylamino)-3-phenyl propionic acid (3.0 g, 10.74 mmol), 1-ethyl-3-(3-dimethylaminopropyl)carbodiimide hydrochloride (2.06 g, 10.74 mmol) and 1-hydroxy-7-azabenzotriazole (1.46 g, 10.74 mmol) in methylene chloride was stirred for 30 min. Then a mixture of N',N'-dimethylhydrazine (1.23 ml,16.11 mmol) and diisopropylethylamine (2.39 ml, 13.96 mmol) was added and the mixture was stirred overnight.

Ethyl acetate (100 ml) was added and the mixture was washed with water (20 ml). The organic layer was washed with saturated aqueous sodium bicarbonate (2×10 ml) and water (50 ml), dried (MgSO$_4$), filtered, concentrated in vacuo, and chromatographed on silica (100 g) with heptane-:ethyl acetate (2:3) to give 2.19 g N-methyl-N-[(1R)-2-phenyl-1-(N',N'-dimethylhydrazinocarbonyl)ethyl]carbamic acid tert-butyl ester as an amorphous powder.

HPLC: R$_t$=10.81 mn (H8); $^1$H NMR (CDCl$_3$) Selected peaks: δ 1.25+1.30+1.45+1.50 (4 s, 9H, (CH$_3$)$_3$C—O, rotamere) 2.45+2.50+2.60 (3 s, 6H, N—N(CH$_3$)$_2$, rotamere) 2.80 (s, 3H, N—CH$_3$).

(2R)-2-Methylamino-3-phenylpropionic acid N',N'-dimethylhydrazide

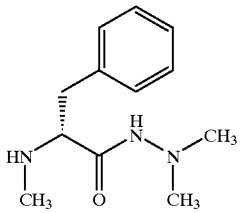

To a solution of N-methyl-N-[(1R)-2-phenyl-1-(N',N'-dimethylhydrazinocarbonyl)ethyl]carbamic acid tert-butyl ester (2.19 g, 6.81 mmol) in methylene chloride (5 ml) was added trifluoroacetic acid (5 ml) and was stirred at room temperature for 90 min. The mixture was concentrated in vacuo and stripped three times with methylene chloride (3×2 ml) to give the trifluoroacetic acid salt of (2R)-2-methylamino-3-phenylpropionic acid N',N'-dimethylhydrazide in quantitative yield.

$^1$H NMR (CDCl$_3$) Selected peaks: δ 2.30 (s, 3H, HN—CH$_3$) 2.45+2.50 (2 s, 6H, N—N(CH$_3$)$_2$, rotamere).

N-((1R)-1-(N-(1R)-1-(N',N'-Dimethylhydrazinocarbonyl)-2-phenylethyl)-N-methylcarbamoyl)-2-(2-naphthyl)ethyl)-N-mehylcarbamic acid tert-butyl ester

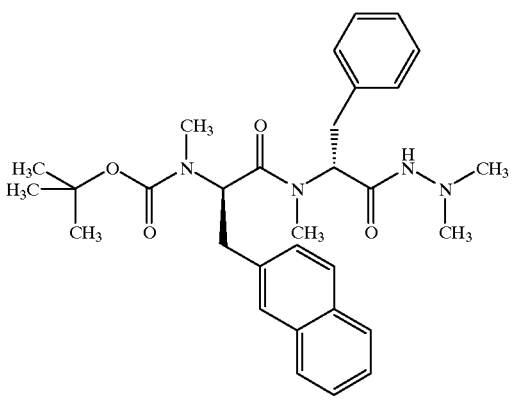

To a solution of 2(R)-(N-tert-butoxycarbonyl-N-methylamino)-3-(naphth-2-yl)propionic acid (1.77 g, 5.37 mmol) in methylene chloride (20 ml) was added 1-hydroxy-7-azabenzotriazole (0.73 g, 5.37 mmol) and 1-ethyl-3-(3-dimethylaminopropyl)carbodiimide hydrochloride (1.03 g, 5.37 mmol) and the mixture was stirred for 30 min. Then (2R)-2-methylamino-3-phenylpropionic acid N',N'-dimethylhydrazide (2.41 g, 5.37 mmol) and diisopropylethylamine (3.7 ml, 21.5 mmol) were added and the mixture was stirred at room temperature overnight. The mixture was concentrated in vacuo, and chromatographed on silica (100 g) with methylene chloride (90):methanol/ammonia (10/1) to give 2.52 g of N-((1R)-1-(N-((1R)-1-(N',N'-dimethylhydrazinocarbonyl)-2-phenylethyl)-N-methycarbamoyl)-2-(2-naphthyl)ethyl)-N-mehylcarbamic acid tert-butyl ester as a yellow oil.

LC-MC: R$_t$=13.18 min, m/z=533.2 (m+1); HPLC: R$_t$=14.12 min (H8); $^1$H NMR (CDCl$_3$) Selected peaks: δ 1.15+1.25+1.30+1.45 (4 s, 9H, (CH$_3$)$_3$—C, rotamere).

(2R)-N-[(1R)-1-(N',N'-Dimethylhydrazinocarbonyl)-2-phenylethyl]-N-methyl-2-(methylamino)-3-(2-naphthyl)propionamide

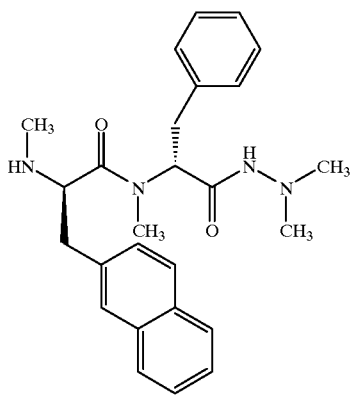

To a solution of N-((1R)-1-(N-((1R)-1-(N',N'-dimethylhydrazinocarbonyl)-2-phenylethyl)-N-methylcarbamoyl)-2-(2-naphthyl)ethyl)-N-mehylcarbamic acid tert-butyl ester (2.52 g, 4.73 mmol) in methylene chloride (5 ml) was added trifluoroacetic acid (5 ml) at 0° C. and stirred for 60 min. The mixture was concentrated in vacua and stripped three times with methylene chloride to give the trifluoroacetic acid salt of (2R)-N-[(1R)-1-(N',N'-dimethylhydrazinocarbonyl)-2-phenylethyl]-N-methyl-2-(methylamino)-3-(2-naphthyl)propionamide in quantitative yield as yellow oil.

HPLC: R$_t$=7.61 min (H8); LC-MS: R$_t$=7.72 min, m/z= 433.2 (m+1).

((3E)-4-[N-((1R)-1-(N-[(1R)-1-(N',N'-Dimethylhydrazinocarbonyl)-2-phenylethyl]-N-methylcarbamoyl)-2-(2-naphthyl)ethyl)-N-methylcarbamoyl]-1,1-dimethylbut-3-enyl)carbamic acid tert-butyl ester

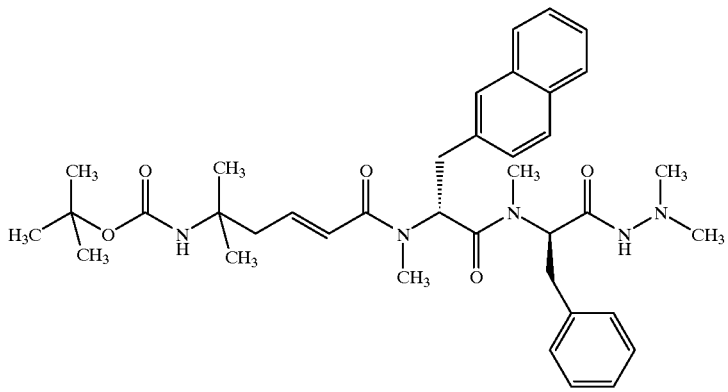

To a solution of (2E)-5-(tert-butyloxycarbonylamino)-5-methylhex-2-enoic acid (0.35 g, 1.42 mmol) in methylene chloride (5 ml) was added a mixture of 1-hydroxy-7-azabenzotriazole (0.193 g, 1.42 mmol) and 1-ethyl-3-(3-dimethylaminopropyl)-carbodiimide hydrochloride (0.272 g, 1.42 mmol) and stirred for 30 min. Then a mixture of the obtained crude (2R)-N-[(1R)-1-(N',N'-dimethylhydrazinocarbonyl)-2-phenylethyl]-N-methyl-2-(methylamino)-3-(2-naphthyl)propionamide and diisopropylethylamine (0.61 ml, 3.55 mmol) was added and the mixture was stirred overnight. The mixture was concentrated in vacuo and chromatographed on silica (40 g) with ethyl acetate (95):methanol/10% ammonia (5) to give 0.37 g of ((3E)4-[N-((1R)-1-(N-[(1R)-1-(N',N'-dimethylhydrazinocarbonyl)-2-phenylethyl]-N-methylcarbamoyl)-2-(2-naphthyl)ethyl)-N-methylcarbamoyl]-1,1-dimethylbut-3-enyl)carbamic acid tert-butyl ester as an oil.

HPLC: $R_t$=14.51 min (H8); LC-MS: $R_t$=13.39 min, m/z=658.4 (m+1).

To a solution of ((3E)4-[N-((1R)-1-(N-[(1R)-1-(N',N'-dimethylhydrazinocarbonyl)-2-phenylethyl]-N-methylcarbamoyl)-2-(2-naphthyl)ethyl)-N-methylcarbamoyl]-1,1-dimethylbut-3-enyl)carbamic acid tert-butyl ester (0.36 g, 0.55 mmol) in methylene chloride (3 ml) at 0° C. was added trifluoroacetic acid (3 ml) and the mixture was stirred for 30 min.

Methylene chloride (50 ml) and water (10 ml) was added and the solution was titrated with solid sodium bicarbonate until pH>7. The water layer was extracted with mehylene chloride (25 ml) and the combined organic layer was dried (MgSO$_4$), filtered and concentrated in vacuo.

The obtained product was dissolved in acetonitrile/water 1:20 (10 ml) and applied to a C-18 Sep-Pak Classic© cartridge (0.25 g, purchased from Waters™), which had been prewashed with acetonitrile (10 ml) and water (10 ml). Then a gradient of an eluent consisting of water/acetonitrile/trifluoroacetic acid (10, 30, and 70% acetonitrile in water/trifluoroacetic acid) was run through the Sep-Pak© (2 g). The relevant fractions were combined and lyophilised to 196 mg of the trifluoroacetic acid salt of (2E)-5-amino-5-methylhex-2-enoic acid N-((1R)-1-(N-[(1R)-1-(N',N'-dimethylhydrazinocarbonyl)-2-phenylethyl]-N-methylcarbamoyl)-2-(2-naphthyl)ethyl)-N-methylamide as a white amorphous powder.

HPLC: $R_t$=30.42 min (A1), $R_t$=30.38 (B1), $R_t$=8.40 min (H8); LC-MS: $R_t$=8.99 min, m/z=558.4.

EXAMPLE 7

(2E)-5-Amino-5-methylhex-2-enoic acid N-((1R)-1-(N-[(1R)-1-N',N'-dimethylhydrazinocarbonyl)-2-(2-thienyl)ethyl]-N-methylcarbamoyl)-2-(2-naphthyl)ethyl)-N-methylamide

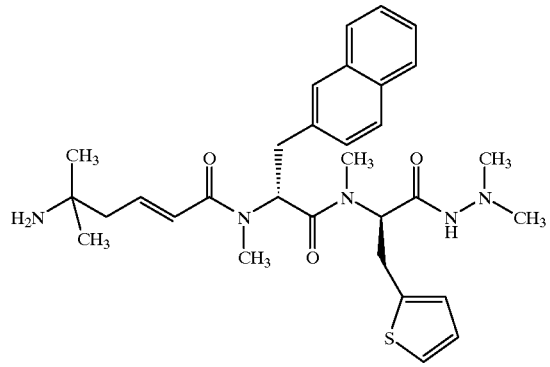

Prepared in analogy to (2E)-5-amino-5-methylhex-2-enoic acid N-((1R)-1-(N-[(1R)-1-(N',N'-dimethylhydrazinocarbonyl)-2-phenylethyl]-N-methylcarbamoyl)-2-(2-naphthyl)ethyl)-N-methylamide (example 6) using (2R)-2-(N-(tert-butoxycarbonyl)-N-methylamino)-3-(thiophen-2-yl)propionic acid instead of (2R)-2-(tert-butoxycarbonylmethylamino)-3-phenyl propionic acid.

N-[(1R)-1-(N',N'-Dimethylhydrazinocarbonyl)-2-(2-thienyl)ethyl]-N-methylcarbamic acid tert-butyl ester

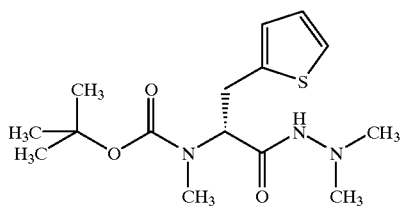

LC-MS: $R_t$=8.92 min, m/z=328.4 (m+1); $^1$H NMR (CDCl$_3$) Selected peaks: δ 1.35+1.40+1.42+1.45 (4 s, 9H, C—(CH$_3$)$_3$, rotamere) 2.45+2.55+2.60 (3 s, 6H, (CH$_3$)$_2$N—N, rotamere) 2.80+2.85 (2 s, 3H, N—CH$_3$).

N-(1R)-1-(N-[(1R)-1-(N',N'-Dimethylhydrazinocarbonyl)-2-(2-thienyl)ethyl]-N-methylcarbamoyl)-2-(2-naphthyl)ethyl)-N-methylcarbamic acid tert-butyl ester

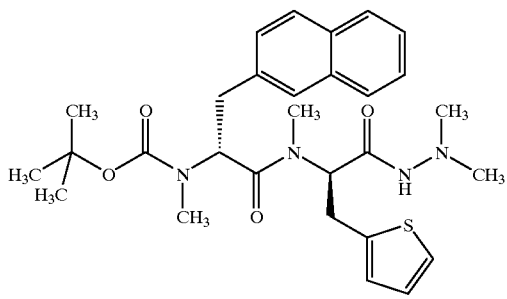

HPLC: R*t*=13.96 min (H8); LC-MS: R*t*=13.11 min, m/z= 539.4 (m+1).
(2R)-N-[(1R)-1-(N',N'-Dimethylhydrazinocarbonyl)-2-(2-thienyl)ethyl]-N-methyl-2-(methylamino)-3-(2-naphthyl) propionamide

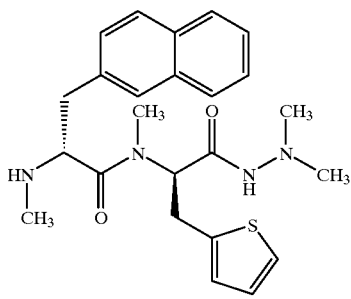

HPLC: Rt=7.41 min (H8); LC-MS: Rt=7.74 min, m/z= 439.2 (m+1).
((3E)-4-[N-((1R)-1-N-[(1R)-1-(N',N'-Dimethylhydrazinocarbonyl)-2-(2-thienyl)ethyl]-N-methylcarbamoyl)-2-(2-naphthyl)ethyl)-N-methylcarbamoyl]-1,1-dimethylbut-3-enyl)carbamic acid tert-butyl ester HPLC: Rt=14.43 min (H8); LC-MS: Rt=13.31 min, m/z= 664.4 (m+1).

(2E)-5-Amino-5-methylhex-2-enoic acid N-((1R)-1-(N-[(1R)-1-(N',N'-dimethylhydrazinocarbonyl)-2-(2-thienyl) ethyl]-N-methylcarbamoyl)-2-(2-naphthyl)ethyl)-N-methylamide

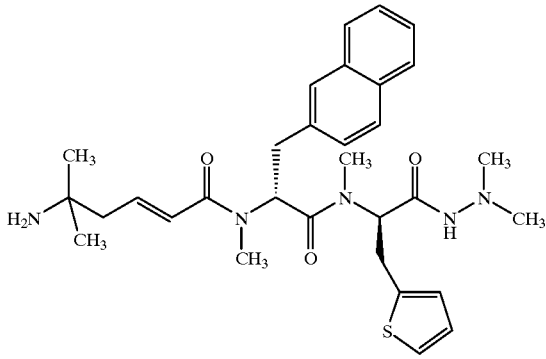

HPLC: Rt=30.03 min (A1), R*t*=29.88 min (B1); LC-MS: Rt=8.97 min, m/z=564.4 (m+1).

EXAMPLE 8

N-((1R)-1-N-[(1R)-1-(N',N'-Dimethylhydrazinocarbonyl)-2-phenylethyl]-N-methylcarbamoyl)-2-(2-naphthyl)ethyl)-N-methyl-3-(N-methylaminomethyl)benzamide

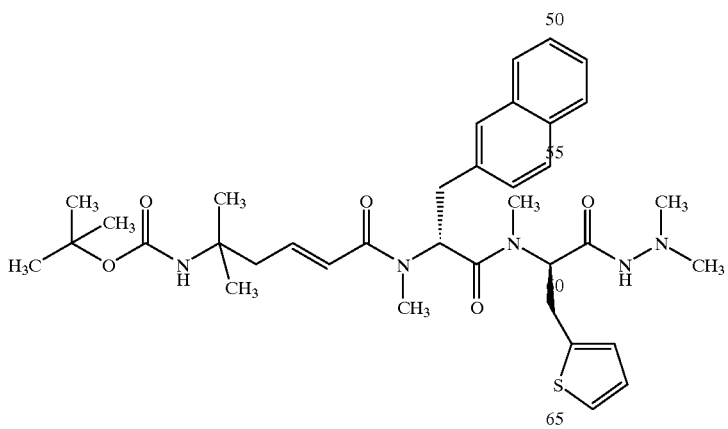

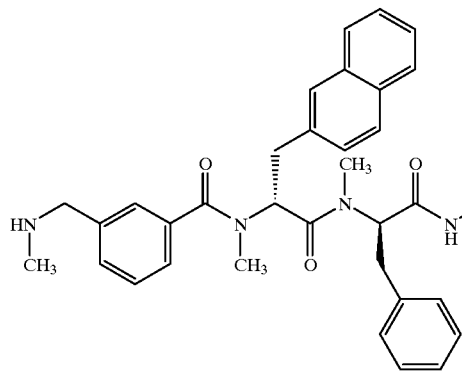
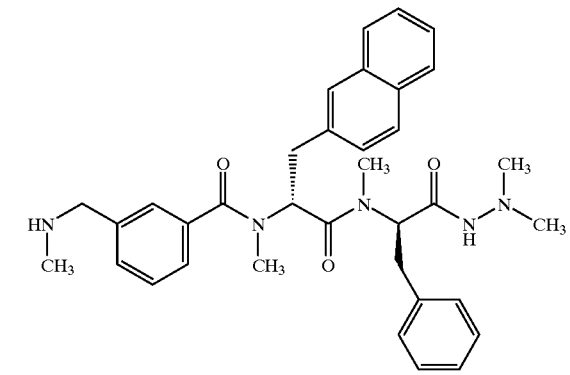

Prepared in analogy to (2E)-5-amino-5-methylhex-2-enoic acid N-((1R)-1-(N-[(1R)-1-(N',N'-dimethylhydrazinocarbonyl)-2-phenylethyl]-N-methylcarbamoyl)-2-(2-naphthyl)ethyl)-N-methylamide (example 6) using 3-[tert-butoxycarbonylmethylamino)methyl]benzoic acid instead of (2E)-5-(tert-butyloxycarbonylamino)-5-methylhex-2-enoic acid.

N-(3-[N-((1R)-1-(N-[(1R)-1-(N',N'-Dimethylhydrazinocarbonyl)-2-phenylethyl]-N-methylcarbamoyl)-2-(2-naphthyl)ethyl)-N-methylcarbamoyl]benzyl)-N-methylcarbamic acid tert-butyl ester HPLC: Rt=31.17 min(A1), Rt=30.58 min (B1); LC-MS: Rt=8.92 min, m/z=580.2 (m+1).

EXAMPLE 9

(2E)-5-Amino-5-methylhex-2-enoic acid N-((1R)-2-(biphenyl4-yl)-1-(N-methyl-N-[(1R)-2-phenyl-1-(N,N',N'-trimethylhydrazinocarbonyl)ethyl]carbamoyl)ethyl)-N-methylamide

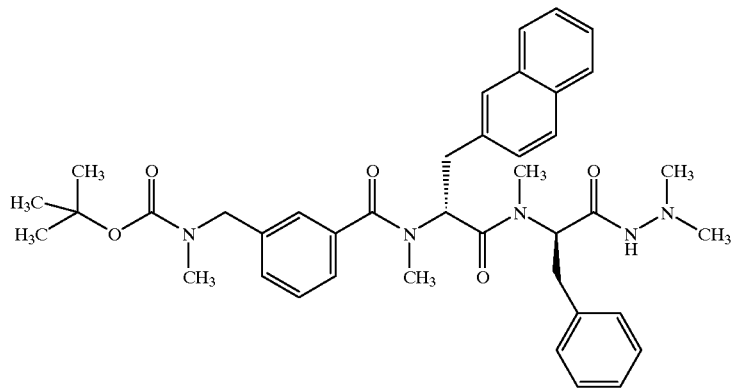

HPLC: $R_t$=14.63 min (H8); LC-MS: $R_t$=13.68 min, m/z=680.2 (m+1).

N-((1R)-1-(N-[(1R)-1-(N',N'-Dimethylhydrazinocarbonyl)-2-phenylethyl]-N-methylcarbamoyl)-2-(2-naphthyl)ethyl)-N-methyl-3(N-methylaminomethyl)benzamide

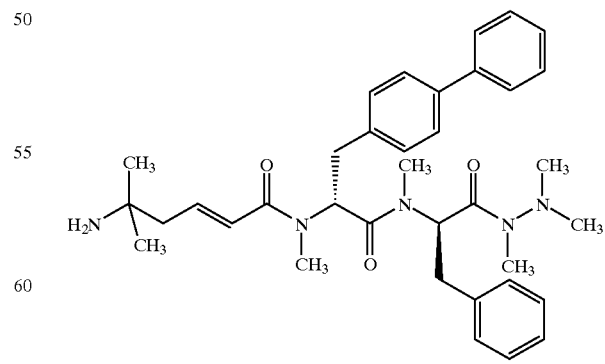

Prepared in analogy to (2E)-5-amino-5-methylhex-2-enoic acid N-((1R)-1-(N-[(1R)-1-(N,N',N'-trimethylhydrazinocarbonyl)-2-phenylethyl]-N- methylcarbamoyl)-2-(2-naphthyl)ethyl)-N-methylamide (example 4) using (2R)-N-tert-butoxycarbonylamino-N-methyl-D-4,4'-biphenylalanine instead of 2(R)-(N-tert-butoxycarbonyl-N-methylamino)-3-(naphth-2-yl)propionic acid.

N-((1R)-2-(Biphenyl-4-yl)-1-(N-methyl-N-[(1R)-2-phenyl-1-(N,N',N'-trimethylhydrazinocarbonyl)ethyl]carbamoyl)ethyl)-N-methylcarbamic acid tert-butyl ester

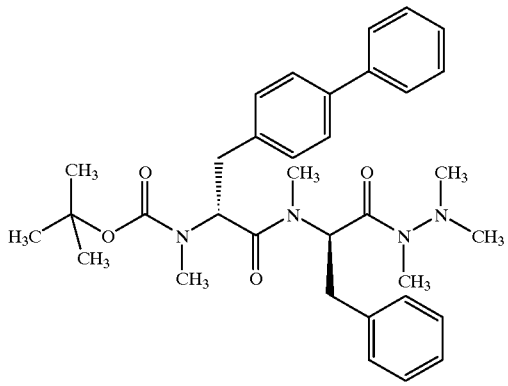

HPLC: Rt=16.70 min (H8); LC-MS: Rt=17.29 min, m/z=573.4 (m+1).

(2R)-3-(Biphenyl-4-yl)-N-methyl-2-(methylamino)-N-[(1R)-2-phenyl-1-(N,N',N'-trimethylhydrazinocarbonyl)ethyl]propionamide

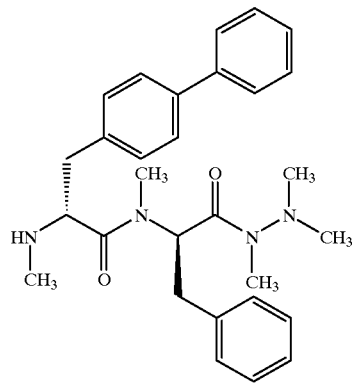

HPLC: Rt=8.56 min (H8); LC-MS: Rt=10.51 min, m/z=473.2 (m+1).

((3E)-4-[N-((1R)-2-(Biphenyl4-yl)-1-(N-methyl-N-[(1R)-2-phenyl-1-(N,N',N'-trimethylhydrazinocarbonyl)ethyl]carbamoyl)ethyl)-N-methylcarbamoy]-1,1-dimethylbut-3-enyl)carbamic acid tert-butyl ester

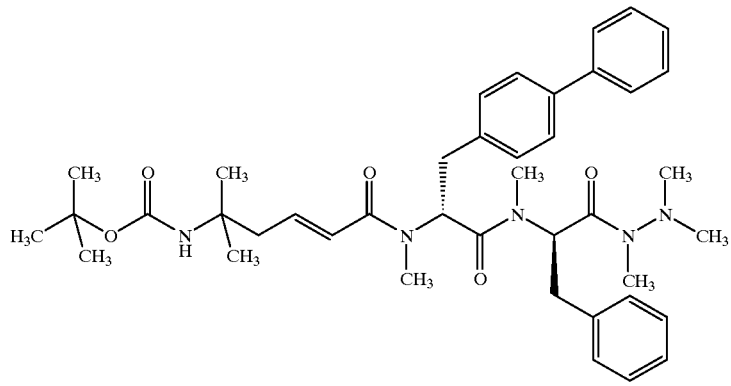

HPLC: Rt=16.22 min (H8); LC-MS: Rt=17.16 min, m/z=698.6 (m+1).

(2E)-5-Amino-5-methylhex-2-enoic acid N-((1R)-2-(biphenyl-4-yl)-1-(N-methyl-N-[(1R)-phenyl-1-(N,N',N'-trimethylhydrazinocarbonyl)ethyl]carbamoyl)ethyl)-N-methylamide

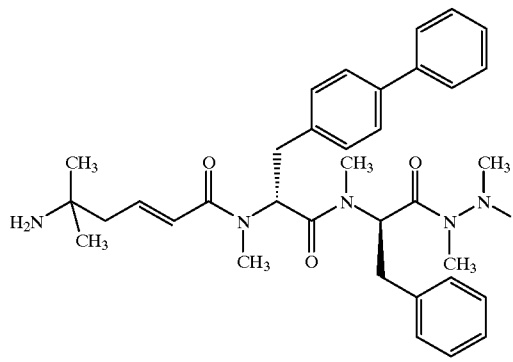

HPLC: Rt=37.23 min (A1), Rt=38.88 min (B1), Rt=10.88 min (H8); LC-MS: Rt=11.14 min, m/z=598.4 (m+1).

EXAMPLE 10

(2E)-4-(1-Aminocyclobutyl)but-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide

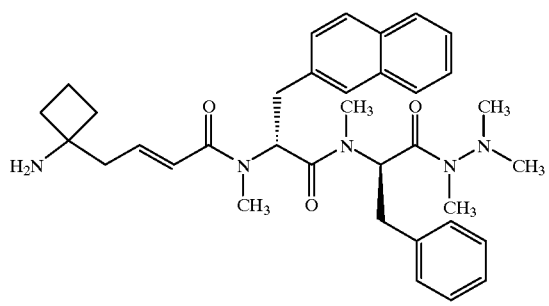

Prepared in analogy to (2E)-5-amino-5-methylhex-2-enoic acid N-((1R)-1-(N-[(1R)-1-(N,N',N'-trimethylhydrazinocarbonyl)-2-phenylethyl]-N-methylcarbamoyl)-2-(2-naphthyl)ethyl)-N-methylamide (example 4) using (2E)-4-(1-(tert-butoxycarbonylamino)cyclobutyl)but-2-enoic acid instead of (2E)-5-(tert-butyloxycarbonylamino)-5-methylhex-2-enoic acid.
(1-((2E)-3-[N-Methyl-N-(1R)-1-(N-methyl-N-[(1R)-2-phenyl-1-(N,N',N'-trimethylhydrazinocarbonyl)ethyl]carbamoyl)-2-(2-naphthyl)ethyl)carbamoyl]allyl)cyclobutyl)carbamic acid tert-butyl ester HPLC: Rt=15.75 min (H8); LC-MS: Rt=16.63 min, m/z=684.2 (m+1).
(2E)-4-(1-Aminocyclobutyl)but-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide

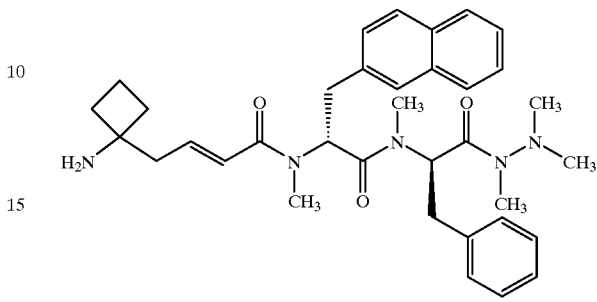

HPLC: Rt=35.28 min (A1), Rt=36.92 min (B1), Rt=10.48 min (H8); LC-MS: Rt=10.57 min, m/z=584.4 (m+1).

EXAMPLE 11

(2E)-5-Amino-5-methylhex-2-enoic acid N-((1R)-2-(biphenyl-4-yl)-1-(N-methyl-N-[(1R)-2-phenyl-1-((piperidin-1-yl)carbamoyl)ethyl]carbamoyl)ethyl)-N-methylamide

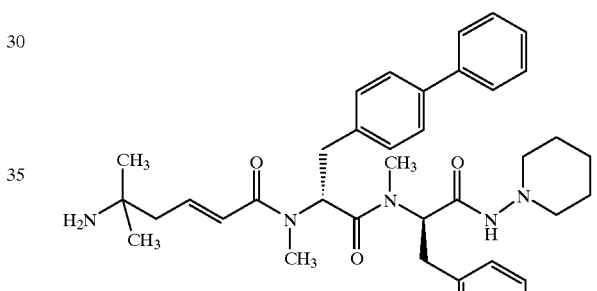

Prepared in analogy to (2E)-5-Amino-5-methylhex-2-enoic acid N-((1R)-2-(biphenyl4-yl)-1-(N-methyl-N-[(1R)-2-phenyl-1-(N,N',N'-trimethylhydrazinocarbonyl)ethyl]carbamoyl)ethyl)-N-methylamide (example 9) but using N-aminopiperidine instead of N,N',N'-trimethylhydrazine.
N-Methyl-N-[(1R)-2-phenyl-1-((piperidin-1-yl)carbamoyl)ethyl]carbamic acid tert-butyl ester

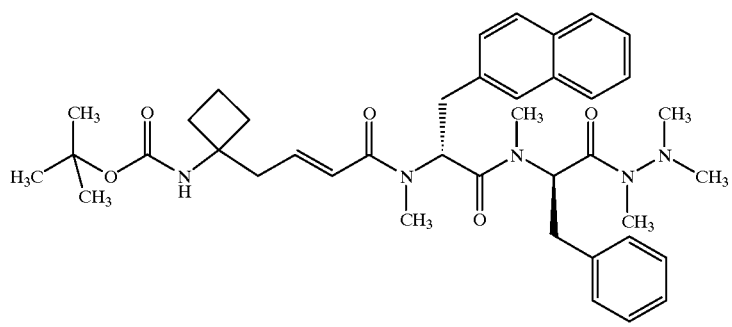

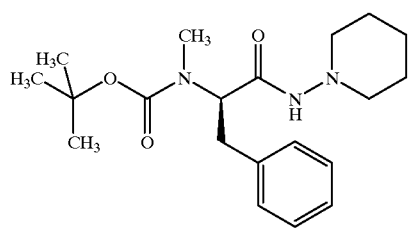

LC-MS: Rt=13.68 min, m/z=362.0 (m+1).

(2R)-2-(Methylamino)-3-phenyl-N-(piperidin-1-yl) propionamide

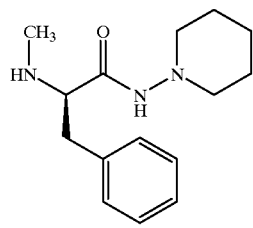

HPLC: R$_t$=5.55 min (H8); LC-MS: R$_t$=6.87 min, m/z=262.4 (m+1).

N-((1R)-2-(Biphenyl-4-yl)-1-(N-methyl-N-[(1R)-2-phenyl-1-((piperidin-1-yl)carbamoyl)ethyl]carbamoyl)ethyl)-N-methylcarbamic acid tert-butyl ester

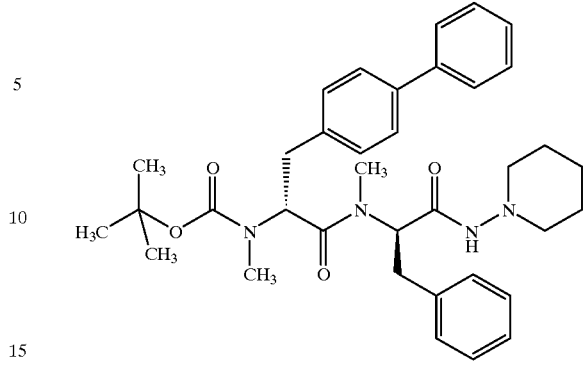

HPLC: Rt=16.22 min (H8)
LC-MS: Rt=15.41 min, m/z=599.2 (m+1).
(2R)-3-(Biphenyl-4-yl)-N-methyl-2-(methylamino)-N-[(1R)-2-phenyl-1-((piperidin-1-yl)carbamoyl)ethyl] propionamide

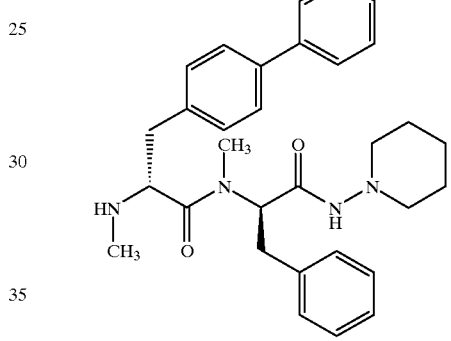

HPLC: Rt=9,11 min (H8); LC-MS: Rt=9,71 min, m/z=499,2 (m+1).
((3E)-4-[N-(1R)-2-(Biphenyl-4-yl)-1-(N-methyl-N-[(1R)-2-phenyl-1-((piperidin-1-yl)carbamoyl)ethyl]carbamoyl)ethyl)-N-methylcarbamoyl]-1,1-dimethylbut-3-enyl) carbamic acid tert-butyl ester

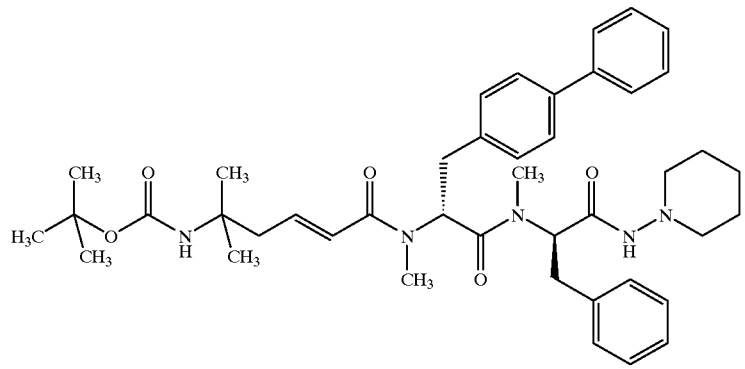

HPLC: Rt=16,25 min (H8); LC-MS: Rt=15,13 min, m/z= 724,6 (m+1).

(2E)-5-Amino-5-methylhex-2-enoic acid N-((1R)-2-(biphenyl-4-yl)-1-(N-methyl-N-[(1R)-2-phenyl-1-(piperidin-1-yl)carbamoyl)ethyl]carbamoyl)ethyl)-N-methylamide

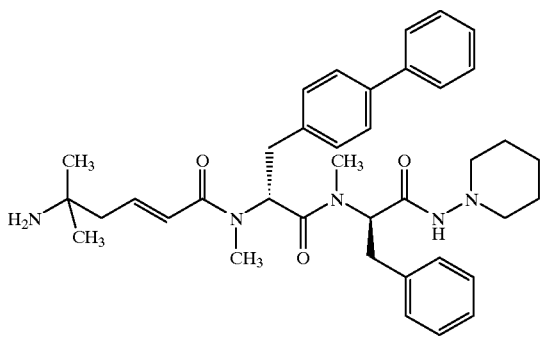

HPLC: Rt=37,03 min (A1), Rt=35,93 min (B1), Rt=10,45 min (H8); LC-MS: Rt=10,24 min, m/z=624,4 (m+1).

EXAMPLE 12

(2E)-5-Amino-5-methylhex-2-enoic acid N-methyl-N-((1R)-1-(N-methyl-N-[(1R)-2-(2thienyl)-1-(N,N',N'-trimethylhydrazinocarbonyl)ethyl]carbamoyl)-2-(2-naphthyl)ethyl)amide

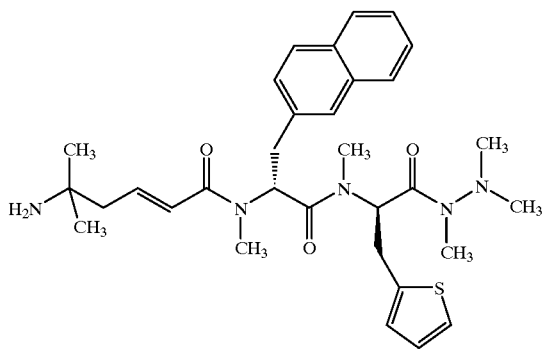

Prepared in analogy to (2E)-5-amino-5-methylhex-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide (example 4) using (2R)-2-(N-(tert-butoxycarbonyl)-N-methylamino)-3-(thiophen-2-yl)propionic acid instead of (2R)-2-(tert-butoxycarbonylmethylamino)-3-phenyl propionic acid.

N-Methyl-N-[(1R)-2-(2-thienyl)-1-(N,N',N'-trimethylhydrazinocarbonyl)ethyl]acarbamic acid tert-butyl ester

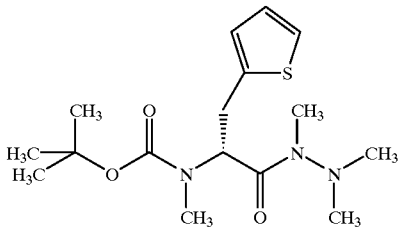

HPLC: Rt = 12.88 min (H8)

LC-MS: Rt = 13.29 min, m/z = 342.2 (m+1) (2R)-2-(Methylamino)-3-(2-thienyl)propionic acid trimethylhydrazide

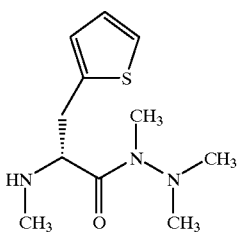

HPLC: Rt = 5.26 min (H8) LC-MS: Rt = 6.67 min, m/z = 242.6 (m+1)

N-Methyl-N-((1R)-1-N-methyl-N-[(1R)-2-(2-thienyl)-1-(N,N',N'-trimethylhydrazinocarbonyl)ethyl]carbamoyl)-2-(2-naphthyl)ethyl)carbamic acid tert-butyl ester

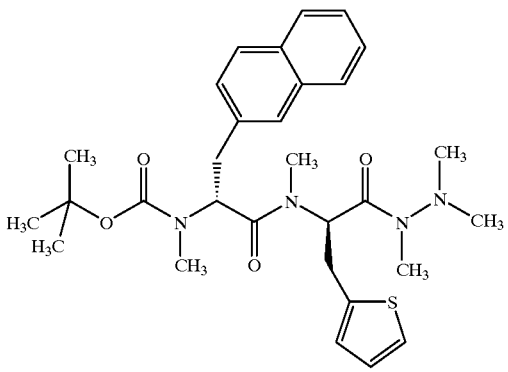

HPLC: R$_t$ = 15.85 min (H8)

(2R)-N-Methyl-2-(methylamino)-3-(2-naphthyl)-N-[(1R)-2-(2-thienyl)-1-(N,N',N'-trimethylhydrazinocarbonyl)ethyl]propionamide

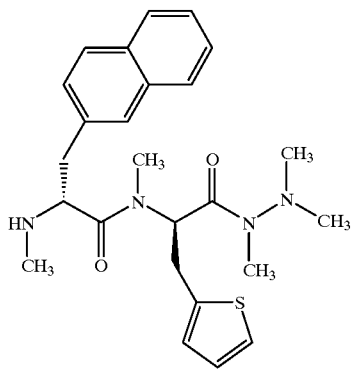

HPLC: Rt = 8.79 min (H 8) LC-MS: Rt = 9.72 min, m/z = 453.2 (m+1)

((3E)-1,1-Dimethyl-4-[N-methyl-N-((1R)-1-(N-methyl-N-[(1R)-2-(2-thienyl)1-(N,N',N'-trimethylhydrazinocarbonyi)ethyl]carbamoyl)-2-(2-naphthyl)ethyl)carbamoyl]but-3-enyl)carbamic acid tert-butyl ester

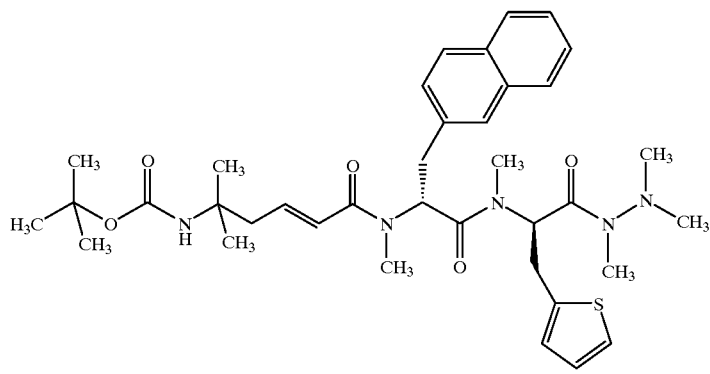

HPLC: Rt = 15,83 min (H8) LC-MS: Rt = 16,19 min m/z = 678,2 (m+1)

(2E)-5-Amino-5-methylhex-2-enoic acid N-methyl-N-((1R)-1-(N-methyl-N-[(1R)-2-(2-thienyl)-1-(N,N',N'-trimethylhydrazinocarbonyl)ethyl]carbamoyl)-2-(2-naphthyl)ethyl)amide

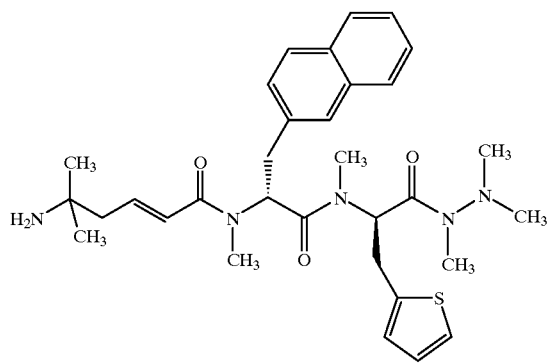

HPLC: Rt = 33.85 min (A1), Rt = 35.38 min (B1) LC-MS: Rt = 10.02 min, m/z = 578.2 (m+1)

EXAMPLE 13

(2E)-5-Amino-5-methylhex-2-enoic acid N-((1R)-2-(1H-indol-3-yl)-1-N-methyl-N-[(1R)-2-phenyl-1-(N,N',N'-trimethylhydrazinocarbonyl)ethyl]carbamoyl)ethyl)amide

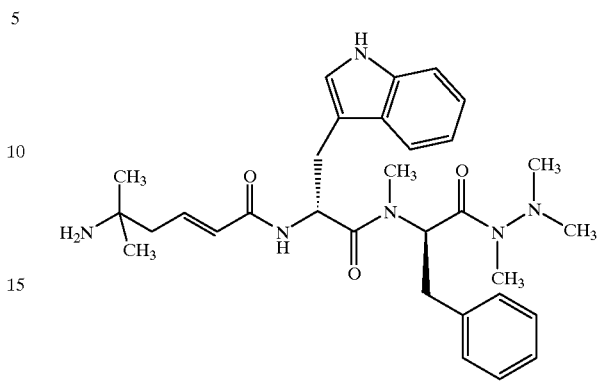

Prepared in analogy to (2E)-5-amino-5-methylhex-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide (example 4) using 2-tert-butoxycarbonylamino-3-(1-H-indol-3-yl)-propionic acid instead of 2(R)-(N-tert-butoxycarbonyl-N-methylamino)-3-(naphth-2-yl)propionic acid.

((1R)-2-(1H-Indol-3-yl)-1-(N-methyl-N-[(1R)-2-phenyl-1-(N,N',N'-trimethylhydrazinocarbonyl)ethyl]carbamoyl)ethyl)carbamic acid tert-butyl ester

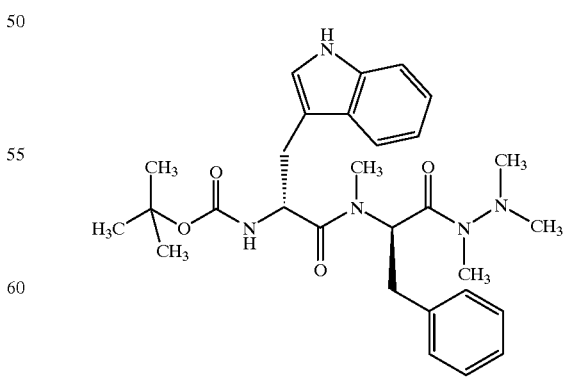

HPLC: Rt = 13.85 min (H8) LC-MS: Rt = 14.24 min, m/z = 522.2 (m+1)

(2R)-2-Amino-3-(1H-indol-3-yl)-N-methyl-N-[(1R)-2-phenyl-1-(N,N',N'-trimethylhydrazinocarbonyl)ethyl]propionamide

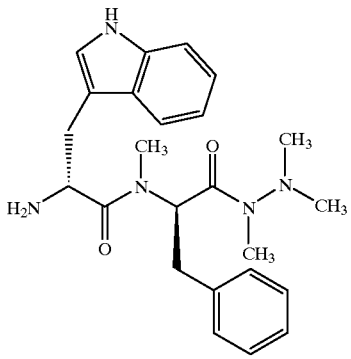

HPLC: Rt = 9.02 min (H8) LC-MS: Rt = 9.06 min, m/z = 422,2 (m+1)

[(3E)-4-((1R)-2-(1H-Indol-3-yl)-1-N-methyl-N-[(1R)-2-phenyl-1-(N,N',N'-trimethylhydrazinocarbonyl)ethyl]carbamoyl)ethylcarbamoyl)-1,1-dimethylbut-3-enyl]carbamic acid tert-butyl ester

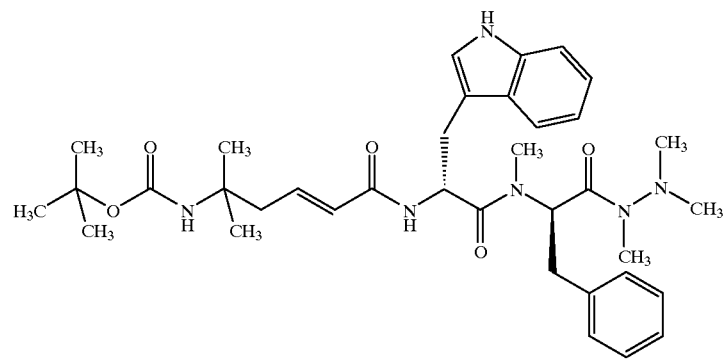

HPLC: $R_t$ = 13.98 min (H8) LC-MS: $R_t$ = 15.24 min, m/z = 647.4 (m+1)

(2E)-5-Amino-5-methylhex-2-enoic acid N-((1R)-2-(1H-indol-3-yl)-1-(N-methyl-N-[(1R-2-phenyl-1-(N,N',N'-trimethylhydrazinocarbonyl)ethyl]carbamoyl)ethyl)amide

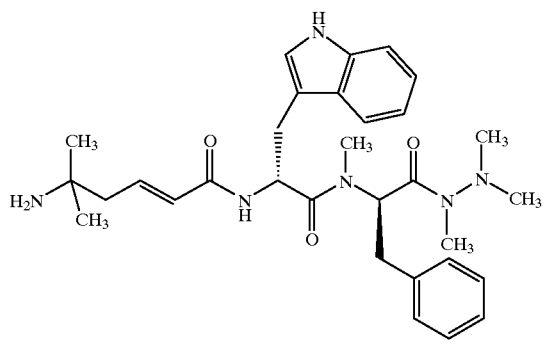

HPLC: $R_t$ = 30.56 min (A1), $R_t$ = 32.10 (B1) LC-MS: $R_t$ = 15.24 min, m/z = 647.4 (m+1)

EXAMPLE 14

2-Amino-N-((1R)-2-(1H-indol-3-yl)-1-(N-methyl-N-[(1R)-2-phenyl-1-(N,N',N'-trimethylhydrazinocarbonyl)ethyl]carbamoyl)ethyl)-2-methylpropionamide

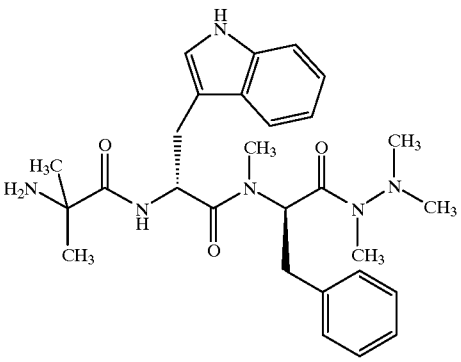

Prepared in analogy to (2E)-5-Amino-5-methylhex-2-enoic acid N-((1R)-2-(1H-indol-3-yl)-1-(N-methyl-N-[(1R)-2-phenyl-1-(N,N',N'-trimethylhydrazinocarbonyl)ethyl]carbamoyl)ethyl)amide (example 13) using 2-tert-butoxycarbonylamino-2-methylpropionic acid instead of (2E)-5-(tert-butyloxycarbonylamino)-5-methylhex-2-enoic acid.

[(1R)-1-((1R)-2-(1H-Indol-3-yl)-1-(N-methyl-N-[(1R)-2-phenyl-1-(N,N',N'-trimethylhydrazinocarbonyl)ethyl]carbamoyl)ethylcarbamoyl)-1-methylethyl]carbamic acid tert-butyl ester

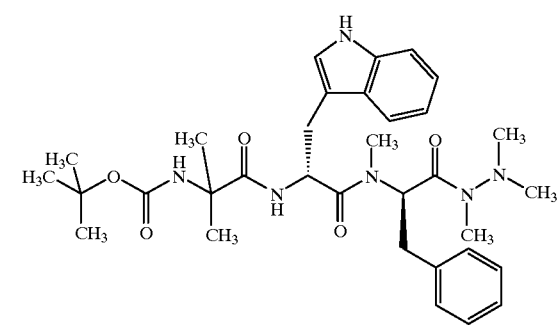

HPLC: Rt = 13.51 min (H8) LC-MS: Rt = 13.68 min, m/z = 607.4 (m+1)

2-Amino-N-((1R)-2-(1H-indol-3-yl)-1-(N-methyl-N-[(1R)-2-phenyl-1-(N,N',N'-trimethylhydrazinocarbonyl)ethyl]carbamoyl)ethyl)-2-methylpropionamide

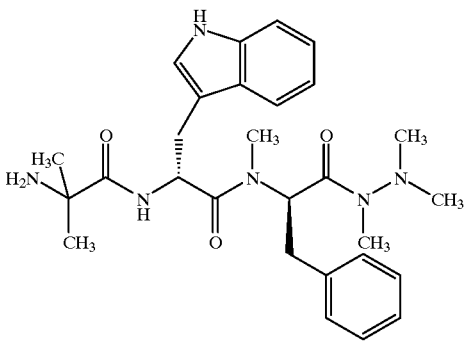

HPLC: R$_t$ = 29.8 min (A1), R$_t$ = 31.29 (B1)
LC-MS: R$_t$ = 9.21 min, m/z = 507.6 (m+1)

EXAMPLE 15

(2E)-5-Amino-5-methylhex-2-enoic acid N-methyl-N-((1R)-1-(N-methyl-N-[(1R)-1-(N-methyl-N-(piperidin-1-yl)carbamoyl)-2-phenylethyl]carbamoyl)-2-(2-naphthyl)ethyl)amide

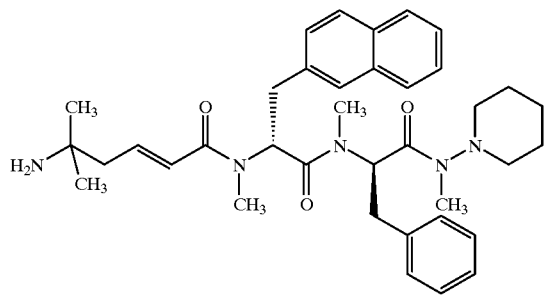

Prepared in analogy to (2E)-5-amino-5-methylhex-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide (example 4) using N-methyl-N-(piperidin-1-yl)amine instead of N,N',N'-trimethylhydrazine.

N-(Piperidin-1-yl)formamide

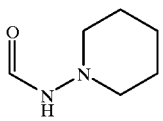

A solution of N-aminopiperidine (2.0 ml, 18.5 mmol) and methylformate (2.3 ml, 37 mmol) was stirred for four days in a sealed tube at 40° C. The mixture was concentrated in vacuo, suspended in ether (100 ml) and filtered to give 1.84 g of N-(piperidin-1-yl)formamide as a white powder.

$^1$H NMR (CDCl$_3$): δ 1.40 (m, 6H, —CH$_2$CH$_2$CH$_2$CH$_2$CH$_2$—) 2.75 (m, 4H, —CH$_2$CH$_2$—N—CH$_2$CH$_2$—) 6.80 (d, 1H, NH) 7.90+8.30+8.35 (3 s, 1H, CHO—N, rotamere).

N-Methyl-N-(piperidin-1-yl)amine

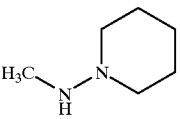

To a suspension of lithium aluminumhydride (0.66 g, 17.4 mmol) in dry tetrahydrofuran (20 ml) at 0° C. was slowly added a solution of N-(piperidin-1-yl)formamide (1.86 g, 14.5 mmol) in tetrahydrofuran (20 ml) and the mixture was stirred for 3 hours. Then ethylacetate (20 ml) and 6 N hydrogen chloride (30 ml) were added and the tetrahydrofuran was removed under reduced pressure. The mixture was titrated with 30% sodium hydroxide to pH 11, and the waterlayer was extracted with methylene chloride (3×100 ml) and the combined organic layers were dried (MgSO$_4$), filtered and concentrated in vacuo. The resulting oil was chromatographed on silica (40 g) with methylene chloride (9):methanol(1) to give 1.76 g of N-methyl-N-(piperidin-1-yl)amine as a thin yellow oil.

$^1$H NMR (CDCl$_3$): δ 1.65+1.90 (2 m, 6H, —CH$_2$CH$_2$CH$_2$CH$_2$CH$_2$—, rotamere) 2.75 (s, 3H, N—CH$_3$) 3.25 (m, 4H, —CH$_2$CH$_2$—N—CH$_2$CH$_2$—).

N-Methyl-N-[(1R)-1-(N-methyl-N-(piperidin-1-yl)carbamoyl)-2-phenylethyl]carbamic acid tert-butyl ester

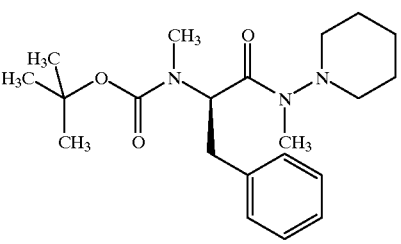

HPLC: Rt = 15.12 min (H8)
LC-MS: Rt = 15.74 min, m/z = 376.4 (m+1)

(2R)-N-Methyl-2-(methylamino)-3-phenyl-N-(piperidin-1-yl)propionamide

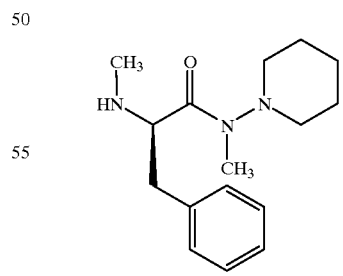

HPLC: Rt = 7.15 min (H8)
LC-MS: Rt = 8.56 min, m/z = 276.4 (m+1)

N-Methyl-N-((1R)-1-(N-methyl-N-[(1R)-1-(N-methyl-N-(piperidin-1-yl)carbamoyl)-2-phenylethyl]carbamoyl)-2-(2-naphthyl)ethyl)carbamic acid tert-butyl ester

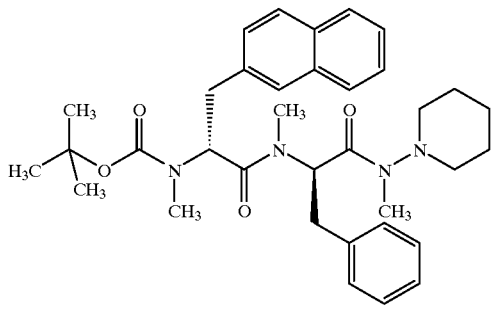

HPLC: Rt = 17.53 min (H8)
LC-MS: Rt = 18.20 min, m/z = 587.4 (m+1)

(2R)-N-Methyl-2-(methylamino)-N-[(1R)-1-(N-methyl-N-(piperidin-1-yl)carbamoyl)-2-phenylethyl]-3-(2-naphthyl)propionamide

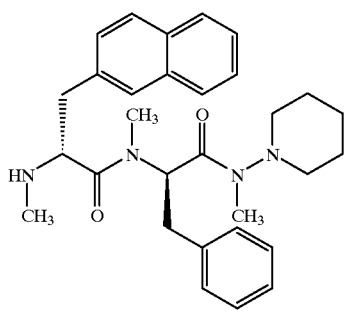

HPLC: Rt = 9.61 min (H8)
LC-MS: Rt = 10.76 min, m/z = 487.4 (m+1)

((3E)-1,1-Dimethyl-4-[N-methyl-N-((1R)-1-(N-methyl-N-[(1R)-1-(N-methyl-N-(piperidin-1-yl)carbamoyl)-2-phenylethyl]carbamoyl)-2-(2-naphthyl)ethyl)carbamoyl]but-3-enyl)carbamic acid tert-butyl ester

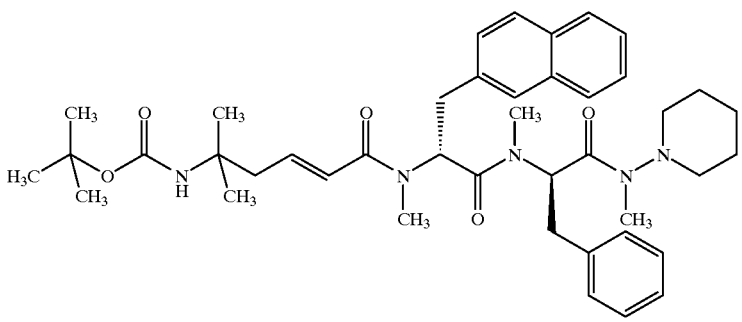

HPLC: R$_t$ = 17.42 min (H8)

(2E)-5-Amino-5-methylhex-2-enoic acid N-methyl-N-((1R)-1-(N-methyl-N-[(1R)-1-(N-methyl-N-(piperidin-1-yl)carbamoyl)-2-phenylethyl]carbamoyl)-2-(2-naphthyl)ethyl)amide

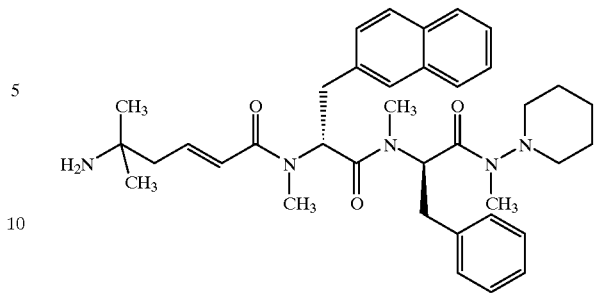

HPLC: Rt = 38.85 min (A1); Rt = 40.19 min (B1), Rt = 11.42 min (H8)
LC-MS: Rt = 12.11 min, m/z = 612.4 (m+1)

EXAMPLE 16
(2E)-5-Amino-5-methylhex-2-enoic acid N-methyl-N-(1R)-1-N-methyl-N-[(1R)-1-(N-methyl-N-(piperidin-1-yl)carbamoyl)-2-(2-thienyl)ethyl]carbamoyl)-2-(2-naphthyl)ethyl)amide

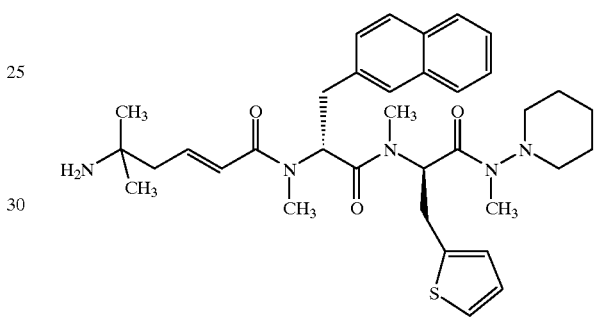

Prepared in analogy to (2E)-5-amino-5-methylhex-2-enoic acid N-methyl-N-((1R)-1-(N-methyl-N-[(1R)-1-(N-methyl-N-(piperidin-1-yl)carbamoyl)-2-phenylethyl]carbamoyl)-2-(2-naphthyl)ethyl)amide (example 15) using (2R)-2-(N-(tert-butoxycarbonyl)-N-methylamino)-3-(thiophen-2-yl)propionic acid instead of (2R)-2-(tert-butoxycarbonylmethylamino)-3-phenyl propionic acid.

N-Methyl-N-[(1R)-1-(N-methyl-N-(piperidin-1-yl)carbamoyl)-2-(2-thienyl)ethyl]carbamic acid tert-butyl ester

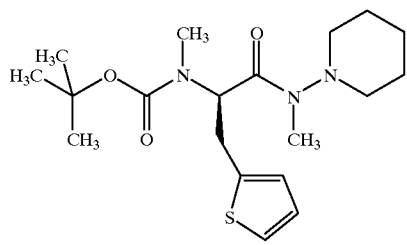

HPLC: Rt = 14.85 min (H8)
LC-MS: Rt = 15.39 min, m/z = 382.2 (m+1)

(2R)-N-Methyl-2-(methylamino)-N-(piperidin-1-yl)-3-(2-thienyl)propionamide

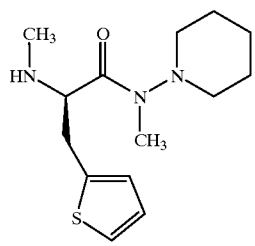

HPLC: Rt = 6.83 min (H8)
LC-MS: Rt = 8.34 min, m/z = 282.2 (m+1)

N-Methyl-N-((1R)-1-(N-methyl-N-[(1R)-1-(N-methyl-N-(piperidin-1-yl)carbamoyl)-2-(2-thienyl)ethyl]carbamoyl)-2-(2-naphthyl)ethyl)carbamic acid tert-butyl ester

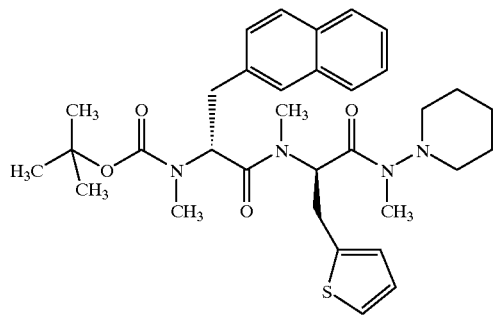

HPLC: Rt = 17.53 min (H8)
LC-MS: Rt = 17.83 min, m/z = 593.4 (m+1)

(2R)-N-Methyl-2-(methylamino)-N-[(1R)-1-(N-methyl-N-(piperidin-1-yl)carbamoyl)-2(2-thienyl)ethyl]-3-(2-naphthyl)propionamide

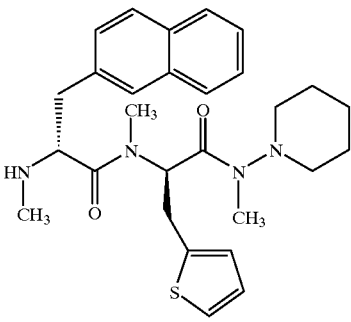

HPLC: Rt = 9.48 min (H8) LC-MS:Rt = 10.62 min, m/z = 493.4 (m+1)

((3E)-1,1-Dimethyl-4-[N-methyl-N-((1R)-1-(N-methyl-N-[(1R)-1-(N-methyl-N-(piperidin-1-yl)carbamoyl)-2-(2-thienyl)ethyl]carbamoyl)-2-(2-naphthyl)ethyl)carbamoyl]but-3-enyl)carbamic acid tert-butyl ester

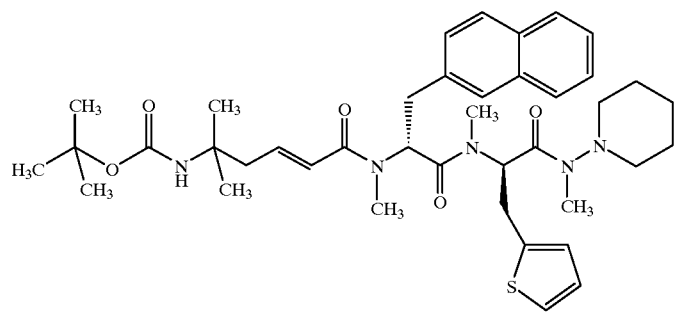

HPLC: $R_t$ = 17.19 min (H8)

(2E)-5-Amino-5-methylhex-2-enoic acid N-methyl-N-((1R)-1-(N-methyl-N-[(1R)-1-N-methyl-N-(piperidin-1-yl)carbamoyl)-2-(2-thienyl)ethyl]carbamoyl)-2-(2-naphthyl)ethyl)amide

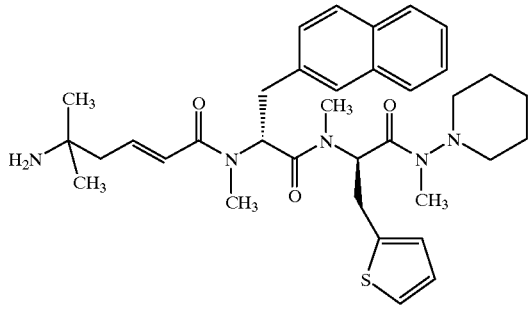

HPLC: Rt = 39.47 min (A1), Rt = 41.43 min (B1), Rt = 11.30 min (H8) LC-MS: Rt = 12.17 min, m/z = 618.4 (m+1)

EXAMPLE 17

(2E)-5-Amino-5-methylhex-2-enoic acid N-((1R)-1-(N-[(1R)-1-benzyl-2-oxo-2-(3-oxopyrazolidin-1-yl)ethyl]-N-methylcarbamoyl)-2-(2-naphthyl)ethyl)-N-methylamide

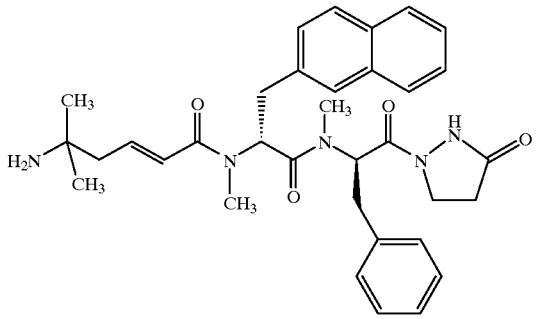

Prepared in analogy to (2E)-5-amino-5-methylhex-2-enoic acid N-((1R)-1-(N-[(1R)-2-(N'-acetylhydrazino)-1-benzyl-2-oxoethyl]-N-methylcarbamoyl)-2-(2-naphthyl)ethyl)-N-methylamide (example 1) using 3-pyrazolidinone instead of acetic acid hydrazide.

N-[(1R)-1-Benzyl-2-oxo-2-(3-oxopyrazolidin-1-yl)ethyl]-N-methylcarbamic acid tert-butyl ester

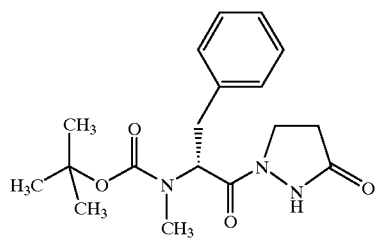

HPLC: Rt = 10.70 min (H8) LC-MS: Rt = 10.34 min, m/z = 348.4 (m +1)

N-((1R)-1-(N-[(1R)-1-Benzyl-2-oxo-2-(3-oxopyrazolidin-1-yl)ethyl]-N-methylcarbamoyl)-2-(2-naphthyl)ethyl)-N-methylcarbamic acid tert-butyl ester

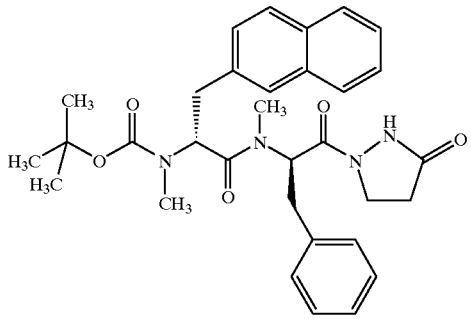

HPLC: Rt = 14.22 min (H8) LC-MS: Rt = 14.84 min, m/z = 559.4 (m+1)

(2R)-N-[(1R)-1-Benzyl-2-oxo-2-(3-oxopyrazolidin-1-yl)ethyl]-N-methyl-2-(methylamino)-3-(2-naphthyl)propionamide

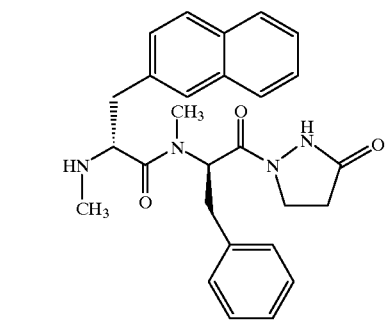

HPLC: Rt=8,26 min (H8).

(2E)-5-Amino-5-methylhex-2-enoic acid N-((1R)-1-(N-[(1R)-1-benzyl-2-oxo-2-(3-oxopyrazolidin-1-yl)ethyl]-N-methylcarbamoyl)-2-(2-naphthyl)ethyl)-N-methylamide

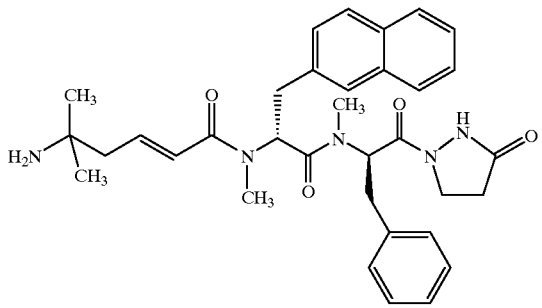

HPLC: Rt = 29.21 min (A1), Rt = 8.43 min (H8) LC-MS:Rt = 9.24 min, m/z = 584.4 (m+1)

EXAMPLE 18

(2E)-5-Amino-5-methylhex-2-enoic acid N-methyl-N-((1R)-1-{N-methyl-N-[(1R)-2-phenyl-1-((piperidin-1-yl)carbamoyl)ethyl]carbamoyl}-2-(2-naphthyl)ethyl)amide

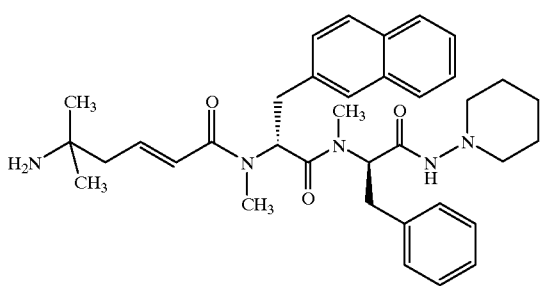

Prepared in analogy to (2E)-5-amino-5-methylhex-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide (example 4) using N-aminopiperidine instead of trimethylhydrazine.

HPLC: Rt=34.78 min (A1), Rt=33.74 min (B1); LC-MS: Rt=9.81 min, m/z=598.4 (m+1).

EXAMPLE 19

(2E)-5-Amino-5-methylhex-2-enoic acid N-methyl-N-((1R)-1-{N-methyl-N-[(1R)-2-phenyl-1-((pyrrolidine-1-yl)carbamoyl)ethyl]carbamoyl}-2-(2-naphthyl)ethyl)amide

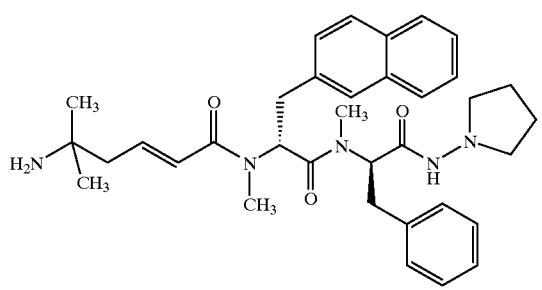

Prepared in analogy to (2E)-5-amino-5-methylhex-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide (example 4) using N-aminopyrrolidine instead of trimethylhydrazine.

HPLC: Rt=31.78 min (A1), Rt=30.78 min (B1); LC-MS: Rt=8.92 min, m/z=584.4 (m+1).

EXAMPLE 20

(2E)-5-Amino-5-methylhex-2-enoic acid N-((1R)-2-(biphenyl-4-yl)-1-{N-methyl-N-[(1R)-2-phenyl-1-((pyrrolidine-1-yl)carbamoyl)ethyl]carbamoyl}ethyl)-N-methylamide

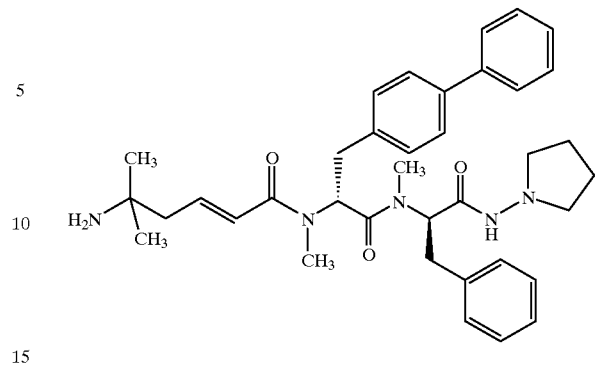

Prepared in analogy to (2E)-5-amino-5-methylhex-2-enoic acid N-methyl-N-((1R)-1-{N-methyl-N-[(1R)-2-phenyl-1-((pyrrolidine-1-yl)carbamoyl)ethyl]carbamoyl}-2-(2-naphthyl)ethyl)amide (example 19) using (2R)-N-tert-butoxycarbonylamino-N-methyl-D-4,4'-biphenylalanine instead of 2(R)-(N-tert-butoxycarbonyl-N-methylamino)-3-(naphth-2-yl)propionic acid.

HPLC: Rt=34.80 min (A1), Rt=34.04 min (B1); LC-MS: Rt=9.46 min, m/z=610.4 (m+1).

EXAMPLE 21

2-Amino-N-(2-benzyloxy-1-{N-methyl-N-[(1R)-2-phenyl-1-(N,N',N'-trimethylhydrazinocarbonyl)ethyl]carbamoyl}ethyl)-2-methylpropionamide

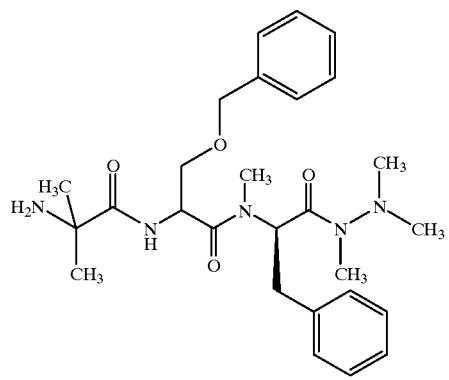

Prepared in analogy to (2E)-5-amino-5-methylhex-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide (example 4) using 3-benzyloxy-2-tert-butoxycarbonylaminopropionic acid instead of 2(R)-(N-tert-butoxycarbonyl-N-methylamino)-3-(naphth-2-yl)propionic acid and N-tert-butyloxycarbonyl-a-aminoisobutyric acid instead of (2E)-5-(tert-butyloxycarbonylamino)-5-methylhex-2-enoic acid.

Isolated as two diastereoisomers:

Compound 1.
HPLC: Rt=32.20 min (A1), Rt=33.78 min (B1); LC-MS: Rt=9.64 min, m/z=498.2 (m+1).

Compound 2.
HPLC: Rt=31.05 min (A1), Rt=32.56 min (B1); LC-MS: Rt=9.42 min, m/z=498.2 (m+1).

EXAMPLE 22

2-Amino-N-(2-benzyloxy-1-{N-[(1R)-1-(N',N'dimethylhydrazinocarbonyl)-3-phenylpropyl]-N-methylcarbamoylethyl)-2-methylpropionamide

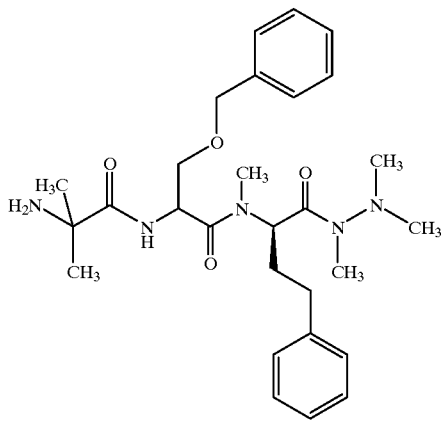

Prepared in analogy to 2-amino-N-(2-benzyloxy-1-{N-methyl-N-[(1R)-2-phenyl-1-(N,N',N'-trimethylhydrazinocarbonyl)ethyl]carbamoyl}ethyl)-2-methylpropionamide (example 21) using (2R)-2-methylamino-4-phenylbutyric acid N,N dimethylhydrazine instead of (2R)-2-methylamino-3-phenylpropionic acid N',N'-dimethylhydrazine.

Isolated as two diastereoisomers:
Compound 1.
HPLC: Rt=28.44 min (A1), Rt=28.73 min (B1); LC-MS: Rt=8.21 min, m/z=498.4 (m+1).
Compound 2.
HPLC: Rt=30.50 min (A1), Rt=30.50 min (B1); LC-MS: Rt=8.61 min, m/z=498.4 (m+1).

EXAMPLE 23
2-Amino-N-{2-benzyloxy-1-[N-((1R)-1-(N',N'-dimethylhydrazinocarbonyl)-3-phenylpropyl)carbamoyaethyl}-2-methylpropionamide

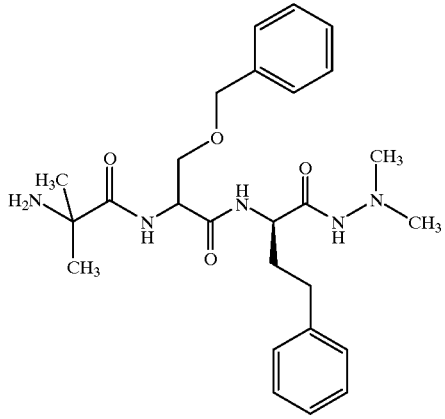

Prepared in analogy to 2-amino-N-(2-benzyloxy-1-{N-[(1R)-1-(N',N'-dimethylhydrazinocarbonyl)-3-phenylpropyl]-N-methylcarbamoyl}ethyl)-2-methylpropionamide (example 22) using (2R)-2-amino-4-phenylbutyric acid N,N dimethylhydrazine instead of (2R)-2-methylamino-3-phenylbutyric acid N',N'-dimethylhydrazine.

Isolated as two diastereoisomers:
Compound 1.
HPLC: Rt=27.82 min (A1), Rt=27.78 min (B1); LC-MS: Rt=8.41 min, m/z=484.4 (m+1).

Compound 2.
HPLC: Rt=29.48 min (A1), Rt=29.58 min (B1); LC-MS: Rt=8.67 min, m/z=498.4 (m+1).

EXAMPLE 24
2-Amino-N-[(1R)-1-[(1R)-1-(N',N'-dimethylhydrazinocarbonyl)-3-phenylpropylcarbamoyl]-2-(1H-indol-3-yl)ethyl]-2-methylpropionamide

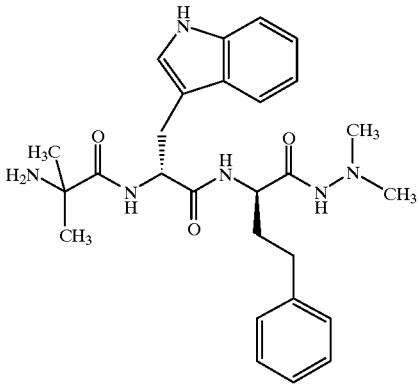

Prepared in analogy to 2-amino-N-{2-benzyloxy-1-[N-((1R)-1-(N',N'-dimethylhydrazinocarbonyl)-3-phenylpropyi)carbamoyl]ethyl}-2-methylpropionamide (example 23) using (2R)-2-tert-butoxycarbonylamino-3-(1H-indol-3-yl)propionic acid instead of 3-benzyloxy-2-tert-butoxycarbonylaminopropionic acid.

HPLC: Rt=25.65 min (A1), Rt=27.71 min (B1); LC-MS: Rt=8.11 min, m/z=493.4 (m+1).

EXAMPLE 25
2-Amino-N-[(1R)-1-{N-[(1R)-1-(N',N'-dimethylhydrazinocarbonyl)-3-phenylpropyl]-N-methylcarbamoyl}-2-(1H-indol-3-yl)ethyl]-2-methylpropionamide

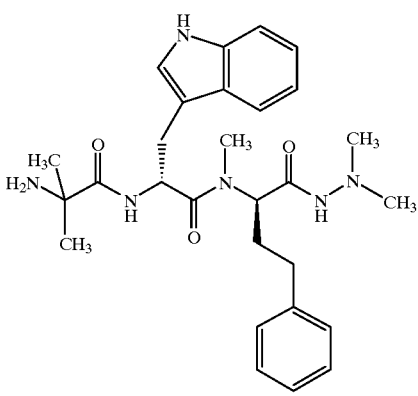

Prepared in analogy to 2-amino-N-[(1R)-1-[(1R)-1-(N',N'-dimethylhydrazinocarbonyl)-3-phenylpropylcarbamoyl]-2-(1H-indol-3-yl)ethyl]-2-methylpropionamide (example 24) using (2R)-2-methylamino-4-phenylbutyric acid N,N dimethylhydrazine instead of (2R)-2-amino-3-phenylbutyric acid N',N'-dimethylhydrazine.

HPLC: Rt=27.02 min (A1), Rt=27.31 min (B1); LC-MS: Rt=8.07 min, m/z=507.4 (m+1).

What is claimed is:

1. A compound of formula I

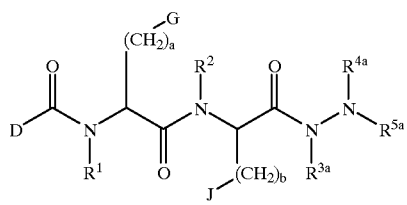

formula I wherein

- $R^1$ and $R^2$ are independently hydrogen, or $C_{1-6}$-alkyl optionally substituted with one or more aryl or hetaryl;
- $R^{3a}$ is hydrogen, $C_{1-6}$-alkyl optionally substituted with one or more aryl or hetaryl, or aryl or hetaryl optionally substituted with one or more $C_{1-6}$-alkyl;
- $R^{4a}$ is $C_{1-6}$-alkyl optionally substituted with one or more aryl or hetaryl, or $C_{1-7}$-acyl;
- $R^{5a}$ is hydrogen, $C_{1-6}$-alkyl optionally substituted with one or more aryl or hetaryl, or aryl or hetaryl optionally substituted with one or more $C_{1-6}$-alkyl; or
- $R^{3a}$ and $R^{4a}$ together with the nitrogen atoms to which they are attached may form a heterocyclic system optionally substituted with one or more $C_{1-6}$-alkyl, halogen, amino, hydroxyl, aryl or hetaryl; or
- $R^{3a}$ and $R^{5a}$ together with the nitrogen atoms to which they are attached may form a heterocyclic system optionally substituted with one or more $C_{1-6}$-alkyl, halogen, amino, hydroxyl, aryl or hetaryl; or
- $R^{4a}$ and $R^{5a}$ together with the nitrogen atom to which they are attached may form a heterocyclic system optionally substituted with one or more $C_{1-6}$-alkyl, halogen, amino, hydroxyl, aryl or hetaryl;
- a and b are independently 0, 1 or 2;

G is hydrogen, —O—$(CH_2)_k$—$R^{27}$,

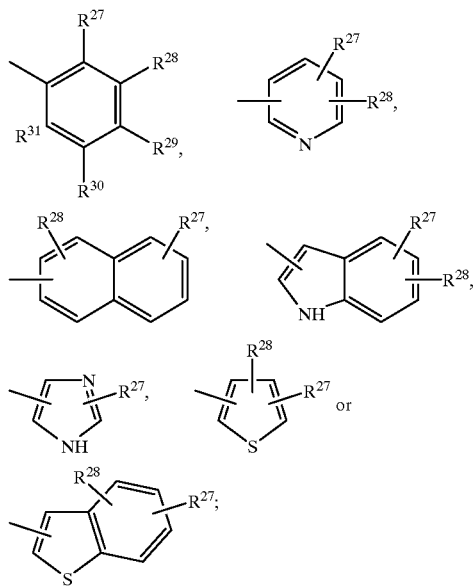

J is hydrogen, —O—$(CH_2)_l$—$R^{32}$,

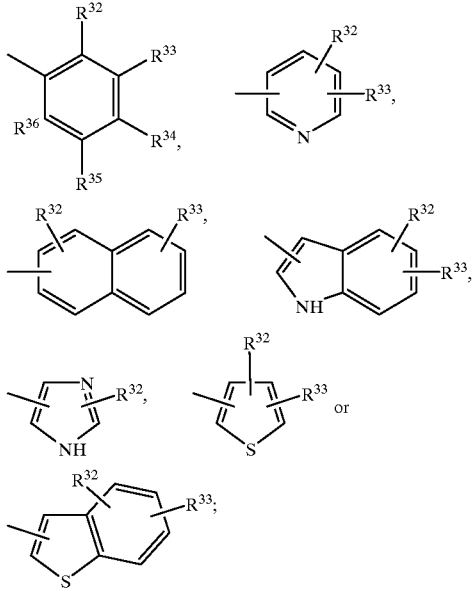

wherein $R^{27}$, $R^{28}$, $R^{29}$, $R^{30}$, $R^{31}$, $R^{32}$, $R^{33}$, $R^{34}$, $R^{35}$ and $R^{36}$ independently are hydrogen, halogen aryl, hetaryl, $C_{1-6}$-alkyl or $C_{1-6}$-alkoxy; k and l are independently 0, 1 or 2;

D is

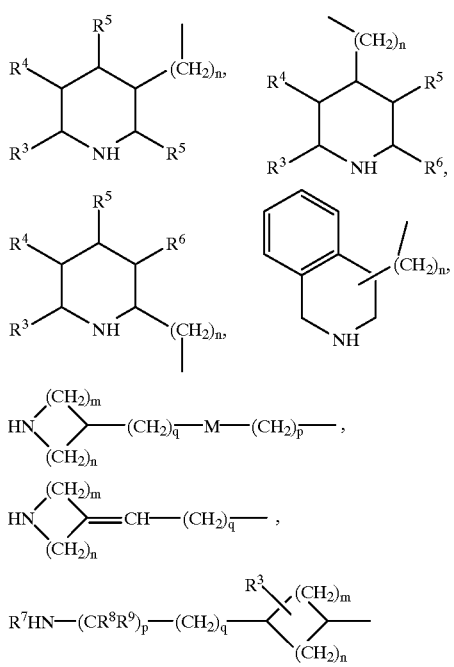

wherein $R^3$, $R^4$, $R^5$, $R^6$, $R^7$, $R^8$ and $R^9$ are independently hydrogen or $C_{1-6}$-alkyl optionally substituted with one or more halogen, amino, hydroxyl, aryl or hetaryl;

n, m and q are independently 0, 1, 2, or 3;

p is 0 or 1;

M is —CR¹¹=CR¹¹ᵃ—, arylene, hetarylene, —O—, —S— or a valence bond;

R¹¹ and R¹¹ᵃ are independently hydrogen, or $C_{1-6}$-alkyl optionally substituted with one or more aryl or hetaryl; or D is

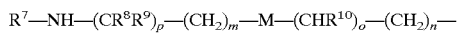

wherein

R⁷, R⁸, R⁹ and R¹⁰ are independently hydrogen or $C_{1-6}$ alkyl optionally substituted with one or more halogen, amino, hydroxyl, aryl or hetaryl; or R⁷ and R⁸ or R⁷ and R⁹ or R⁸ and R⁹ may optionally form —(CH₂)ᵢ—U—(CH₂)ⱼ—, wherein i and j independently are 1 or 2 and U is —O—, —S— or a valence bond;

n and m are independently 0, 1, 2, or 3;

o and p are independently 0 or 1;

M is —CR¹¹=CR¹¹ᵃ—, arylene, hetarylene, —O—, —S— or a valence bond;

R¹¹ and R¹¹ᵃ are independently hydrogen, or $C_{1-6}$-alkyl optionally substituted with one or more aryl or hetaryl;

or a pharmaceutically acceptable salt thereof.

2. The compound according to claim 1 wherein R¹ is $C_{1-6}$-alkyl.

3. The compound according to claim 1 wherein R² is hydrogen or $C_{1-6}$-alkyl.

4. The compound according to claim 1 wherein R³ᵃ is hydrogen or $C_{1-6}$-alkyl.

5. The compound according to claim 1 wherein R⁴ᵃ is $C_{1-6}$-alkyl or $C_{1-7}$-acyl.

6. The compound according to claim 1 wherein R⁵ᵃ is hydrogen or $C_{1-6}$-alkyl.

7. The compound according to claim 1 wherein R³ᵃ and R⁴ᵃ together with the nitrogen atom to which they are attached form a heterocyclic system.

8. The compound according to claim 1 wherein R⁴ᵃ and R⁵ᵃ together with the nitrogen atom to which they are attached form a heterocyclic system.

9. The compound according to claim 1 wherein a and b independently are 1 or 2.

10. The compound according to claim 1 wherein G is —O—(CH₂)ₖ—R²⁷,

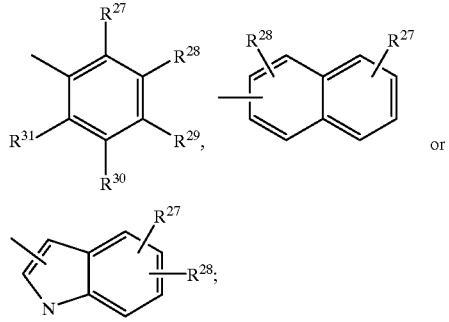

wherein R²⁷, R²⁸, R²⁹, R³⁰ and R³¹ independently are hydrogen, halogen, aryl, hetaryl, $C_{1-6}$-alkyl or $C_{1-6}$-alkoxy;

k is 0, 1 or 2.

11. The compound according to claim 1 wherein J is

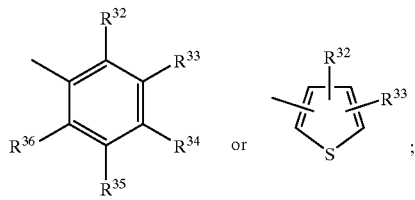

wherein R³², R³³, R³⁴, R³⁵ and R³⁶ independently are hydrogen, halogen, aryl, hetaryl, $C_{1-6}$-alkyl or $C_{1-6}$-alkoxy.

12. The compound according to claim 1 wherein D is

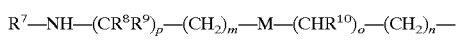

wherein R⁷, R⁸, R⁹ and R¹⁰ are independently hydrogen or $C_{1-6}$ alkyl optionally substituted with one or more halogen, amino, hydroxyl, aryl or hetaryl;

n and m are independently 0, 1, 2, or 3;

o and p are independently 0 or 1;

M is —CR¹¹=CR¹¹ᵃ—, arylene, —O—, or —S—;

R¹¹ and R¹¹ᵃ are independently hydrogen, or $C_{1-6}$-alkyl optionally substituted with one or more aryl or hetaryl.

13. The compound according to claim 1 wherein D is

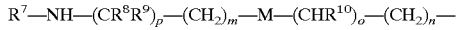

wherein R⁷, R⁸, R⁹ and R¹⁰ independently are hydrogen or $C_{1-6}$ alkyl optionally substituted with one or more halogen, amino, hydroxyl, aryl or hetaryl;

n and m are independently 0, 1, 2, or 3;

o and p are independently 0 or 1;

M is a valence bond.

14. The compound according to claim 1 wherein R⁸ and R⁹ form —(CH₂)ᵢ—U—(CH₂)ⱼ—, wherein i and j independently are 1 or 2 and U is —O—, —S— or a valence bond.

15. The compound according to claim 1 selected from (2E)-5-Amino-5-methylhex-2-enoic acid N-((1R)-1-{N-[(1R)-2-(N'-acetylhydrazino)-1-benzyl-2-oxoethyl]-N-methylcarbamoyl}-2-(2-naphthyl)ethyl)-N-methylamide

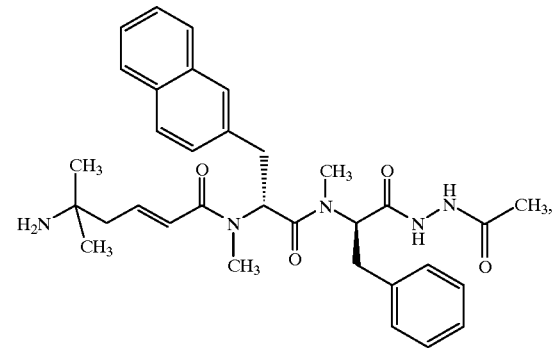

(2E)-5-Amino-5-methylhex-2-enoic acid N-((1R)-1-{N-[(1R)-2-(N'-acetyl-N-methylhydrazino)-1-benzyl-2-oxoethyl]-N-methylcarbamoyl}-2-(2-naphthyl)ethyl)-N-methylamide

77

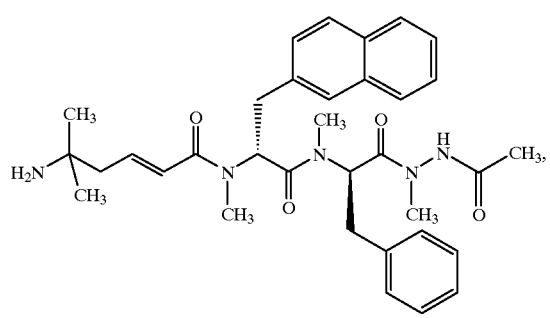

(2E)-5-Amino-5-methylhex-2-enoic acid N-((1R)-1-{N-[(1R)-2-(N'-acetyl-N'-methylhydrazino)-1-benzyl-2-oxoethyl]-N-methylcarbamoyl}-2-(2-naphthyl)ethyl)-N-methylamide

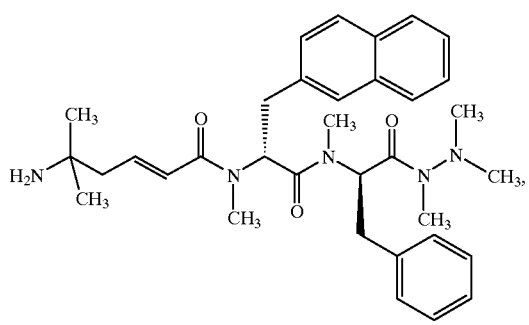

(2E)-5-Amino-5-methylhex-2-enoic acid N-methyl-N-((1R)-1-{N-methyl-N-[(1R)-2-phenyl-1-(N,N',N'-trimethylhydrazinocarbonyl)ethyl]carbamoyl}-2-(2-naphthyl)-ethyl)amide 3-Aminomethyl-N-methyl-N-((1R)-1{-N-methyl-N-[(1R)-2-phenyl-1-(N,N',N'-trimethylhydrazirocarbonyl)ethyl]carbamoyl}-2-(2-naphthyl)ethyl)benzamide

78

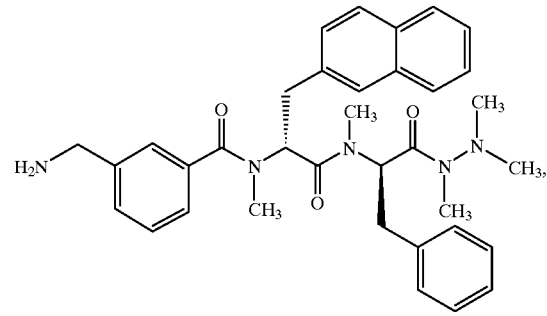

(2E)-5-Amino-5-methylhex-2-enoic acid N-((1R)-1-(N-[(1R)-1-(N',N'-dimethylhydrazinocarbonyl)-2-phenylethyl]-N-methylcarbamoyl)-2-(2-naphthyl)ethyl)-N-methylamide

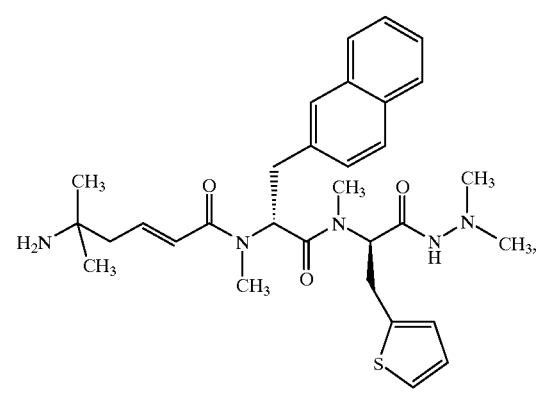

(2E)-5-Amino-5-methylhex-2-enoic acid N-((1R)-1-(N-[(1R)-1-(N',N'-dimethylhydrazinocarbonyl)-2-(2-thienyl)ethyl]-N-methylcarbamoyl)-2-(2-naphthyl)ethyl)-N-methylamide N-((1R)-1-(N-[(1R)-1-(N',N'-Dimethylhydrazinocarbonyl)-2-phenylethyl]-N-methylcarbamoyl)-2-(2-naphthyl)ethyl)-N-methyl-3-(N-methylaminomethyl)benzamide

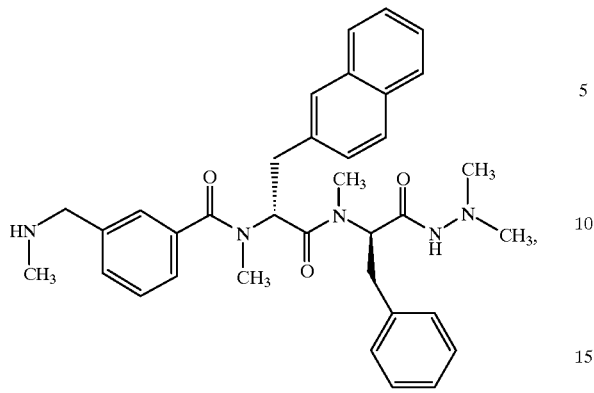

(2E)-5-Amino-5-methylhex-2-enoic acid N-((1R)-2-(biphenyl4-yl)-1-(N-methyl-N-[(1R)-2-phenyl-1-(N,N',N'-trimethylhydrazinocarbonyl)ethyl]carbamoyl)ethyl)-N-methylamide

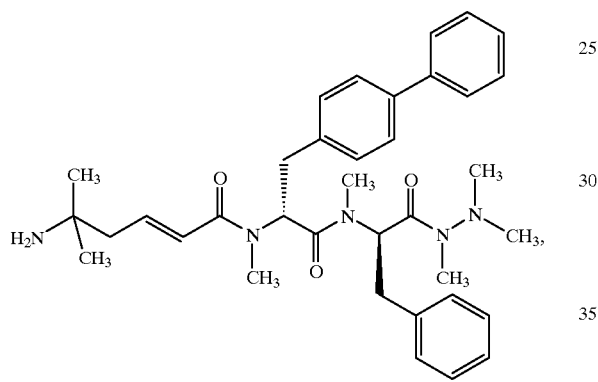

(2E)-4-(1-Aminocyclobutyl)but-2-enoic acid N-methyl-N-((1R)-1-(N-methyl-N-[(1R)-2-phenyl-1-(N,N',N'-trimethylhydrazinocarbonyl)ethyl]carbamoyl)-2-(2-naphthyl)ethyl)amide

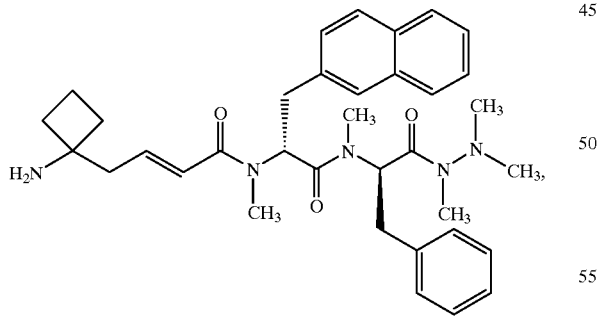

(2E)-5-Amino-5-methylhex-2-enoic acid N-((1R)-2-(biphenyl-4-yl)-1-(N-methyl-N-[(1R)-2-phenyl-1-((piperidin-1-yl)carbamoyl)ethyl]carbamoyl)ethyl)-N-methylamide

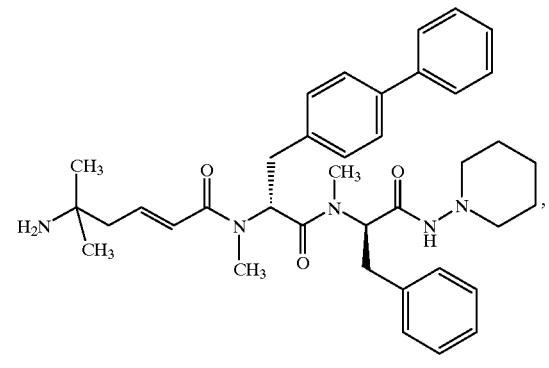

(2E)-5-Amino-5-methylhex-2-enoic acid N-methyl-N-((1R)-1-(N-methyl-N-[(1R)-2-(2-thienyl)-1-(N,N',N'-trimethylhydrazinocarbonyl)ethyl]carbamoyl)-2-(2-naphthyl)ethyl)amide

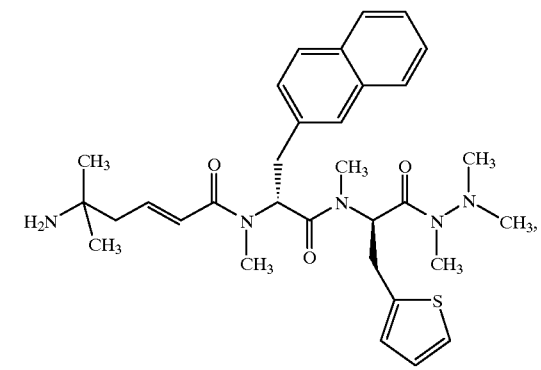

(2E)-5-Amino-5-methylhex-2-enoic acid N-((1R)-2-(1H-indol-3-yl)-1-(N-methyl-N[(1R)-2-phenyl-1-(N,N',N'-trimethylhydrazinocarbonyl)ethyl]carbamoyl)ethyl)amide

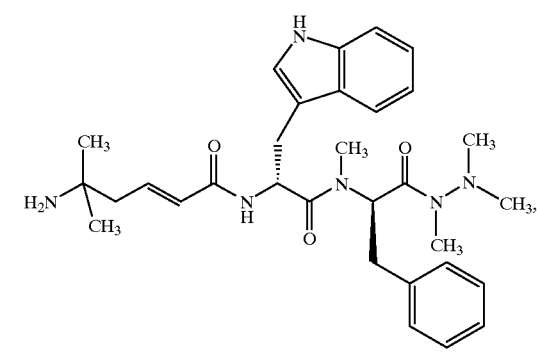

2-Amino-N-((1R)-2-(1H-indol-3-yl)-1-(N-methyl-N-[(1R)-2-phenyl-1-(N,N',N'-trimethylhydrazinocarbonyl)ethyl]carbamoyl)ethyl)-2-methylpropionamide

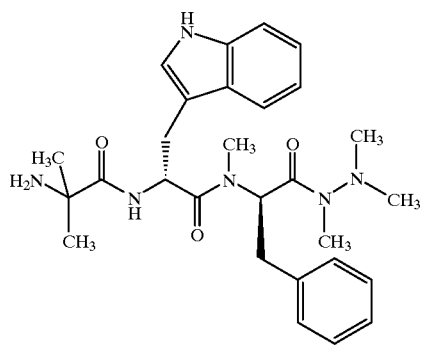

(2E)-5-Amino-5-methylhex-2-enoic acid N-methyl-N-((1R)-1-(N-methyl-N-[(1R)-1-(N-methyl-N-(piperidin-1-yl)carbamoyl)-2-phenylethyl]carbamoyl)-2-(2-naphthyl)ethyl)amide

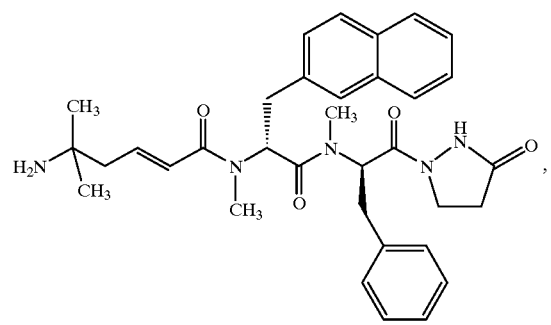

(2E)-5-Amino-5-methylhex-2-enoic acid N-methyl-N-((1R)-1-{N-methyl-N-[(1R)-2-phenyl-1-((piperidin-1-yl)carbamoyl)ethyl]carbamoyl}-2-(2-naphthyl)ethyl)amide

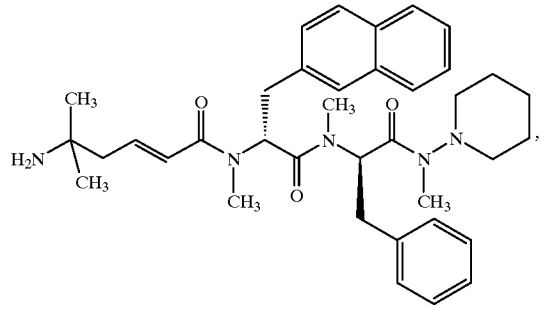

(2E)-5-Amino-5-methylhex-2-enoic acid N-methyl-N-((1R)-1-(N-methyl-N-[(1R)-1-(N-methyl-N-(piperidin-1-yl)carbamoyl)-2-(2-thienyl)ethyl]carbamoyl)-2-(2-naphthyl)ethyl)amide

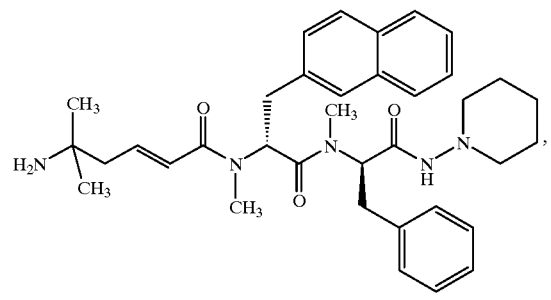

(2E)-5-Amino-5-methylhex-2-enoic acid N-methyl-N-((1R)-1-{N-methyl-N-[(1R)-2-phenyl-1-((pyrrolidine-1-yl)carbamoyl)ethyl]carbamoyl}-2-(2-naphthyl)ethyl)amide

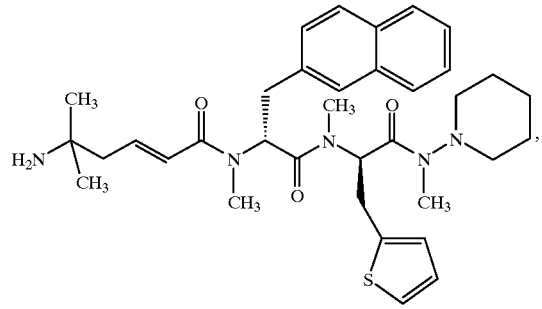

(2E)-5-Amino-5-methylhex-2-enoic acid N-((1R)-1-(N-[(1R)-1-benzyl-2-oxo-2-(3-oxopyrazolidin-1-yl)ethyl]-N-methylcarbamoyl)-2-(2-naphthyl)ethyl)-N-methylamide

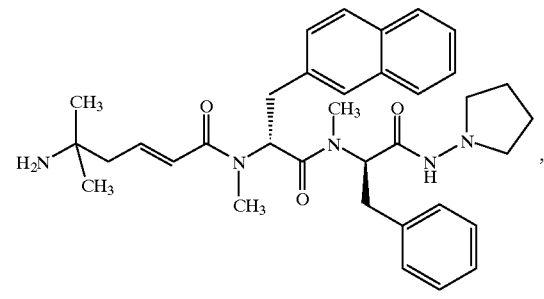

(2E)-5-Amino-5-methylhex-2-enoic acid N-((1R)-2-(biphenyl-4-yl)-1-{N-methyl-N-[(1R)-2-phenyl-1-((pyrrolidin-1-yl)carbamoyl)ethyl]carbamoyl}ethyl)-N-methylamide

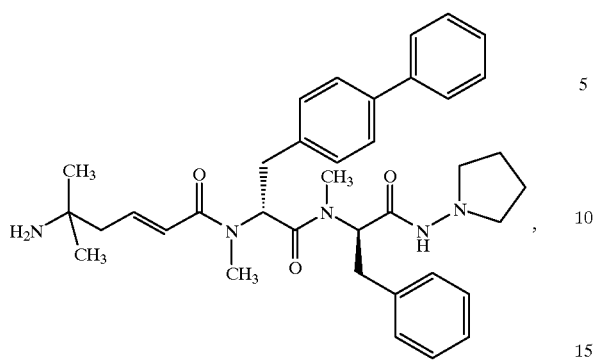

2-Amino-N-(2-benzyloxy-1-{N-methyl-N-[(1R)-2-phenyl-1-(N,N',N'-trimethylhydrazinocarbonyl)ethyl]carbamoyl}ethyl)-2-methylpropionamide

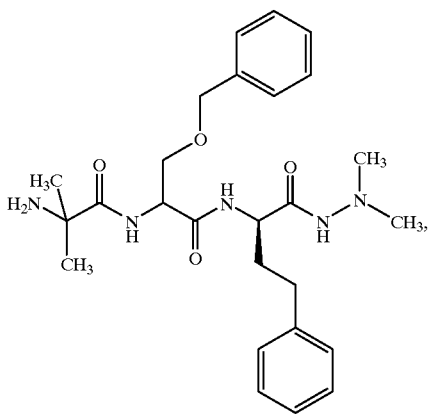

2-Amino-N-[(1R)-1-[(1R)-1-(N',N'-dimethylhydrazinocarbonyl)-3-phenylpropylcarbamoyl]-2-(1H-indol-3-yl)ethyl]-2-methylpropionamide

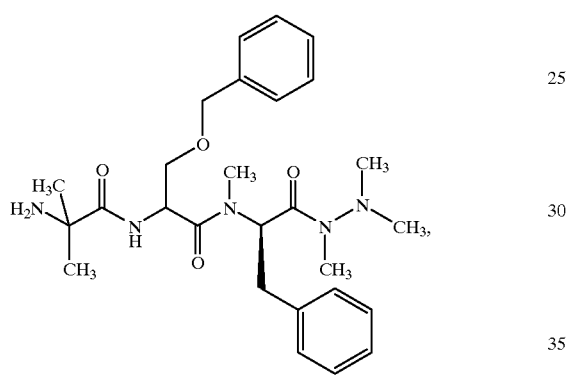

2-Amino-N-(2-benzyloxy-1-{N-[(1R)-1-(N',N'-dimethylhydrazinocarbonyl)-3-phenylpropyl]-N-methylcarbamoyl}ethyl)-2-methylpropionamide

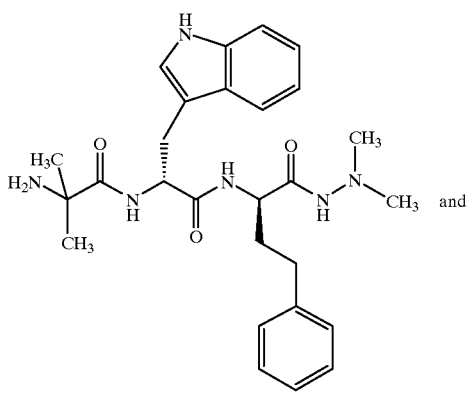

2-Amino-N-((1R)-1-{N-[(1R)-1-(N',N'-dimethylhydrazinocarbonyl)-3-phenylpropyl]-N-methylcarbamoyl}-2-(1H-indol-3-yl)ethyl]-2-methylpropionamide

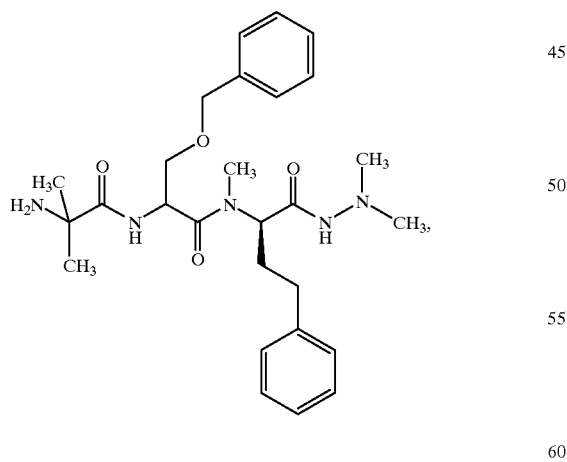

2-Amino-N-{2-benzyloxy-1-[N-((1R)-1-(N',N'-dimethylhydrazinocarbonyl)-3-phenylpropyl)carbamoyl]ethyl}-2-methylpropionamide 16. A pharmaceutical composition comprising, as an active ingredient, an effective amount of a compound of claim 1 or a pharmaceutically acceptable salt thereof together with a pharmaceutically acceptable carrier or diluent.

17. A method of stimulating the release of growth hormone from the pituitary of a mammal, the method comprising administering to said mammal an effective amount of a compound of claim 1 or of a composition of claim 16.

* * * * *

UNITED STATES PATENT AND TRADEMARK OFFICE
CERTIFICATE OF CORRECTION

PATENT NO. : 6,083,908
DATED : July 4, 2000
INVENTOR(S) : Michael Ankersen

It is certified that error appears in the above-identified patent and that said Letters Patent is hereby corrected as shown below:

Column 74,
Line 40, please delete "

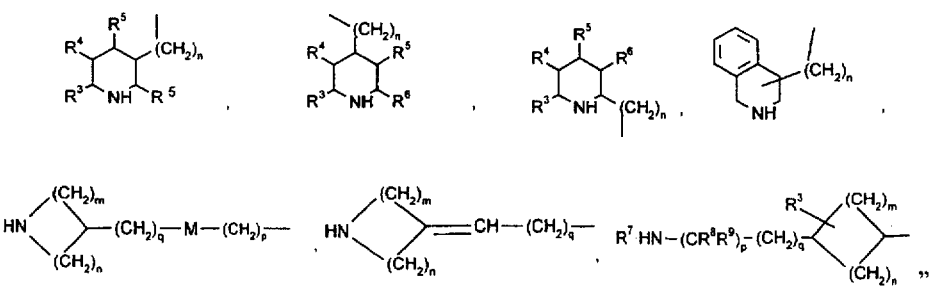

and insert --

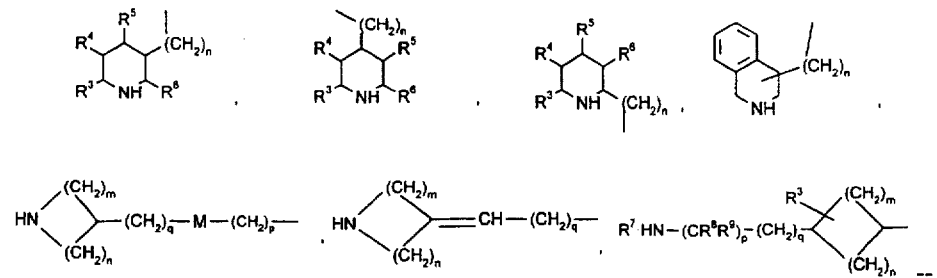

Column 77,
Line 60, please delete "trimethylhydrazirocarbonyl)ethyl]carbomoyl}-2-(2-", and insert -- trimethylhydrazinocarbonyl)ethyl]carbamoyl}-2-(2- --.

Column 79,
Line 20, please delete "(biphenyl4-yl)", and insert -- (biphenyl-4-yl) --.

UNITED STATES PATENT AND TRADEMARK OFFICE
CERTIFICATE OF CORRECTION

PATENT NO.    : 6,083,908
DATED         : July 4, 2000
INVENTOR(S)   : Michael Ankersen It is certified that error appears in the above-identified patent and that said Letters Patent is hereby corrected as shown below:

Column 82,
Line 38, please delete "((pyrrolidine-", and insert -- pyrrolidin --.

Signed and Sealed this

Ninth Day of April, 2002

Attest:

Attesting Officer

JAMES E. ROGAN
Director of the United States Patent and Trademark Office